(12) United States Patent
David et al.

(10) Patent No.: US 9,867,884 B2
(45) Date of Patent: *Jan. 16, 2018

(54) VASCULAR DELIVERY SYSTEMS

(71) Applicant: Ben-Gurion University of the Negev Research and Development Authority, Beer Sheva (IL)

(72) Inventors: Ayelet David, Omer (IL); Gonen Ashkenasy, Omer (IL); Yosi Shamay, Kfar Sabbah (IL)

(73) Assignee: Ben-Gurion University of Negev Research & Development Authority, Beer Sheva (IL)

(*) Notice: Subject to any disclaimer, the term of this patent is extended or adjusted under 35 U.S.C. 154(b) by 0 days.

This patent is subject to a terminal disclaimer.

(21) Appl. No.: 14/463,165

(22) Filed: Aug. 19, 2014

(65) Prior Publication Data

US 2015/0056157 A1  Feb. 26, 2015

Related U.S. Application Data

(63) Continuation of application No. 12/954,109, filed on Nov. 24, 2010, now Pat. No. 8,840,874, which is a continuation of application No. PCT/IL2009/000152, filed on Feb. 11, 2009.

(60) Provisional application No. 61/071,461, filed on Apr. 30, 2008.

(51) Int. Cl.
| | |
|---|---|
| *A61K 31/785* | (2006.01) |
| *A61K 38/10* | (2006.01) |
| *A61P 35/00* | (2006.01) |
| *A61P 35/04* | (2006.01) |
| *A61K 47/48* | (2006.01) |
| *A61K 49/00* | (2006.01) |
| *A61K 31/704* | (2006.01) |
| *G01N 33/50* | (2006.01) |

(52) U.S. Cl.
CPC ...... *A61K 47/48176* (2013.01); *A61K 31/704* (2013.01); *A61K 47/48092* (2013.01); *A61K 47/48338* (2013.01); *A61K 49/0017* (2013.01); *G01N 33/5091* (2013.01)

(58) Field of Classification Search
CPC ............ A61K 31/704; A61K 47/48092; A61K 47/48176; A61K 47/48338; A61K 49/0017
See application file for complete search history.

(56) References Cited

U.S. PATENT DOCUMENTS

| | | | |
|---|---|---|---|
| 5,643,873 A | 7/1997 | Barrett et al. | |
| 6,027,709 A | 2/2000 | Little et al. | |
| 6,593,148 B1 | 7/2003 | Narayanan | |
| 6,984,667 B2* | 1/2006 | Theoharides | A61K 31/13 424/464 |
| 6,995,274 B2 | 2/2006 | Lugade et al. | |
| 7,005,518 B2 | 2/2006 | Peng et al. | |
| 7,504,089 B2 | 3/2009 | Lugade et al. | |
| 8,840,874 B2* | 9/2014 | David | A61K 47/48092 424/78.18 |
| 2008/0318246 A1 | 12/2008 | Lawrence et al. | |
| 2009/0186802 A1 | 7/2009 | Alluis et al. | |
| 2010/0111949 A1 | 5/2010 | Qin et al. | |
| 2012/0014904 A1* | 1/2012 | David | A61K 47/48092 424/78.3 |

FOREIGN PATENT DOCUMENTS

| | | |
|---|---|---|
| WO | 2007/134236 A2 | 11/2007 |
| WO | 2009/012109 A2 | 1/2009 |
| WO | 2009/133545 A2 | 11/2009 |

OTHER PUBLICATIONS

Zhou et al. (Biomaterials, published online May 10, 2014, pp. 6622-6635).*
Zhong et al. (International Journal of Oncology, published online on Dec. 28, 2012, pp. 373-383).*
Ke (International Journal of Nanomedicine, 2(2), pp. 191-199, published 2007).
DeFrees et al. Journal of the American Chemical Society, 118, Published 1996, pp. 6101-6104.
Lin et al. Bioorganic & Medicinal Chemistry Letters vol. 6, No. 22, Published 1996, pp. 2755-2760.
Nelson et al. The American Society for Clinical Investigation, Inc. vol. 91, Published 1993, pp. 1157-1166.
Shamay et al. Journal of Medicinal Chemistry Published 2009, pp. 5906-5915.
Shamay et al. Biomaterials Published 2009, pp. 6460-6468.
Nan et al. (Journal of Drug Targeting, vol. 13, No. 3, Published Apr. 2005, pp. 189-197).
Jacob GS et al., Studies on selectin-carbohydrate interactions, Adv. Exp. Med. Biol. 1995;376:283-90.
Roy, R., et al, Combined Glycomimetic and Multivalent strategies for the design of potent selectin antagonists, Bioorganic & Medicinal Chemistry Letters, vol. 6, No. 12, pp. 1399-1402, 1996.
Welply et al. "Multivalent sialyl-Lex: potent inhibitors of E-selectin-mediated cell adhesion; reagent for staining activated endothelial cells." Glycobl.ology vol. 4 00. 3 (1994) pp. 259-265.
Int'l Search Report for PCT/IL2011/00413 dated Jan. 20, 2012.
Katayama, et al. (Chem Commun (Camb) 2008, (42): 5399-401).
Dvir T. et al. Nano Lett 2010, 10:250-154.

* cited by examiner

*Primary Examiner* — Alma Pipic
(74) *Attorney, Agent, or Firm* — Cooley LLP; Matthew Pavao; Christine C. Pemberton

(57) ABSTRACT

The site-specific expression of selectins on endothelial cells of blood vessels during angiogenesis provides an opportunity to target anti-cancer drugs to the vascular endothelium to extend the range of the therapeutic effect. This invention describes an innovative drug targeting strategy for the selective delivery of the anticancer drugs to endothelial cells by means of polymer-drug conjugates modified with a carbohydrate ligand for the vascular selectins. A model chemotherapeutic drug, doxorubicin, and the E-selectin ligand, sLex, are attached to a biocompatible polymer (HPMA). The selective binding, cellular uptake, intracellular fate, and cell cytotoxicity of the polymer-bound drug are investigated in human endothelial cells.

20 Claims, 17 Drawing Sheets

Figure 8A | Figure 8C
Non Activated | Activated
6hrs
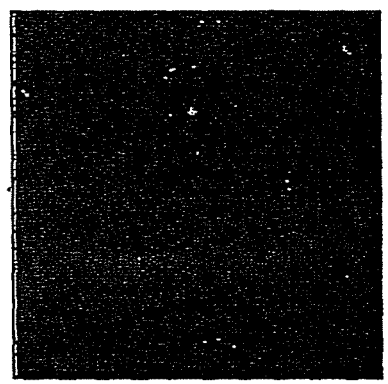 
24hrs
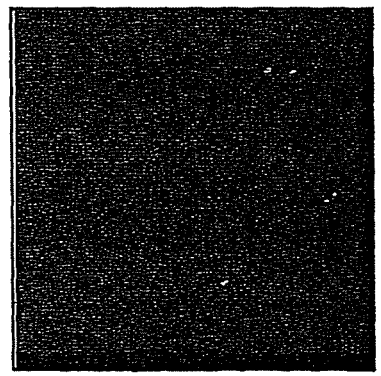 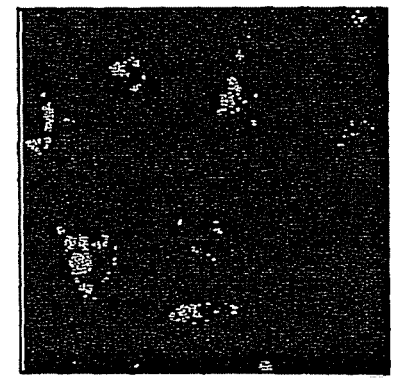
Figure 8B | Figure 8D

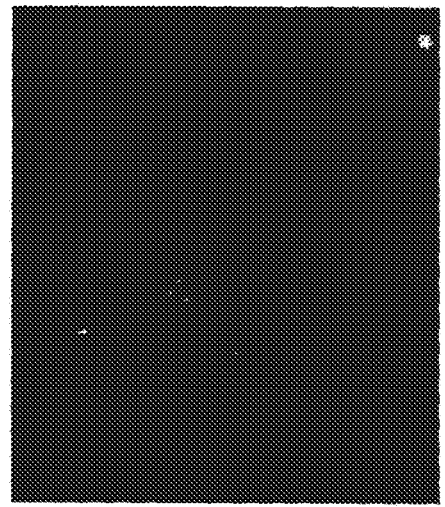
Figure 14A
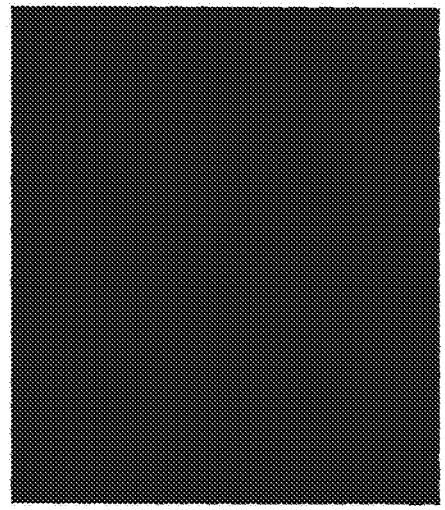
Figure 14B
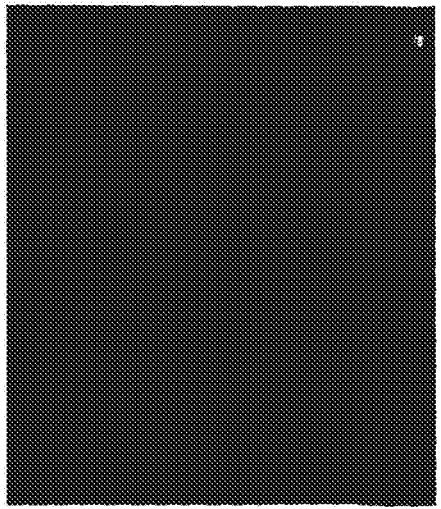
Figure 14C
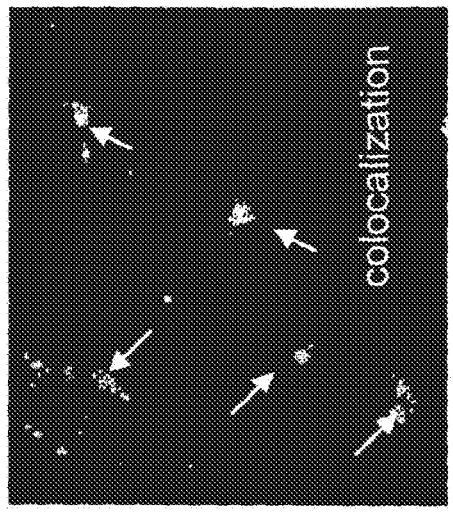
Figure 14D
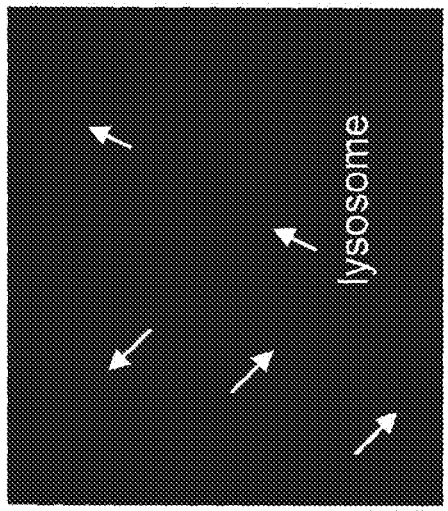
Figure 14E lysosome
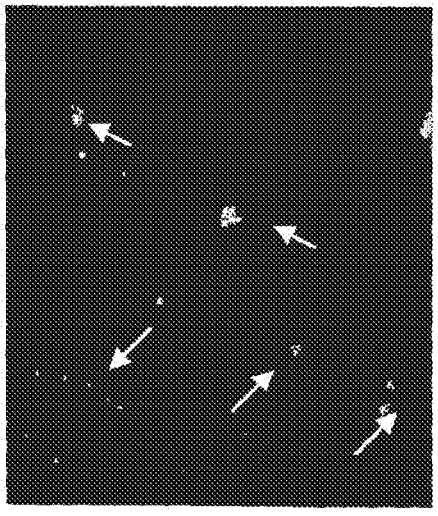
Figure 14F colocalization

SEQUENCE LISTING

```
<160> NUMBER OF SEQ ID NOS: 11

<210> SEQ ID NO 1
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 1

Xaa Xaa Trp Xaa Xaa Leu Trp Xaa Xaa Met Xaa
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
```

```
<400> SEQUENCE: 2

Xaa Xaa Xaa Trp Xaa Xaa Leu Trp Xaa Xaa Met Xaa
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide

<400> SEQUENCE: 3

Asp Ile Thr Trp Asp Gln Leu Trp Asp Leu Met Lys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 4

Xaa Xaa Xaa Xaa Xaa Trp Xaa Xaa Leu Trp Xaa Xaa Met Xaa
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 5

Xaa Xaa Xaa Xaa Xaa Xaa Trp Xaa Xaa Leu Trp Xaa Xaa Met Xaa
1               5                   10                  15
```

```
<210> SEQ ID NO 6
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Xaa can be any naturally occurring amino acid

<400> SEQUENCE: 6

Xaa Xaa Xaa Asp Ile Thr Trp Asp Gln Leu Trp Asp Leu Met Lys
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide

<400> SEQUENCE: 7

Gly Phe Leu Gly Asp Ile Thr Trp Asp Gln Leu Trp Asp Leu Met Lys
1               5                   10                  15

<210> SEQ ID NO 8
<211> LENGTH: 13
<212> TYPE: PRT
<213> ORGANISM: Artificial Sequence
<220> FEATURE:
<223> OTHER INFORMATION: Synthetic peptide

<400> SEQUENCE: 8

Gly Lys Met Ile Asp Trp Thr Trp Leu Gln Leu Asp Asp
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic peptide

<400> SEQUENCE: 9

Gly Asp Ile Thr Trp Asp Gln Leu Trp Asp Leu Met Lys
1               5                   10

<210> SEQ ID NO 10
<211> LENGTH: 4
<212> TYPE: PRT
<213> ORGANISM: Artificial Sequence
<220> FEATURE:
<223> OTHER INFORMATION: peptide spacer

<400> SEQUENCE: 10

Gly Phe Leu Gly
1

<210> SEQ ID NO 11
<211> LENGTH: 13
<212> TYPE: PRT
<213> ORGANISM: Artificial Sequence
```

```
<220> FEATURE:
<223> OTHER INFORMATION: Synthetic peptide

<400> SEQUENCE: 11

Cys Asp Ile Thr Trp Asp Gln Leu Trp Asp Leu Met Lys
1               5                   10
```

VASCULAR DELIVERY SYSTEMS

The present application is a continuation application of U.S. application Ser. No. 12/954,109, filed on Nov. 24, 2010, which is a U.S. National Phase application of International Patent Application No. PCT/IL2009/000152, filed Feb. 11, 2009, which claims priority to U.S. Provisional Application Ser. No. 61/071,461, filed Apr. 30, 2008, each of which is herein incorporated by reference in its entirety for all purposes.

FIELD OF THE INVENTION

The site-specific expression of selectins on endothelial cells of blood vessels during angiogenesis and inflammation provides an opportunity for targeting anti-cancer and anti-inflammatory drugs to the vascular endothelium to extend the range of the therapeutic effect. This invention describes a drug targeting strategy for the selective delivery of anti-cancer and anti-inflammatory drugs or diagnostic agents to endothelial cells by means of polymer-drug conjugates modified with a carbohydrate ligand for vascular selectins.

BACKGROUND OF THE INVENTION

A growing body of evidence indicates that angiogenesis is essential to the progression of cancer. Angiogenesis is the sprouting of new capillaries from preexisting blood vessels. Normally, angiogenesis in mammals is confined to the reproductive system, embryogenesis and development, and repair after injury. Angiogenesis can also occur, however, in pathological conditions such as cancer, retinal neovascularization, neovascularization in atherosclerotic plaques, hemangiomas, arthritis, and psoriasis. Without vascularization, tumors may remain for years as small (less than a few millimeters) asymptomatic lesions. Angiogenesis allows the cancerous cells access to the circulatory system. The new blood vessels provide a gateway for cancer cells to enter the circulation and metastasize to distant sites.

Site specific expression of E-selectin on endothelial cells occurs during cancerous and inflammatory conditions, and may represent an early stage in the pathogenesis of these conditions.

Tumor vascular drug-targeting strategies aimed at blocking the tumor blood flow have enormous therapeutic potential in inhibiting tumor growth and reducing tumor mass. Current methods of cancer therapy that focus on the vascular needs of the tumor have relied on the use of anti-angiogenic factors, which prevent the formation of new blood vessels and inhibit new tumor growth in regions of neovascularization. This approach, however, does little to eliminate areas in existing tumors where mature vessels supply adequate circulation or peripheral regions of tumors that share vascularization with adjacent normal tissues.

There remains a need for effective targeting of existing tumor vasculature and thereby an effective cancer therapy, as well as targeting effective therapeutics to other diseases associated such as inflammatory conditions involving the selectins.

SUMMARY OF THE INVENTION

In one embodiment this invention provides a polymer characterized by the structure of formula 1:

$$P\text{-}(A)_m \quad \quad 1$$

wherein m indicates percentage of the respective monomer composition of the polymer, wherein m is between about 0.05%-50%;

A is a quinic acid (QA), fucose or sialyl Lewis X (sLe$^x$) derivatives characterized by the structure of formula Ia, Ib, or Ic,

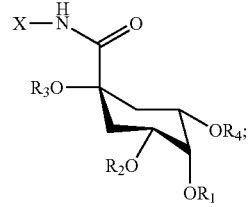

Formula Ia

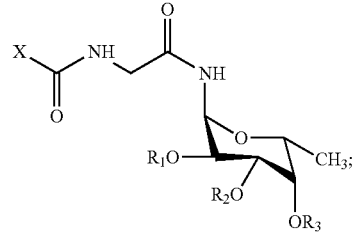

Formula Ib

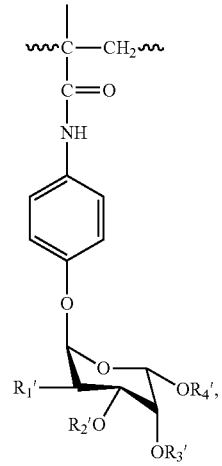

Formula Ic respectively or any combination thereof;

$R_1$, $R_2$, $R_3$ and $R_4$ are independently H, $(C_1\text{-}C_6)$alkyl, aryl, acetyl, sugar chain, protein or a synthetic polymer;

$R_1'$ is H, $(C_1\text{-}C_6)$ alkyl, aryl, acetyl, amide, sugar chain, protein or a synthetic polymer; and $R_2'$, $R_3'$ and $R_4'$ are independently H, $(C_1\text{-}C_6)$ alkyl, aryl, acetyl, saccharides, polypeptides, protein, protein conjugates, or a synthetic polymer;

X is a peptide group with —COOH ending side chain represented by the structure of formulae IIa, IIb, IIc or IId:

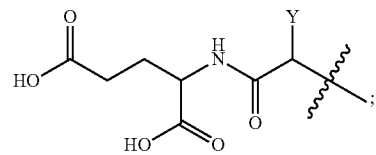

Formula IIa

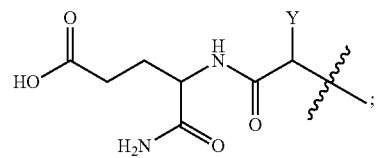

Formula IIb

-continued

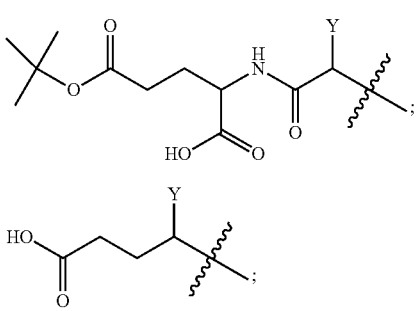

Formula IIc or

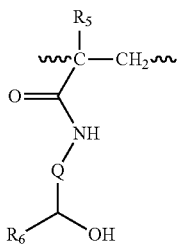

Formula IId

Y is a spacer arm used to link the targeting moiety to the polymeric backbone, wherein said spacer arm is an alkane, alkene or a peptidic chain of 6 to 12 atoms; and P is a polymeric group comprising underivatized or derivatized monomers of N-(2-hydroxypropyl)methacrylamide (HPMA), N-methylacrylamide, N,N-dialkylacrylamides, acrylic acid, methacrylic acid, polyamino acids, polysaccharides, polymers containing polyethyleneoxide sequences and polyvinyl pyrrolidone-maleic anhydride polymers, polylactic-co-glycolic acid, dendrimers, saccharides, peptides, proteins, polymer-peptide conjugates and polymer-protein conjugates.

In one embodiment P is characterized by the monomer represented by the structure of formula:

$$\begin{array}{c} R_5 \\ | \\ \text{\textasciitilde\textasciitilde\textasciitilde} C - CH_2 \text{\textasciitilde\textasciitilde\textasciitilde} \\ | \\ O = \\ | \\ NH \\ | \\ Q \\ | \\ R_6 \quad OH \end{array}$$ IV wherein Q is a ($C_1$-$C_6$) alkyl;

$R_5$ is H, phenyl, halogen, OH, CN, $NO_2$, $NH_2$, ($C_1$-$C_6$) alkyl, acetyl or benzyl; and $R_6$ is H, phenyl or ($C_1$-$C_6$) alkyl.

In one embodiment, this invention provides a polymer characterized by the structure of formula 2:

$$P\text{-}(A)_m\text{-}(B)_q\text{-}(C)_t \quad 2$$

wherein m, q and t indicate percentage of the respective monomer composition of the polymer, wherein m is between about 0.05%-50%, q is between about 0 to 25% and t is between 0 to 25%; wherein at least one of q or t is not 0.

A, Y. P. X, $R_1$, $R_2$, $R_3$, $R_4$, $R_1'$, $R_2'$, $R_3'$ and $R_4'$ is as defined hereinabove;

B is a an antineoplastic agent optionally comprises a spaces; and

C is an imaging agent optionally comprises a spacer.

In another embodiment, this invention provides a polymer characterized by the structure of formula 3:

$$P\text{-}(Y\text{-}J)_m \quad 3$$

wherein m indicates percentage of the respective monomer composition of the polymer, wherein m is between about 0.05%-50%;

J is a peptide targeting moiety having a sequence corresponding to that set forth in SEQ ID NOs: 1-7 or 9;

Y is a spacer arm linking the targeting moiety to the polymeric backbone, wherein said spacer arm is an alkane, alkene or a peptidic chain of 6 to 18 atoms; and P is a polymeric group comprising underivatized or derivatized monomers of N-(2-hydroxypropyl)methacrylamide (HPMA), N-methylacrylamide, N,N-dialkylacrylamides, acrylic acid, methacrylic acid, polyamino acids, polysaccharides, polymers containing polyethyleneoxide sequences and polyvinyl pyrrolidone-maleic anhydride polymers, polylactic-co-glycolic acid, dendrimers, saccharides, peptides, proteins, polymer-peptide conjugates or polymer-protein conjugates.

In some embodiments, according to this aspect, the polymer is further characterized by the structure of formula 4:

$$P\text{-}(Y\text{-}J)_m\text{-}(B)_q\text{-}(C)_t \quad 4$$

Wherein m, q and t indicate percentage of the respective monomer composition of the polymer, wherein m is between about 0.05%-50%; q is between about 0 to 50%; t is between 0 to 50%; wherein q and t cannot simultaneously be 0;

B is a an antineoplastic agent optionally comprising a spacer; and

C is an imaging agent optionally comprising a spacer.

In some embodiments, according to this aspect, the monomer B or C is characterized by the formula: —(CHR—$CH_2$)—, wherein R is a drug or a tag, optionally comprising a spacer.

In some embodiments, according to this aspect, the spacer is a peptide, an alkane or an alkene and in some embodiments, the peptide is Gly-Phe-Leu-Gly_SEQ ID NO: 10.

In some embodiments, according to this aspect, the molar percent composition of B is about 80 percent of the polymer and the molar percent composition of J is about 20 percent of the polymer.

In some embodiments, according to this aspect, the antineoplastic agent is doxorubicin (DOX).

In one embodiment this invention provides a pharmaceutical composition comprising a polymer of this invention.

In one embodiment this invention provides a method of treating an inflammatory condition in a subject, the method comprising administering a polymer of this invention to a subject.

In one embodiment this invention provides a method of treating, reducing the incidence of, delaying progression of, reducing the pathogenesis of, prolonging remission of cancer or inhibiting metastasis of a cancer in a subject, the method comprising the step of contacting a neoplastic cell or vasculature associated with a neoplastic cell in a subject with a polymer of this invention.

In one embodiment the polymer binds a receptor expressed on the surface on a neoplastic cell. In one embodiment the receptor is a selectin.

In one embodiment this invention provides a method of diagnosing cancer in a subject, the method comprising contacting a polymer of this invention with a neoplastic cell, or with vasculature associated with a neoplastic cell in a subject. In one embodiment diagnosis comprises the detection of a tag moiety incorporated in the polymers of the present invention.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

The percentage of bound HL-60 cells is determined with o-phenylenediamine as a substrate for myeloperoxidases released from lysed cells. FIG. 3A depicts binding in the presence of $sLe^x$ and MAP-Glu-Gly-QA monomers. FIG. 3B depicts binding in the presence of P-Glu-Gly-QA, $PAAsLe^x$ and pHPMA polymers; FIG. 3C depicts binding of P-Glu-Gly-QA and P-Gly-Gly-Lys(Glu)-QA conjugates.

Figure 4:
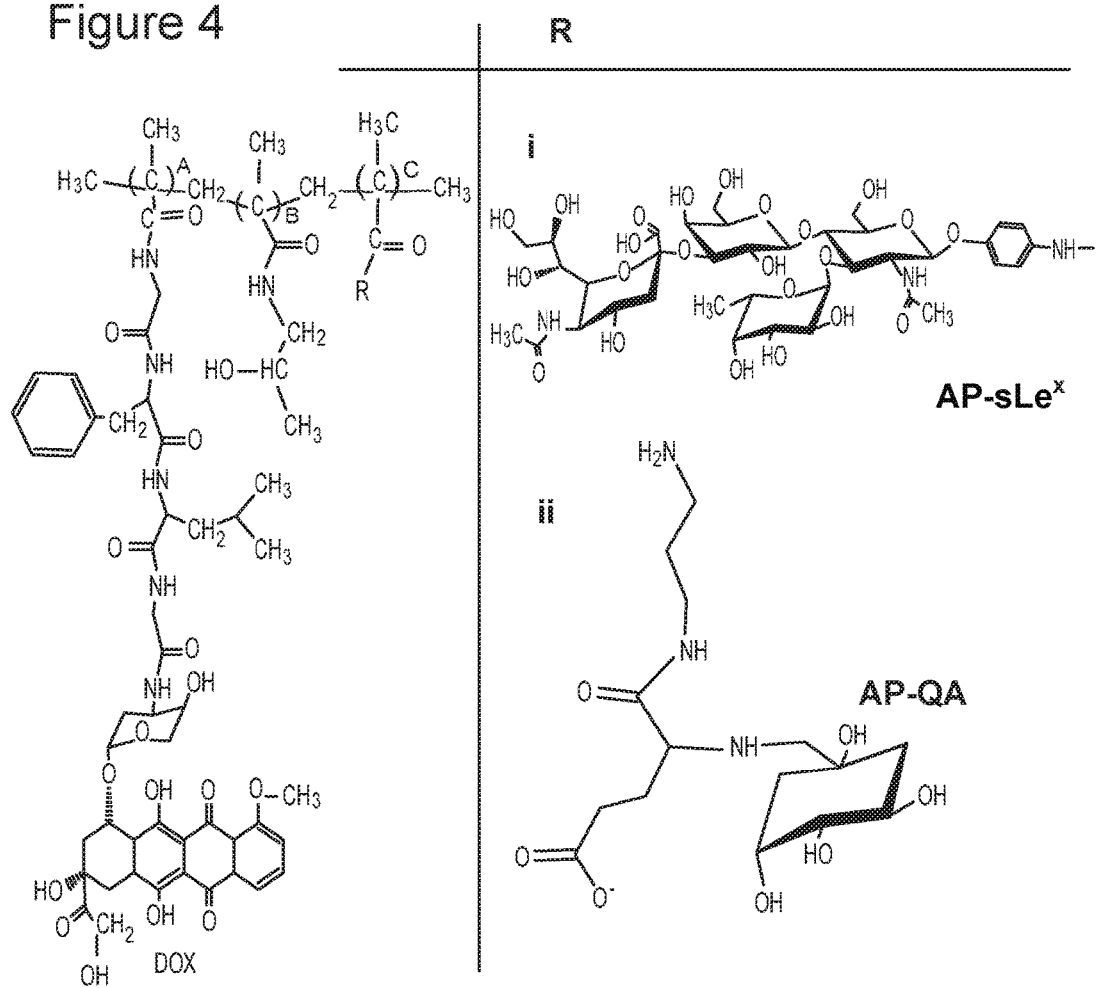

P-Gly-Gly-Lys(Glu)-QA, terminated with the dicarboxyl side chain, has binding potency equal to that of P-Glu-Gly-QA. P-Gly-Gly-Lys(Glu)-QA, upward diagonal bars; P-Glu-Gly-QA, dotted bars; HPMA, solid blue bars; free $sLe^x$, dark horizontal bars;

FIG. 4 shows the synthesis of MA-Gly-Phe-Leu-Gly-DOX. The drug-containing monomer is prepared. A lysosomally degradable glycylphenylalanylleucylglycine (Gly-Phe-Leu-Gly, SEQ ID NO: 10) spacer is used as the oligopeptide side chain. The targeted polymer drug conjugate ($P-sLe^xDOX$) is prepared by polymerizing $MAP-sLe^x$ and the doxorubicin-containing monomer (MAGly-Phe-Leu-Gly-DOX) with HPMA under the same conditions as mentioned above. Likewise, the monomers MA-AP-QA and MA-Gly-Phe-Leu-Gly-DOX are employed as monomers to prepare P-QA-DOX. In the figure, A represents the Doxorubicin content; B represents the HPMA content and C represents the sLex or QA side chain content; $AP-sLe^x$=AminophenylsLe$^x$ and AP-QA=Aminopropylthioureidyl-γ-glutamyl-QA.

Figure 5:
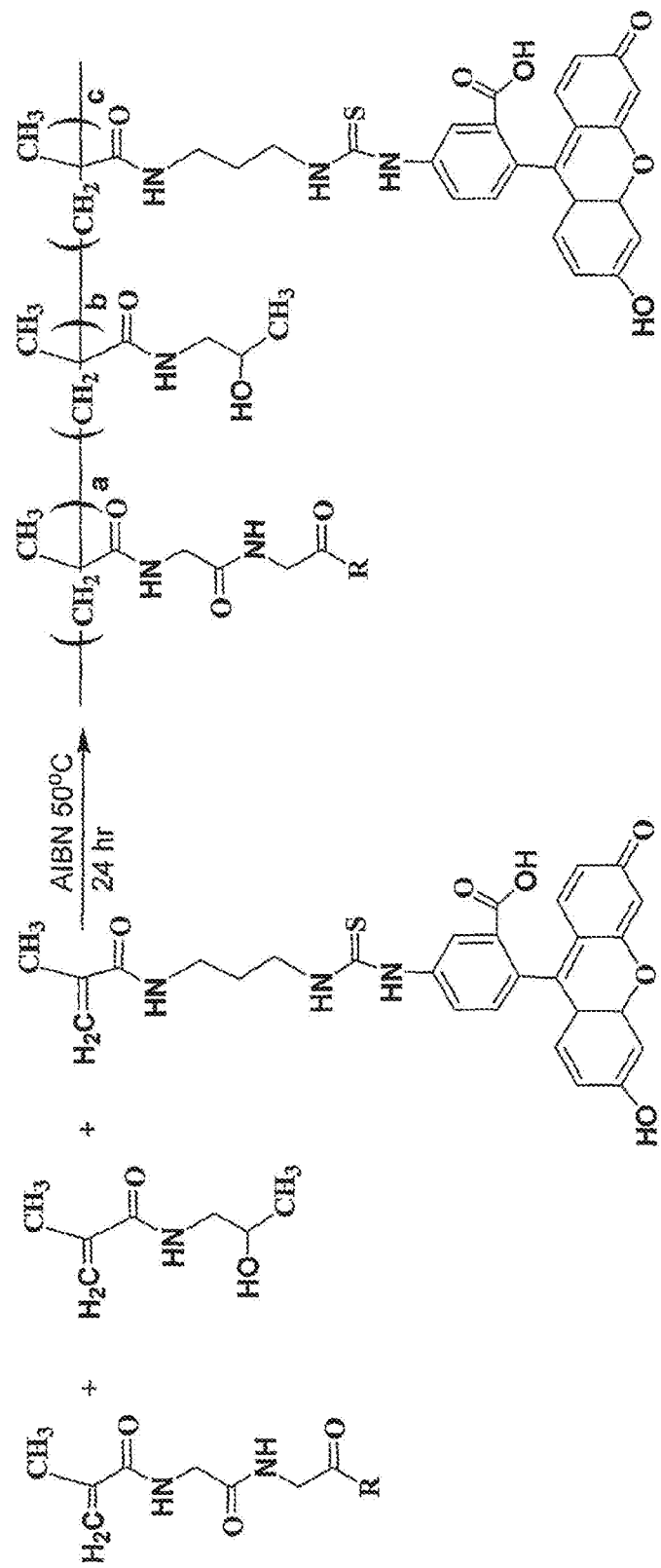

FIG. 5 shows the synthesis and characterization of HPMA polymer conjugates. The fluorescently labeled polymer ($P-sLe^x$-FITC, without drug) is synthesized by polymerizing the $sLe^x$ monomer ($MAP-sLe^x$) and the FITC-labeled monomer (MA-AP-FITC) with HPMA in acetone/DMSO, with 2,2'-azobis(isobutyronitrile) (AIBN) as the initiator.

Figure 6A:
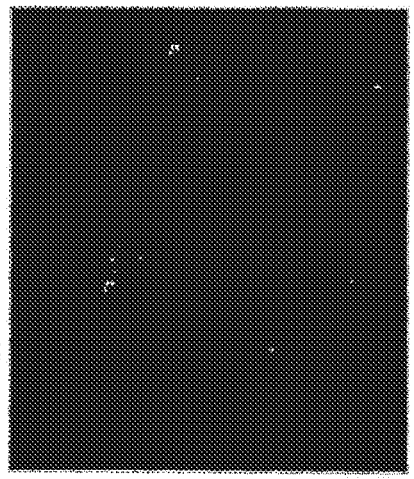
Figure 6B:
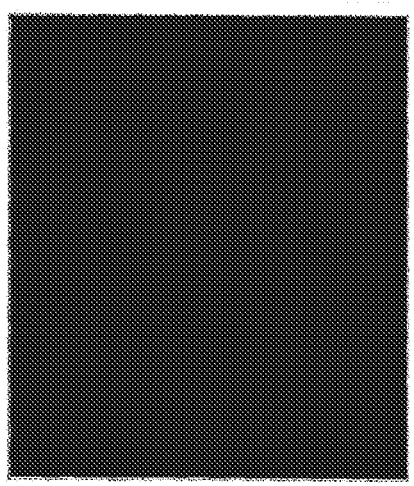
Figure 6C:
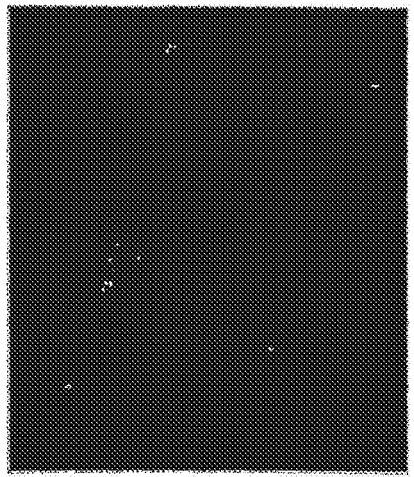
Figure 6D:
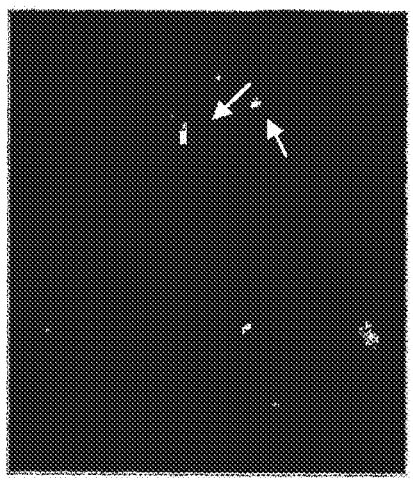
Figure 6E:
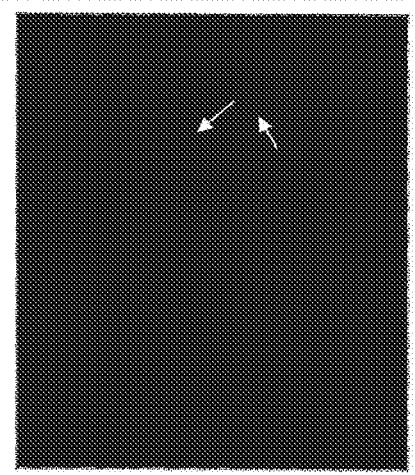
Figure 6F:
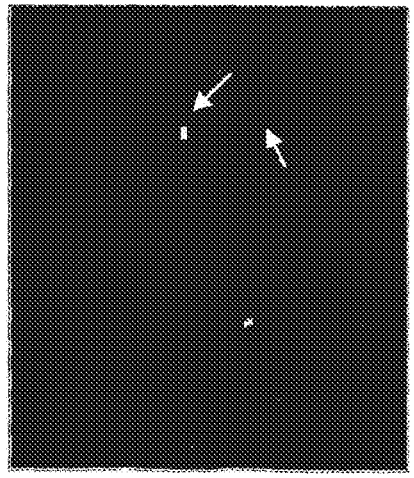

FIG. 6A-F shows the co-localization of P-Qa conjugates and the lysosomal markers indicates the lysosomotropism in E-selectin expressing cells (human IVECs). Cells incubated with PGGOH at a concentration of 50 μg/ml for 24 hr (FIG. 6A-C) when imaged for FITC fluorescence (which was a tag for the conjugate) and LysoTracker Red DND-99 (a lysosomal marker) showed no appreciable colocalization of the signals when merged, in contrast to similarly probed cells treated with P-GG-Lys-(GluCONH2)-Qa at a concentration of 50 μg/ml, for 24 hr (FIG. 6D-F).

Figure 7A:
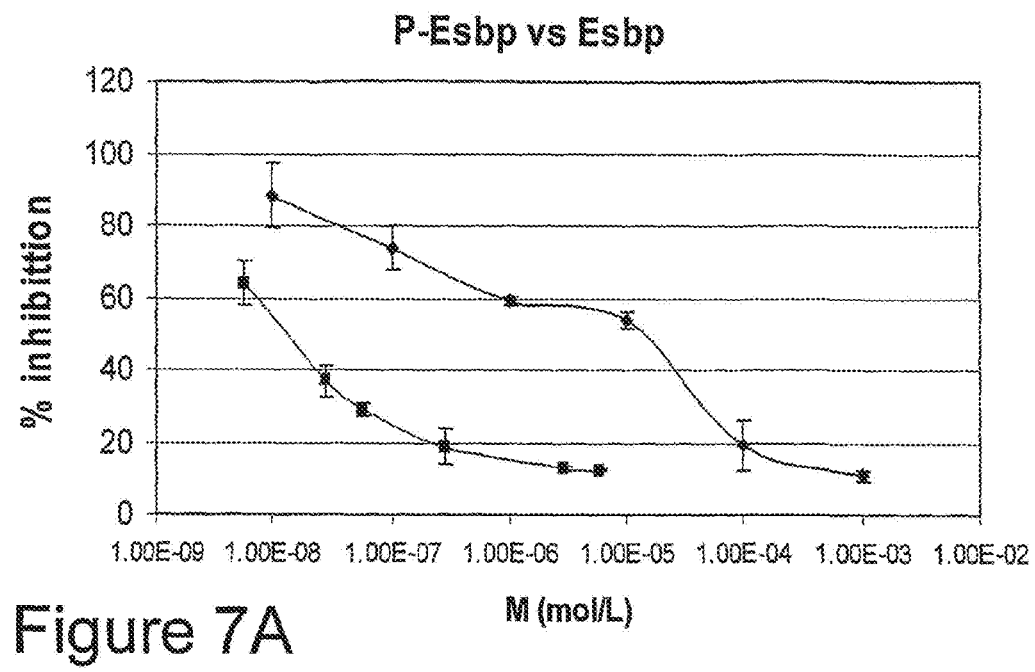
Figure 7B:
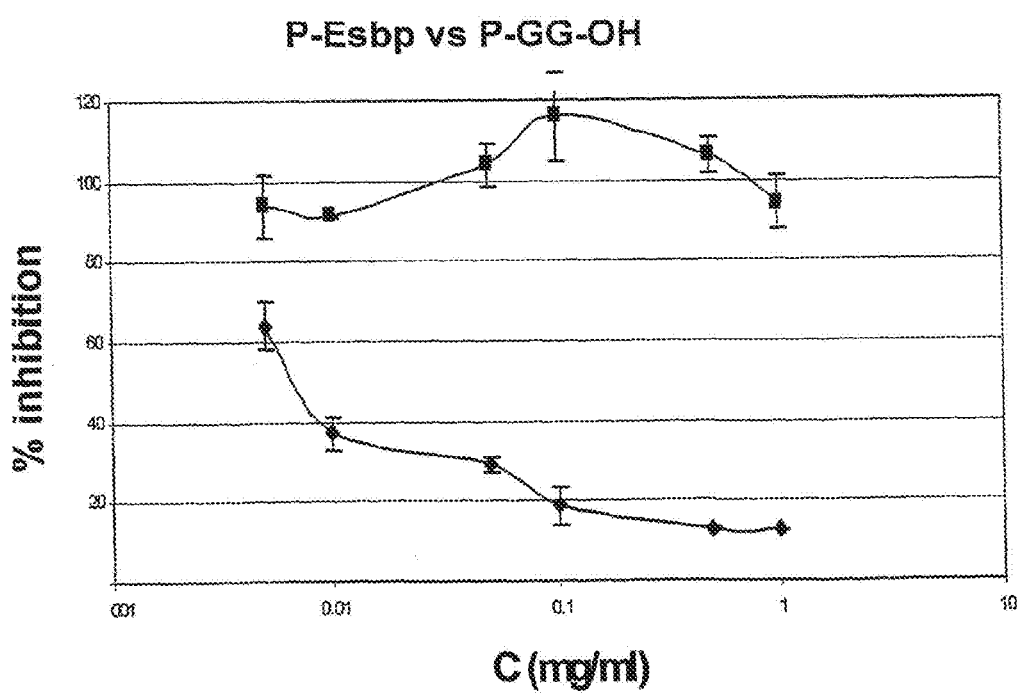
Figure 9A:
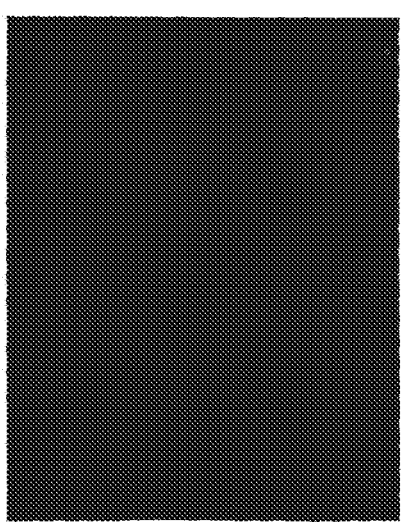
Figure 9B:
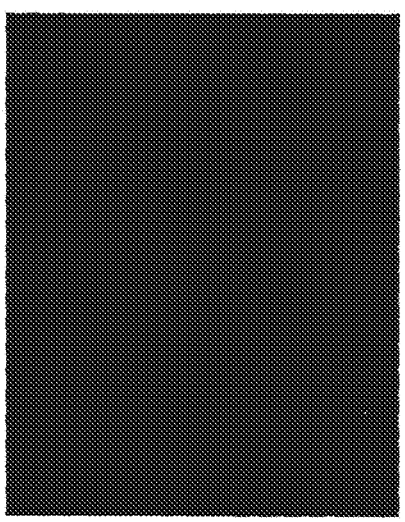
Figure 9C:
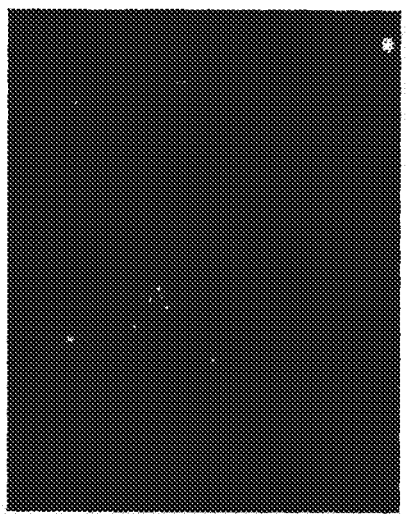
Figure 9D:
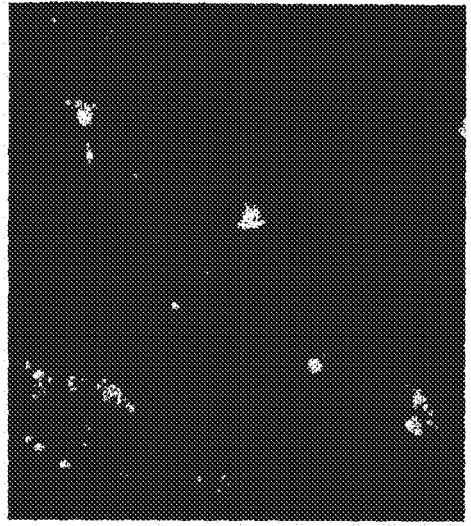
Figure 9E:
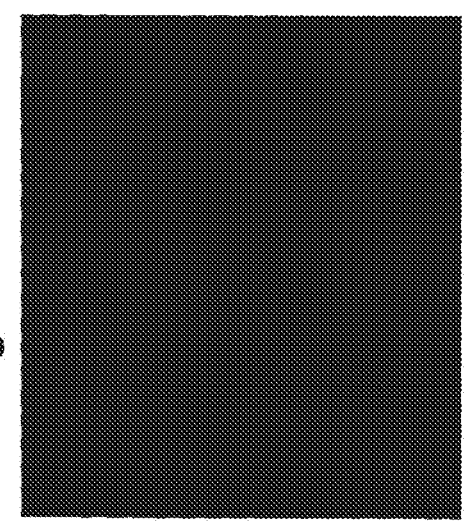
Figure 9F:
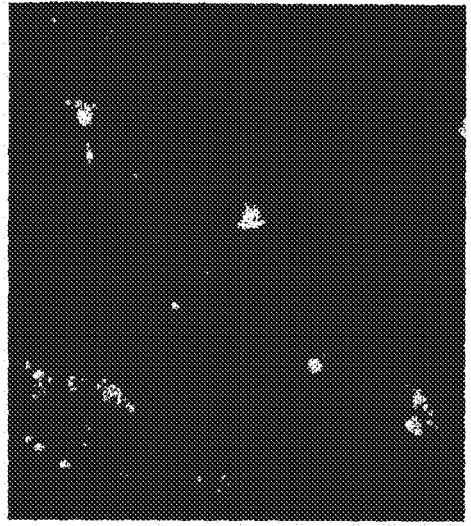

FIG. 7A shows the results of an inhibition assay with P-Esbp and Esbp. Affinity of Esbp and P-Esbp to E-selectin was evaluated by a competitive inhibition assay of HL-60 to immobilized E-selectin. Esbp monomer had IC50 of 10 μM and its copolymer conjugate, P-Esbp had IC50 of 20 nM an increase of 3 orders of magnitude (diamonds are Esbp and squares are P-Esbp). FIG. 7B the results of an inhibition assay with P-Esbp and P-GG-OH, under the same procedure as in FIG. 7A. In this figure diamonds are P-Esbp and squares are P-GG-OH.

FIG. 8A-D depicts micrographs obtained by Confocal Microscopy of IVECs incubated with FITC labeled P-Esbp. The cells were treated (FIG. 8C or FIG. 8D) or not treated (FIG. 8A or FIG. 8B) with TNFα and FITC labeled P-Esbp solution for 6 hr (panel 1) or 24 hr (panel 2).

FIG. 9A-F depicts micrographs obtained by Confocal Microscopy of FITC-labeled copolymer P-Esbp uptake by IVECs. Activated IVECs (FIGS. 9D, E & F) and non activated IVECs (FIGS. 9A, B & C) were incubated with 50 μg/ml P-Esbp for 15 hr. The green color (A and D) indicates FITC-labeled copolymer (P-Esbp), red color (B and E) indicates lysosomal compartments, yellow color in the merging of both channels (C and F) indicates FITC-labeled copolymer in the lysosomal compartments. Significant colocalization was observed in activated cells.

Figure 10:
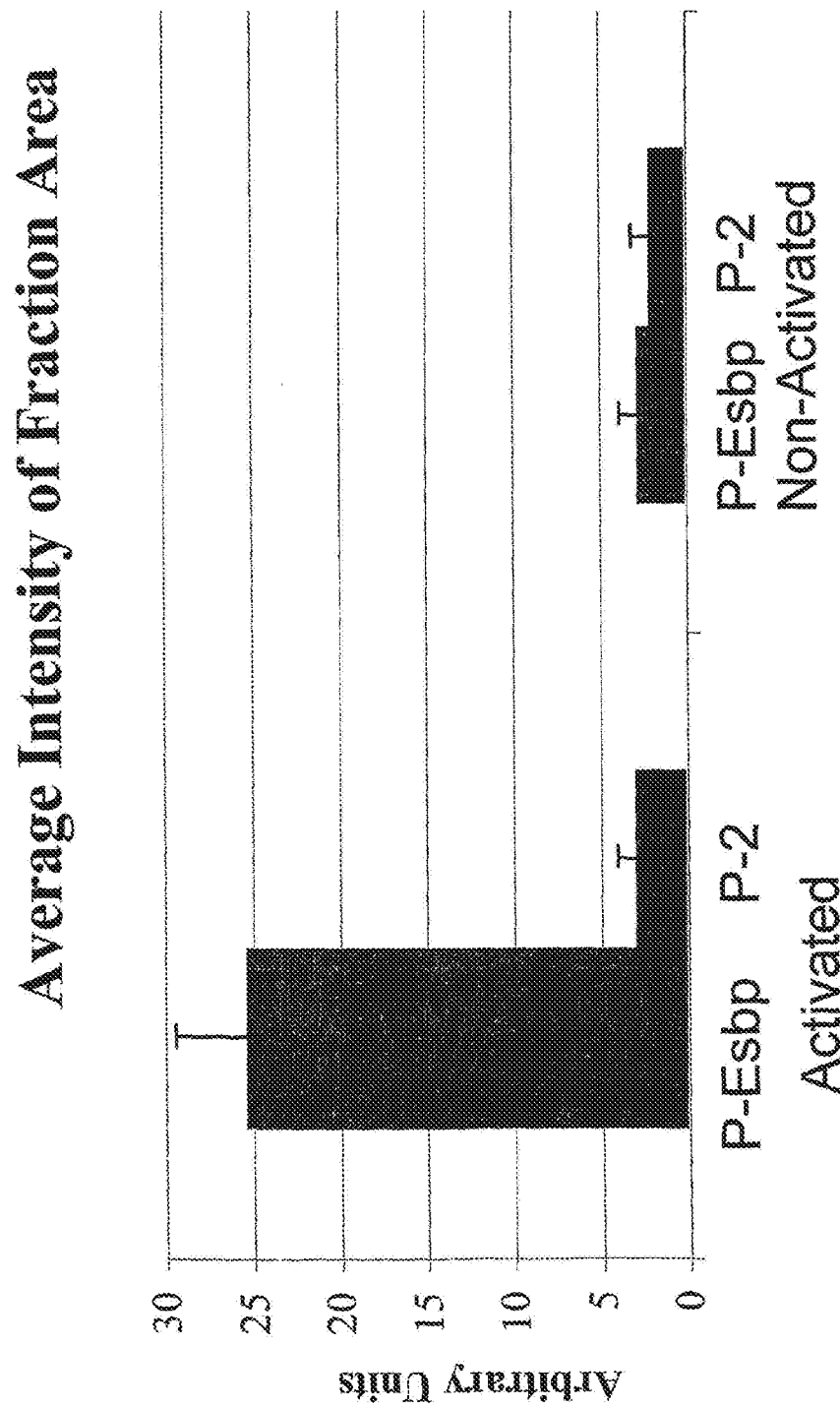

FIG. 10 is a plot of the average fluorescence intensity of fraction area of P-Esbp and P2 as calculated using ImageJ v1.40G software. The data represents an average of 30 different images for each experiment.

Figure 11A:
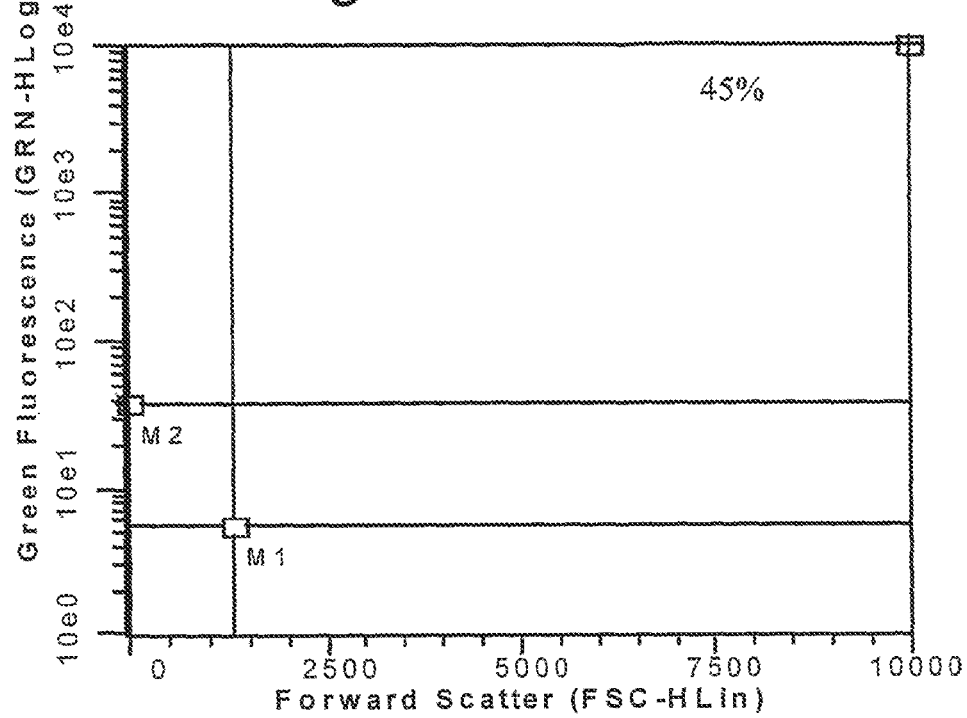
Figure 11B:
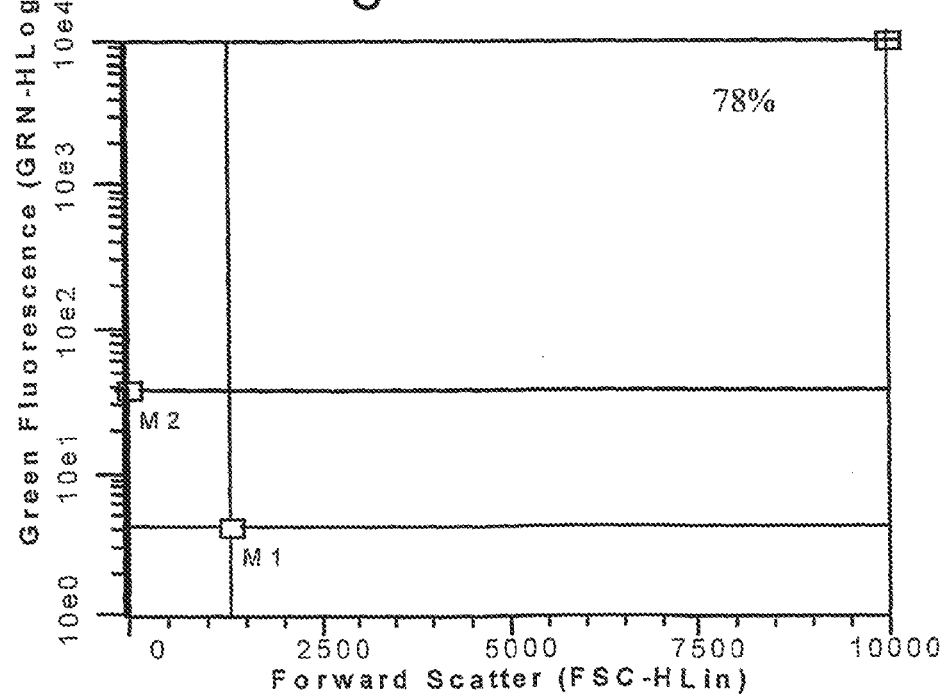
Figure 11C:
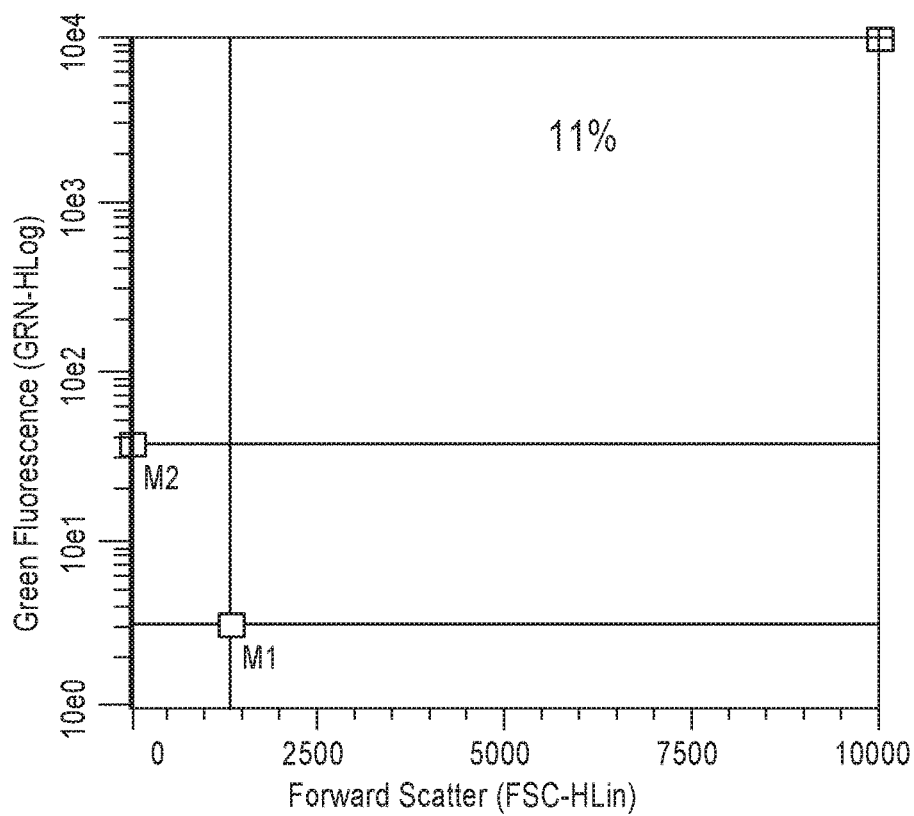
Figure 11D:
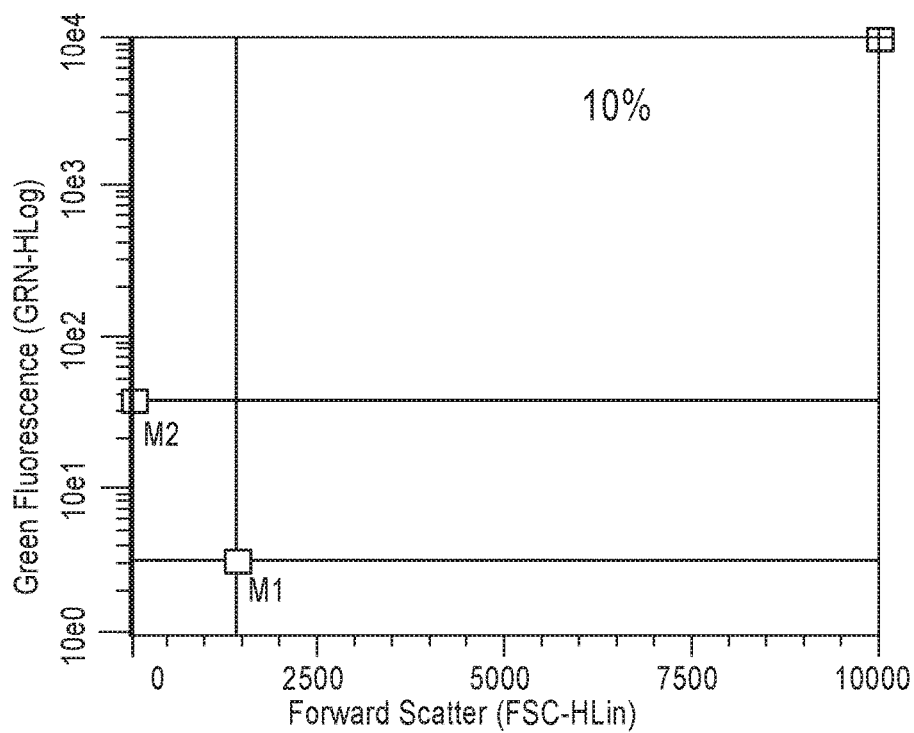
Figure 11E:
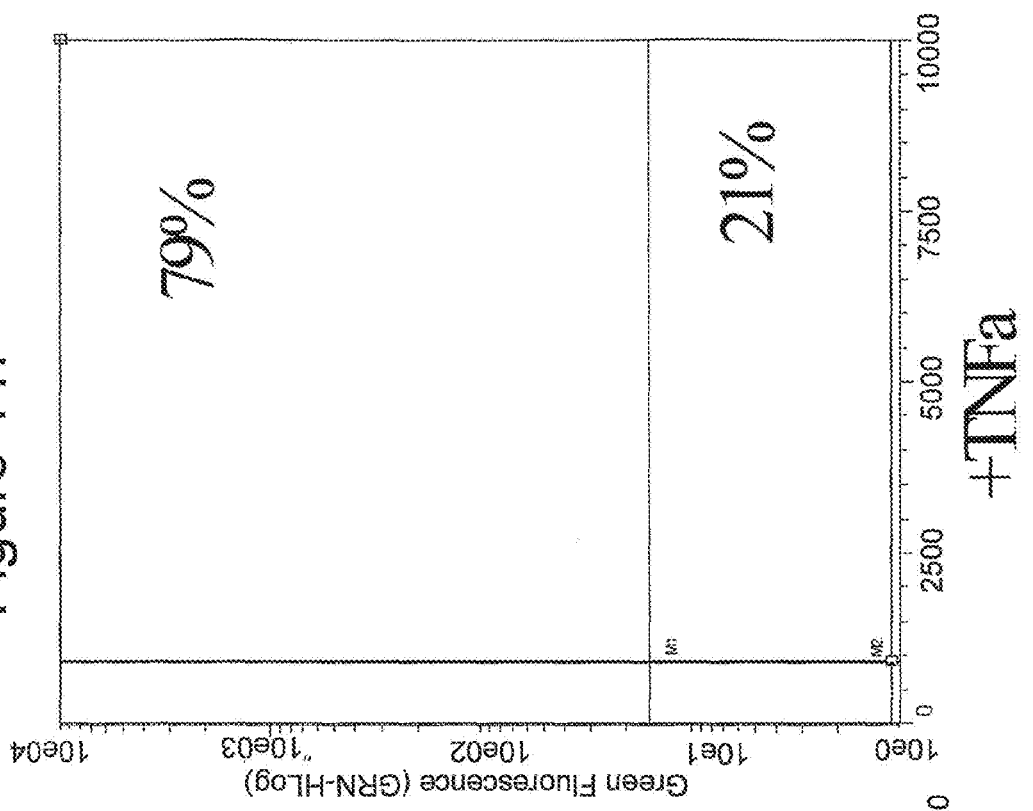
Figure 11F:
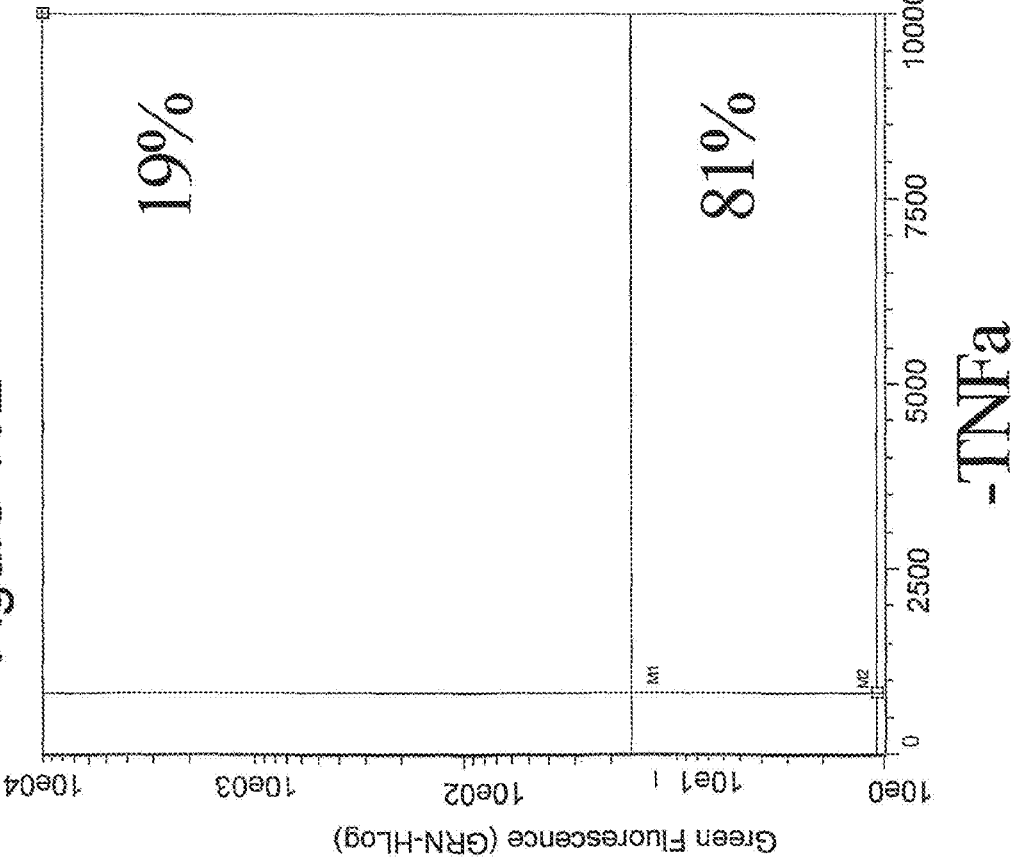
Figure 12A:
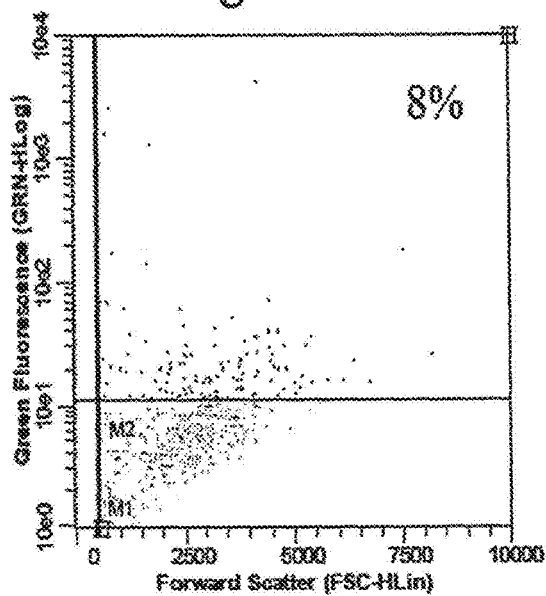
Figure 12B:
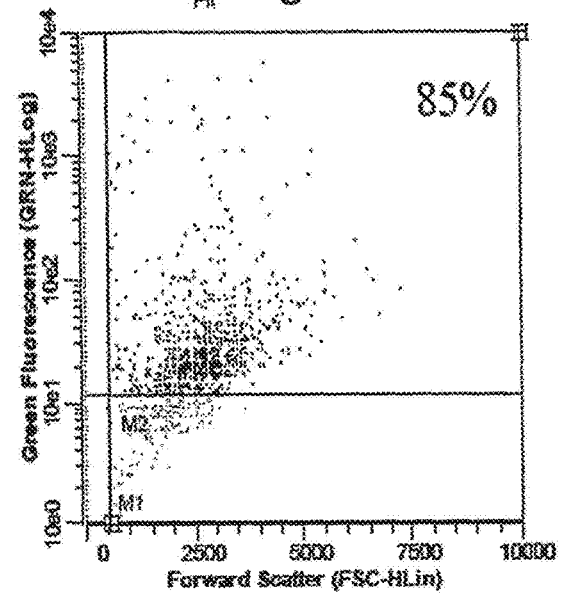
Figure 12C:
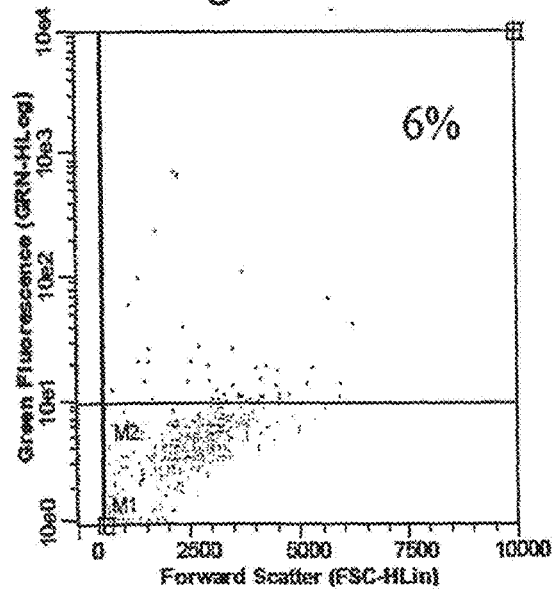
Figure 12D:
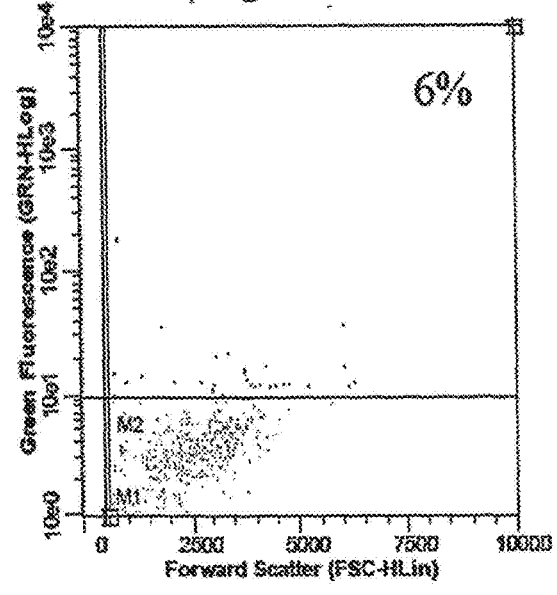

FIG. 11A-F depicts the results of flow cytometry assays of IVECs incubated with P-Esbp at different temperatures. FIGS. 11(A)-(D) depict results of IVECs incubated 4° C. for 1 hour, while FIGS. 11(E)-(F) depict results of IVECs incubated 37° C. for 15 hr in activated (F) and non-activated (E) cells. FIGS. 11A and 11B show results of incubation with P-Esbp at a concentration of 10 and 50 μg/ml, respectively in TNF-α activated cells, versus 11C and D, which show the results of non-activated cells incubated with the same concentration of P-Ebsp, respectively. Fluorescence, size and number of cells were all measured with GUAVA Tech-Mini Easycyte at 520 nm. Statistical analysis of the results was performed with Cytosoft software (GUAVA Tech). Gates for size and fluorescence were set according to the control experiment with P-GG-OH incubated with non activated IVEC cells.

FIG. 12A-D shows binding plots of P-Esbp and scrambled P-scrmb peptide sequence polymer conjugates (P-Scrmb) to E-selectin-expressing cells. Non activated cells (12A and C) contacted with P-Esbp and EP-scrmb, respectively were compared to activated cells (12B and D) similarly treated.

FIG. 13A-D shows binding plots of P-Esbp and scrambled Esbp peptide sequence polymer conjugates (P-Scrmb) to E-selectin expressing cells further contacted with free peptides. Non activated cells (13A and data not shown) contacted with P-Esbp and P-scrmb, respectively were compared to activated cells (13B and data not shown) similarly treated. Activated cells were also incubated with free PEsbp and P-scrmb at 25 and 50 μg/ml (13C, D and data not shown, respectively), and non-activated cells were also incubated with 50 μg/ml of P-Esbp (Data not shown).

FIG. 14A-F shows colocalization of P-Esbp in lysosomal compartments of IVEC cells by confocal microscopy. Non-activated (Figure A-C) and Activated (Figures D-F) were visualized to determine the localization of the conjugates in FIGS. 14A and 14D relative to that of the lysosomal compartments in FIGS. 14B and 14E. Colocalization of the signals can be seen in FIG. 14C (non-activated cells) and FIG. 14F (activated cells).

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The site-specific expression of selectins (E- and P-Selectin) on endothelial cells of blood vessels during inflammatory response and angiogenesis provides an opportunity to target anti-inflammatory, anti neoplastic or imaging agents to the vascular endothelium of diseased tissues. The selective attachment of the selectin ligand sialyl Lewis X (sLe$^x$) and its non-carbohydrate analogs to E- and P-selectin makes them an attractive target for local delivery of therapeutics and diagnostic agents to disease conditions involving the selectins. E-selectin, found on inflamed and angiogenic, but not on normal, blood vessels could be an effective target to selectively deliver drugs and imaging probes to the vasculature of diseased tissues. This invention thus describes, inter alia, an innovative drug targeting strategy for the selective delivery of the drugs and imaging agents to endothelial cells by means of polymer-drug or polymer-imaging probe conjugates modified with multiple carbohydrate (sLe$^x$ or fucose) and non-carbohydrate (QA based) analogs of sLe$^x$ for the vascular selectins.

E-selectin (also known as ELAM-I, CD62, and CD62E) is a cytokine-inducible cell surface glycoprotein that is found on endothelial cells. E-selectin is expressed in vascular endothelial tissue (Pober et al., J. Immunol., 136: 1680 (1986); Bevilacqua et al., Proc. Natl. Acad. ScL 84:9238 (1987)), and is induced in response to the cytokines IL-I and TNF, as well as bacterial lipopolysaccharide (LPS), through transcriptional up-regulation. (Pobor et al., supra; see also, Montgomery et al., Proc. Natl. Acad. ScL 88:6523 (1991)). E-selectin is also a cell adhesion molecule that mediates the adhesion of various leukocytes, including neutrophils, monocytes, eosinophils, natural killer (NK) cells, and a subset of T cells, to activated endothelium (Bevilacqua et al, Science, 243: 1 160 (1989); Graber et al., J. Immunol., 145:819 (1990); Carlos et al. Blood, 77:2266 (1991); Hakkert et al, Blood, 78:2721 (1991); and Picker et al. Nature, 349:796 (1991)). Like other selectins, it plays an important part in inflammation. During inflammation, E-selectin plays an important part in recruiting leukocytes to the site of injury.

In some embodiments of this invention, the compounds and methods of this invention exploit the site-specific expression of E-selectin on endothelial cells for the targeting of certain drugs and diagnostic agents to associated diseased tissues.

In one embodiment this invention provides a polymer characterized by the structure of formula 1:

$$P\text{-}(A)_m \qquad 1$$

wherein m indicates percentage of the respective monomer composition of the polymer, wherein m is between about 0.05%-50%;

A is a quinic acid (QA), fucose or sialyl Lewis X (sLe$^x$) derivatives characterized by the structure of formula Ia, Ib, or Ic,

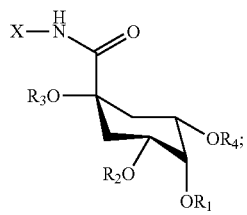

Formula Ia

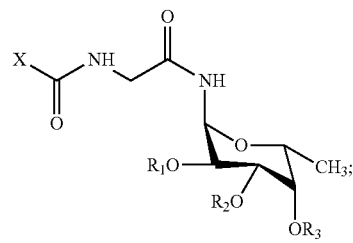

Formula Ib

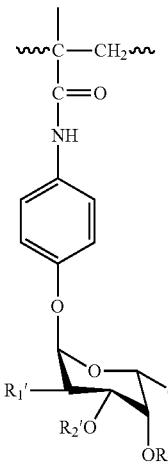

Formula Ic respectively or any combination thereof;

$R_1$, $R_2$, $R_3$ and $R_4$ are independently H, $(C_1\text{-}C_6)$alkyl, aryl, acetyl, sugar chain, protein or a synthetic polymer;

$R_1'$ is H, $(C_1\text{-}C_6)$ alkyl, aryl, acetyl, amide, sugar chain, protein or a synthetic polymer; and $R_2'$, $R_3'$ and $R_4'$ are independently H, $(C_1\text{-}C_6)$ alkyl, aryl, acetyl, saccharides, polypeptides, protein, protein conjugates, or a synthetic polymer;

X is a peptide group with —COOH ending side chain represented by the structure of formulae IIa, IIb, IIc or IId;

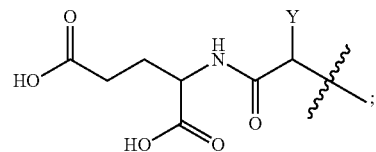

Formula IIa

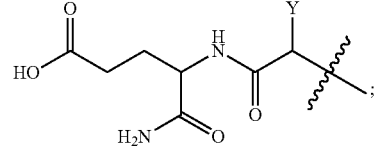

Formula IIb

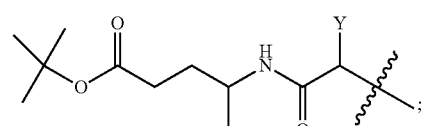

Formula IIc or

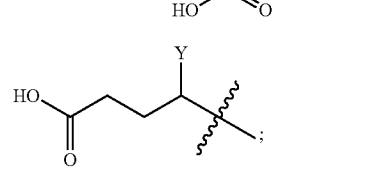

Formula IId

Y is a spacer arm used to link the targeting moiety to the polymeric backbone, wherein said spacer arm is an alkane, alkene or a peptidic chain of 6 to 12 atoms;

P is a polymeric group comprising underivatized or derivatized monomers of N-(2-hydroxypropyl)methacrylamide (HPMA), N-methylacrylamide, N,N-dialkylacrylamides, acrylic acid, methacrylic acid, polyamino acids, polysaccharides, polymers containing polyethyleneoxide sequences and polyvinyl pyrrolidone-maleic anhydride polymers, polylactic-co-glycolic acid, dendrimers, saccharides, peptides, proteins, polymer-peptide conjugates and polymer-protein conjugates. In some embodiments, the polymer is as described above, however A is either Ia or Ib or a combination thereof.

In one embodiment, this invention provides a polymer characterized by the structure of formula 2:

$$P\text{-}(A)_m\text{-}(B)_q\text{-}(C)_t \qquad 2$$

wherein m, q and t indicate percentage of the respective monomer composition of the polymer, wherein m is between about 0.05%-50%, q is between about 0 to 25% and t is between 0 to 25%; wherein at least one of q or t is not 0.

A, Y, P. X, $R_1$, $R_2$, $R_3$, $R_4$, $R_1'$, $R_2'$, $R_3'$ and $R_4'$ is as defined hereinabove;

B is a an antineoplastic agent optionally comprises a spaces; and

C is an imaging agent optionally comprises a spacer.

In one embodiment this invention provides a polymer characterized by the structure of formula 2A:

$$P\text{-}(A)_m\text{-}(B)_q \qquad 2A$$

wherein A, B, P. m and q are as defined for formula 2.

In one embodiment this invention provides a polymer characterized by the structure of formula 2B:

$$P\text{-}(A)_m\text{-}(C)_t \qquad 2B$$

wherein A, C, P, m and t are as defined for formula 2.

In one embodiment the polymer comprises a B or C monomer characterized by the formula: —(CHR—CH$_2$)—, wherein R is a drug or a tag, optionally comprises a spacer. In one embodiment the spacer is a peptide. In one embodiment the peptide is Gly-Phe-Leu-Gly (SEQ ID NO: 10). In one embodiment the drug is doxorubicin (DOX).

In one embodiment P is characterized by the structure of formula IV:

IV wherein

Q is a (C$_1$-C$_6$) alkyl;

R$_5$ is H, phenyl, halogen, OH, CN, NO2, NH$_2$, (C$_1$-C$_6$) alkyl, acetyl or benzyl; and R$_6$ is H, phenyl or (C$_1$-C$_6$) alkyl.

In one embodiment the invention provides a polymer of formula 1-2 wherein the molecular weight of the polymer ranges between 100 Da and 1000 kDa. In one embodiment the molecular weight of the polymer is less than 60 kDa. In one embodiment, the molecular weight of the polymer ranges between 15-40 kDa. It will be appreciated by the skilled artisan that molecular weight may vary as a function of the particular monomers chosen, and that such variations are to be considered as part of this invention.

In one embodiment the composition comprising polymer of formula 1-2 is about 80 molar % of B and about 20 molar % of A.

In another embodiment Y of formula IIa-IIe is characterized by the structure of formulae IIIa, IIIb or IIIc:

IIIa

IIIb

IIIc

In one embodiment formula Ic is represented as follows:

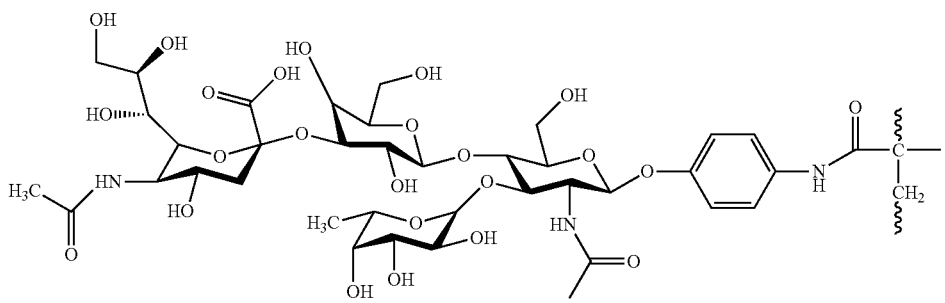

In one embodiment the polymer of formula 2A is represented by the structure of formula VII:

Formula VII

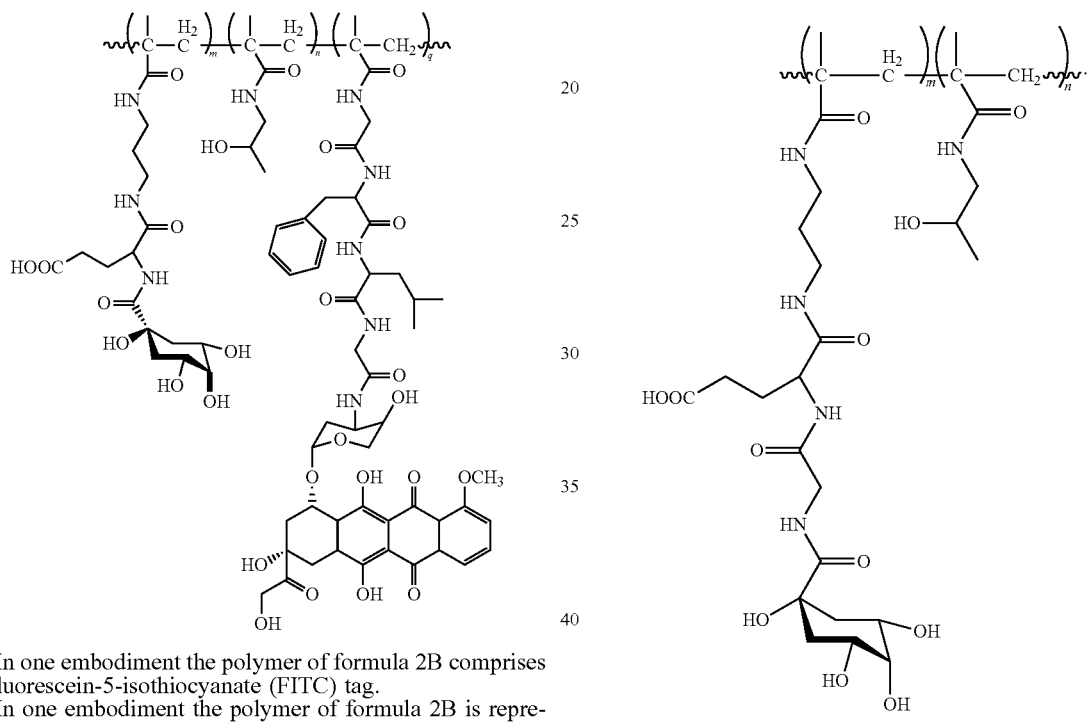

In one embodiment the polymer of formula 2B comprises a fluorescein-5-isothiocyanate (FITC) tag.

In one embodiment the polymer of formula 2B is represented by the structure of formula VIII:

Formula VIII

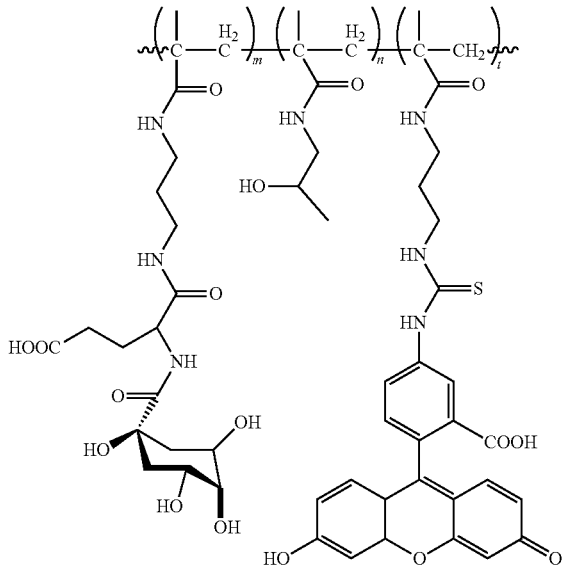

In some embodiments, this invention provides a polymer characterized by the formula IX:

In another embodiment, this invention provides a polymer characterized by the structure of formula 3:

$$P-(Y-J)_m \qquad 3$$

wherein m indicates percentage of the respective monomer composition of the polymer, wherein m is between about 0.05%-50%;

J is a peptide targeting moiety having a sequence corresponding to that set forth in SEQ ID NOs: 1-7 or 9;

Y is a spacer arm linking the targeting moiety to the polymeric backbone, wherein said spacer arm is an alkane, alkene or a peptidic chain of 6 to 18 atoms; and P is a polymeric group comprising underivatized or derivatized monomers of N-(2-hydroxypropyl)methacrylamide (HPMA), N-methylacrylamide, N,N-dialkylacrylamides, acrylic acid, methacrylic acid, polyamino acids, polysaccharides, polymers containing polyethyleneoxide sequences and polyvinyl pyrrolidone-maleic anhydride polymers, polylactic-co-glycolic acid, dendrimers, saccharides, peptides, proteins, polymer-peptide conjugates or polymer-protein conjugates.

According to this aspect and in one embodiment, Y is characterized by the structure of formulae IIIa, or IIIb as follows:

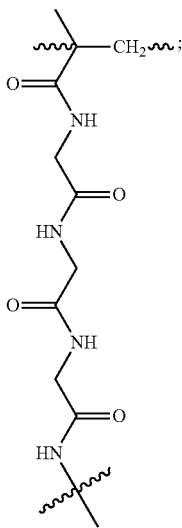

IIIa

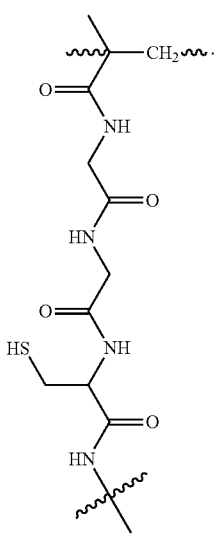

IIIb

According to this aspect and in one embodiment, the molecular weight of the polymer ranges between 100 Da and 1000 kDa, or in some embodiments, the molecular weight of the polymer is less than 60 kDa, or in some embodiments, the molecular weight of the polymer ranges between 15-40 kDa. In some embodiments, the polymer is water soluble.

In some embodiments, according to this aspect, the polymer is further characterized by the structure of formula 4:

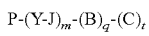　　　　4 wherein m, q and t indicate percentage of the respective monomer composition of the polymer, wherein m is between about 0.05%-50%; q is between about 0 to 50%; t is between 0 to 50%; wherein q and t cannot simultaneously be 0;

B is a an antineoplastic agent optionally comprising a spacer; and

C is an imaging agent optionally comprising a spacer.

In one embodiment this invention provides a polymer characterized by the structure of formula 4A:

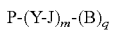　　　　4A wherein J, B, P, m and q are as defined for formula 2.

In one embodiment this invention provides a polymer characterized by the structure of formula 4B:

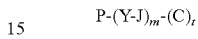

wherein J, C, P. m and t are as defined for formula 2.

In some embodiments, J is a peptide targeting moiety having a sequence corresponding to that set forth in SEQ ID NOs: 1-7 or 9.

| Seq ID No: | Sequence |
|---|---|
| 1 | XXWXXLWXXMX |
| 2 | XXXWXXLWXXMX |
| 3 | DITWDQLWDLMK |
| 4 | XXXXXWXXLWXXMX |
| 5 | XXXXXXWXXLWXXMX |
| 6 | XXXDITWDQLWDLMK |
| 7 | GFLGDITWDQLWDLMK |
| 9 | GDITWDQLWDLMK |

Table 2 describes the sequences corresponding to SEQ ID NOs: 1-7 and 9:

Where W, L and M are the amino acids of tryptophan, leucine, and methionine, respectively and X corresponds to any amino acid.

In some embodiments, according to this aspect, the monomer B or C is characterized by the formula: —(CHR—CH$_2$)—, wherein R is a drug or a tag, optionally comprising a spacer.

In some embodiments, according to this aspect, the spacer is a peptide, an alkane or an alkene and in some embodiments, the peptide is Gly-Phe-Leu-Gly (SEQ ID NO: 10).

In some embodiments, according to this aspect, the molar percent composition of B is about 80 percent of the polymer and the molar percent composition of J is about 20 percent of the polymer.

In some embodiments, according to this aspect, the polymer is represented by the structure of formula VII or VII:

Formula VII

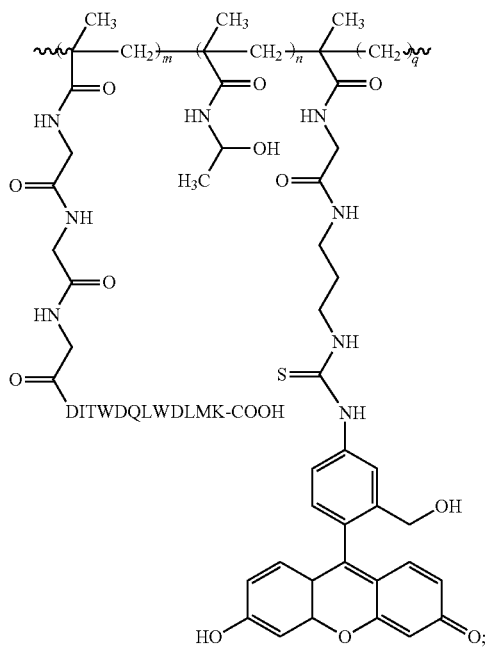

Formula VIII

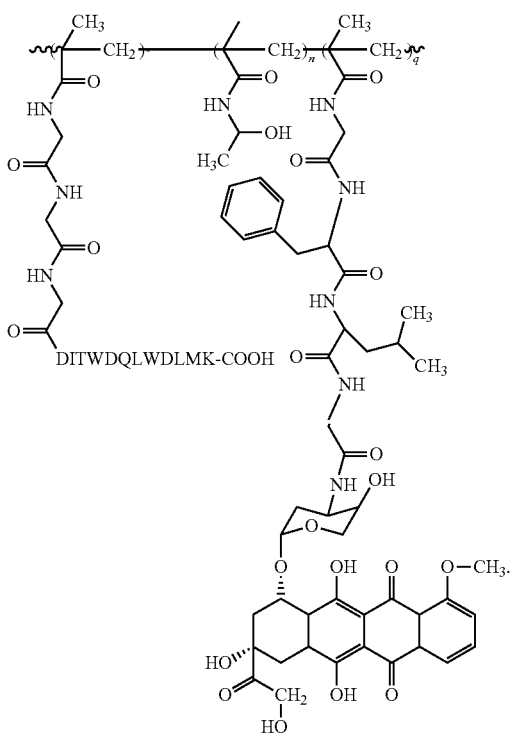

In some embodiments, according to this aspect, m and n are percentages of the monomers, wherein m is between about 0.05%-50% and n is between about 50%-99.95%. In some embodiments, according to this aspect, the imaging agent is fluorescein-5-isothiocyanate (FITC) or indocyanine green.

In one embodiment, with reference to the polymers of this invention, the term "alkyl" refers to $C_{1-6}$ straight-chain or $C_{1-6}$ branched hydrocarbons, e.g. methyl, isobutyl, hexyl, etc. In another embodiment, the term "alkyl" (or "lower alkyl") refers to both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, an amine, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like.

In one embodiment, the term "acetyl" (ethanoyl), is a functional group, the acyl of acetic acid, with the chemical formula —$COCH_3$. In some embodiments, the term "Ac" refers to acetyl.

In one embodiment, the term "aryl" refers to aromatic rings such as phenyl, pyridinyl, thienyl, thiazolyl, or furyl, optionally substituted with one or more groups, such as a halo group, a haloalkyl group, an amino group, or an alkyl group. In one embodiment, the term "aryl" includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more rings in which two or more carbons are common to two adjoining rings (the rings are "fused") wherein at least one of the rings is aromatic, e.g., the other rings can be cycloalkyls, cycloalkenyls, cycloalkenyls, aryls and/or heterocyclyls. In one embodiment, the term "aryloxy" refers to aryl groups attached to a main chain or backbone through an oxygen atom.

In one embodiment, the term "amine" refers to any amine, including primary, secondary, tertiary, quaternary, or a combination thereof, as applicable herein.

In one embodiment, the term "protein" refers to large organic compounds made of amino acids arranged in a linear chain and joined together by peptide bonds between the carboxyl and amino groups of adjacent amino acid residues. In one embodiment the protein is made up of peptide segments. In one embodiment "peptide" refers to native peptides (either degradation products, synthetically synthesized peptides or recombinant peptides) and/or peptidomimetics (typically, synthetically synthesized peptides), such as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), *-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom.

These modifications can occur at any of the bonds along the peptide chain and even at several (2-3) at the same time. Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

In one embodiment, the term "amino acid" or "amino acids" is understood to include the naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" may include both D- and L-amino acids.

Peptides or proteins of this invention may be prepared by various techniques known in the art, including phage display libraries [Hoogenboom and Winter, J. Mol. Biol. 227:381 (1991); Marks et al., J. Mol. Biol. 222:581 (1991)].

In one embodiment the term "sugar" refers to a class of carbohydrate moleculesincluding sucrose, lactose, and fructose. In one embodiment the term "sugar" represents a saccharide. In one embodiment the term "saccharide" is synonym with the term sugar. In one embodiment saccharide refers to a monosaccharide, disaccharide, oligosaccharide orpolysaccharide. In one embodiment the monosaccharide has the molecular formula $(CH_2O)n$. In one preferred embodiment the monosaccharide is a molecule having the molecular formula $C_6H_{12}O_6$. In one embodiment monosaccarides comprise glucose (dextrose), fructose, galactose, xylose and ribose. In some embdoiments, disaccharides comprise sucrose (common sugar) and polysaccharides (such as cellulose and starch).

In one embodiment, the sugar is a sugar derivative. The term sugar derivative refers to any compound being derived from a sugar. In the present context sugar means any carbohydrate, including monosaccharides, disaccharides, trisaccharides, oligosaccharides, and polysaccharides, whether being a five-membered ring (pentose) or a six-membered ring (hexose) or combinations thereof, or whether being a D-form or an Inform, as well as substances derived from monosaccharides by reduction of the carbonyl group (alditols), by oxidation of terminal groups to carboxylic acids, or by replacement of hydroxy groups by another group. It also includes derivatives of these compounds. Examples of derivatives of the sugars are uronic acids, aldoses, in which the first $CH_2OH$-group has been exchanged with a carboxy group; aldaric acids, aldonic acids, in which the first $CH_2OH$-group has been exchanged with a carboxy group; deoxy sugars, monosaccharides, in which a hydroxyl group has been exchanged with a hydrogen; amino sugars, monosaccharides, in which a hydroxyl group has been exchanged with an amino group.

In one embodiment $R_1$, $R_2$, $R_3$, $R_4$, $R_1'$, $R_2'$, $R_3'$ and $R_4$ comprise a synthetic polymer. the term "synthetic polymer" refers to resins and polymers including polymethylmethacrylate (PMMA), acrylics, acrylates, polyethylene, polyethylene terepthalate, polycarbonate, polystyrene and other styrene polymers, polypropylene, polytetrafluoroethylene. In one embodiment, the polymers of this invention are polymers. In another embodiment, the polymers of this invention are homo- or, in another embodiment heteropolymers. In another embodiment, the polymers of this invention are synthetic, or, in another embodiment, the polymers are natural polymers. In another embodiment, the polymers of this invention are free radical polymers, or, in another embodiment, graft polymers. In one embodiment, the polymers may comprise proteins, peptides or nucleic acids.

In another embodiment, the choice of polymer, for example synthetic polymer utilized may be a function of the charge of the polymer, the solubility, the size, the configuration, and the chemical reactivity of the polymer. In one embodiment, the polymer may comprise a polymer of acrylic acid, styrene sulfonic acid, vinyl sulfonic acid, vinylbenzyl trimethyl ammonium chloride, acrylamidopropyl trimethyl ammonium chloride polymers, polyethylene oxide, polypropylene oxide polymer units or a combination thereof.

In one embodiment "conjugate" refers to a link, a bond, an association with, a connection with, fusion, relation to, modification of or a combination thereof of one entity to another.

In one embodiment protein conjugate or polymer conjugate refers to the polymers or proteins associated with compounds of this invention. In some embodiments, polymer or protein conjugates are parts or segments in the molecular structure of the compounds of the present invention.

In one embodiment, this invention provides a polymer of formula 1, 2, 2a and 2b and/or analog, derivative, isomer, metabolite, pharmaceutically acceptable salt, pharmaceutical product, hydrate, N-oxide, prodrug, polymorph, impurity or crystal or combinations thereof. In one embodiment, this invention provides an analog of the polymer. In another embodiment, this invention provides a derivative of the polymer. In another embodiment, this invention provides an isomer of the polymer. In another embodiment, this invention provides a metabolite of the polymer. In another embodiment, this invention provides a pharmaceutically acceptable salt of the polymer. In another embodiment, this invention provides a pharmaceutical product of the polymer. In another embodiment, this invention provides a hydrate of the polymer. In another embodiment, this invention provides an N-oxide of the polymer. In another embodiment, this invention provides a prodrug of the polymer. In another embodiment, this invention provides a polymorph of the polymer. In another embodiment, this invention provides a crystal of the polymer. In another embodiment, this invention provides an impurity of the polymer. In another embodiment, this invention provides composition comprising a polymer, as described herein, or, in another embodiment, a combination of an analog, derivative, isomer, metabolite, pharmaceutically acceptable salt, pharmaceutical product, hydrate, N-oxide, prodrug, polymorph, impurity or crystal of the polymers of the present invention.

In one embodiment, the term "isomer" includes, but is not limited to, optical isomers and analogs, structural isomers and analogs, conformational isomers and analogs, and the like.

In one embodiment, the term "isomer" is meant to encompass optical isomers of the polymer. It will be appreciated by those skilled in the art that the polymer of the present invention contain at least one chiral center. Accordingly, the polymer used in the methods of the present invention may exist in, and be isolated in, optically-active or racemic forms. Some compounds may also exhibit polymorphism. It is to be understood that the present invention encompasses any racemic, optically-active, polymorphic, or stereroisomeric form, or mixtures thereof, which form possesses properties useful in the treatment of androgen-related conditions described herein. In one embodiment, the polymer are the pure (R)-isomers. In another embodiment, the polymers are the pure (S)-isomers. In another embodiment, the polymers are a mixture of the (R) and the (S) isomers. In another embodiment, the polymers are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes "pharmaceutically acceptable salts" of the polymer of this invention, which may be produced, in one embodiment, using an amino-substituted polymer and an organic and inorganic acids, for example, citric acid and hydrochloric acid. Pharmaceutically acceptable salts can be prepared, from the phenolic compounds, in other embodiments, by treatment with inorganic bases, for example, sodium hydroxide. In another embodiment, esters of the phenolic compounds can be made with aliphatic and aromatic carboxylic acids, for example, acetic acid and benzoic acid esters. As used herein, "pharmaceutically acceptable salt" refers to, in one embodiment, those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M Berge, et al. describe pharmaceutically acceptable salts in detail in J. Pharmaceutical Sciences, 1977, 66: 1-19. The salts can be prepared in situ during the final isolation and purification of the compounds of the invention, or separately by reacting the free base function with a suitable organic acid. Representative acid addition salts include acetate, adipate, alginate, ascorbate, aspartate, benzene-sulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary as ammonium, and mine cations, including, but not limited to ammonium, tetramethylammonium, tetraethylammonium, methylamine, dimethylamine, trimethylamine, triethylamine, ethylamine, and the like.

The invention also includes N-oxides of the amino substituents of the polymer described herein.

This invention provides derivatives of the polymers. In one embodiment, "derivatives" includes but is not limited to ether derivatives, acid derivatives, amide derivatives, ester derivatives and the like. In another embodiment, this invention further includes hydrates of the polymers. In one embodiment, "hydrate" includes but is not limited to hemihydrate, monohydrate, dihydrate, trihydrate and the like.

This invention provides, in other embodiments, metabolites of the polymers. In one embodiment, "metabolite" means any substance produced from another substance by metabolism 5 or a metabolic process.

This invention provides, in other embodiments, pharmaceutical products of the polymers of this invention. The term "pharmaceutical product" refers, in other embodiments, to a composition suitable for pharmaceutical use (pharmaceutical composition), for example, as described herein.

In some embodiments, the polymers of this invention comprise a ligand for a biological target, which in another embodiment, provides for directional specificity to cells or tissues. In one embodiment, the term "ligand for a biological target" refers to a molecule which enables the specific delivery of the polymer or composition of this invention to a particular site in vivo. In one embodiment, the targeting agent specifically binds, or preferentially binds only diseased cells, which in some embodiments, are vasculature-associated cells, for delivery of a therapeutic agent, or in another embodiment, a cytotoxic agent.

In one embodiment, the polymeric group (P) comprises underivatized or derivatized monomers. In another embodiment, a derivatized monomer refers to a substituted monomer. In another embodiment, the monomer is substituted by an alkyl, halogen, cyano, nitro, amine, phosphonate or any combination thereof. In another embodiment, the monomer is substituted by another monomer forming a copolymer. In another embodiment, derivatized monomer refers to hydrolyzed, oxidized or reduced form of a monomer. In one embodiment, with regard to P comprising derivatized monomers of N-(2-hydroxypropyl)methacrylamide (IIPMA), N-methylacrylamide, N,N-dialkylacrylamides, acrylic acid, methacrylic acid, polyamino acids, polysaccharides, polymers containing polyethyleneoxide sequences and polyvinyl pyrrolidone-maleic anhydride polymers, polylactic-co-glycolic acid, dendrimers, saccharides, peptides, proteins, polymer-peptide conjugates and polymer-protein conjugates, it is to be understood that P may represent a copolymer of any combination of monomeric units as described in any repeating pattern, or any plausible or desired combination.

In one embodiment, the targeting moiety comprises the structure A, as described herein.

In some embodiments, the targeting moiety enhances attachment to a diseased cell, which is part of a neoplastic or preneoplastic process, which includes the generation of cancer-associated vasculature. In one embodiment, the site-specific expression of selectins (E- and P-selectin) on endothelial cells of blood vessels during angiogenesis provides an opportunity to target anti-cancer drugs to the vascular endothelium to extend the range of the therapeutic effect. The selective attachment of the selectin ligand sialyl Lewis X (sLe$^x$) to E- and P-selectin makes them an attractive target for local delivery of therapeutics to the vasculature of diseased tissues. In one embodiment E-selectin, found on angiogenic, but not on normal, blood vessels could selectively deliver drugs to the vasculature of cancerous tissues. In one embodiment, this invention describes an innovative drug targeting strategy for the selective delivery of the anticancer drugs to endothelial cells by means of polymer-drug conjugates modified with a carbohydrate ligand for the vascular selectins. In one embodiment the E- and P-selectin targeting moiety comprises a combination of quinic acid and a COOH moieties on a molecular backbone. In one embodiment the quinic acid and the COOH both provide a functional group for binding to the carbohydrate recognition domain of selectins. In another embodiment, small carbohydrate (fucose derivative) and non-carbohydrate (quinic acid derivative) analogs of the natural E-selectin ligand, sialyl Lewis X (sLe$^x$), etc., were designed as targeting ligands to E-selectin expressing vasculature of diseased tissues.

In one embodiment the quinic acid and the COOH are separated by a molecular spacer. In one embodiment the spacer comprises amino acids. In one embodiment the spacer comprises, C—C bonds, C═O bonds, N—H bonds or a combination thereof. In one embodiment the spacer length and structure is designed to provide enhanced binding and recognition between the targeting molecule and the selectins.

In one embodiment, the spacer is selected depending upon the properties desired. For example, the length of the spacer can be chosen to optimize the kinetics and specificity of ligand binding, including any conformational changes induced by binding of the ligand to a target receptor. The spacer, in some embodiments, should be long enough and flexible enough to allow the ligand moiety and the target cell receptor to freely interact. In some embodiments, if the spacer is too short or too stiff, there may be steric hindrance between the ligand moiety and the cell toxin. In some embodiments, if the spacer is too long, the cell toxin may be proteolysed in the process of production, or may not deliver its toxic effect to the target cell effectively. In some embodiments, the spacer can be attached to the monomeric units comprising the polymer, using numerous protocols known in the art, such as those described in the Examples herein, or via modifications of known methods (see, for example, Pierce Chemicals "Solutions, Cross-linking of Proteins: Basic Concepts and Strategies," Seminar #12, Rockford, Ill.).

In some embodiments, several linkers may be included in order to take advantage of desired properties of each linker. Chemical linkers and peptide linkers may be inserted by covalently coupling the linker to the targeting agent (TA) and the cytotoxic agent, or drug, for example. Heterobifunctional agents may be used to effect such covalent coupling. Peptide linkers may also be used. Flexible linkers and linkers that increase solubility of the polymers are contemplated for use, either alone or with other linkers are also contemplated herein.

In some embodiments, cleavable spacers are used. Heterobifunctional cleavable cross-linkers may comprise N-succinimidyl (4-iodoacetyl)-aminobenzoate; sulfosuccinimydil (4-iodoacetyl)-aminobenzoate; 4-succinimidyl-oxycarbonyl-a-(2-pyridyidithio)-toluene; sulfosuccinim- idyl-6-[a-methyl-a-(pyridyidithiol)-toluamido]hexanoate; N-succinimidyl-3-(-2-pyridyldithio)-proprionate; succinimidyl 6[3(-(-2-pyridyidithio)-proprionamido]hexanoate; sulfosuccinimidyl 6[3(-(-2-pyridyidithio)-propionamido] hexanoate; 3-(2-pyridyidithio)-propionyl hydrazide, Ellman's reagent, dichlorotriazinic acid, S-(2-thiopyridyl)-L-cysteine. Further exemplary bifunctional spacers are disclosed in U.S. Pat. Nos. 5,349,066, 5,618,528, 4,569,789, 4,952,394, and 5,137,877.

The term linker and spacer may, in some embodiments, be considered to be synonymous.

Acid cleavable spacers, photocleavable and heat sensitive spacers may also be used, particularly where it may be necessary to cleave the targeted agent to permit it to be more readily accessible to reaction. Acid cleavable linkers/spacers include, but are not limited to, bismaleimideothoxy propane; and adipic acid dihydrazide linkers (see, e.g., Fattom et al. (1992) Infection & Immun. 60:584-589) and acid labile transferrin conjugates that contain a sufficient portion of transferrin to permit entry into the intracellular transferrin cycling pathway (see, e.g., Welhner et al. (1991) J. Biol. Chem. 266:4309-4314).

Photocleavable linkers are linkers that are cleaved upon exposure to light (see, e.g., Goldmacher et al. (1992) Bioconj. Chem. 3:104-107, which linkers are herein incorporated by reference), thereby releasing the targeted agent upon exposure to light. Photocleavable linkers that are cleaved upon exposure to light are known (see, e.g., Hazum et al. (1981) in Pept., Proc. Eur. Pept. Symp., 16th, Brunfeldt, K (Ed), pp. 105-110, which describes the use of a nitrobenzyl group as a photocleavable protective group for cysteine; Yen et al. (1989) Makromol. Chem 190:69-82, which describes water soluble photocleavable polymers, including hydroxypropylmethacrylamide polymer, glycine polymer, fluorescein polymer and methylrhodamine polymer; Goldmacher et al. (1992) Bioconj. Chem. 3:104-107, which describes a cross-linker and reagent that undergoes photolytic degradation upon exposure to near UV light (350 nm); and Senter et al. (1985) Photochem. Photobiol 42:231-237, which describes nitrobenzyloxycarbonyl chloride cross linking reagents that produce photocleavable linkages), thereby releasing the targeted agent upon exposure to light. Such linkers would have particular use in treating dermatological or ophthalmic conditions that can be exposed to light using fiber optics. After administration of the conjugate, the eye or skin or other body part can be exposed to light, resulting in release of the targeted moiety from the conjugate. Such photocleavable linkers are useful in connection with diagnostic protocols in which it is desirable to remove the targeting agent to permit rapid clearance from the body of the animal.

In some embodiments, such targeting polymers are characterized by of the polymers of this invention.

In one embodiment, the polymers or compositions of this invention comprise a drug. In one embodiment, the term "drug" refers to a substance applicable for use in the diagnosis, or in another embodiment, cure, or in another embodiment, mitigation, or in another embodiment, treatment, or in another embodiment, prevention of a disease, disorder, condition or infection. In one embodiment, the term "drug" refers to any substance which affects the structure or function of the target to which it is applied.

In another embodiment, the term "drug" refers to a molecule that alleviates a symptom of a disease or disorder when administered to a subject afflicted thereof. In one embodiment, a drug is a synthetic molecule, or in another embodiment, a drug is a naturally occurring compound isolated from a source found in nature.

In one embodiment, drugs may comprise any agent, which is useful in halting or altering the course of frank neoplasia or metastasis. In some embodiments, the drug is cytotoxic to neoplastic cells or preneoplastic cells selectively, or in some embodiments, preferentially. In some embodiments, two or more drugs may be incorporated in the polymers of the invention, where the first drug is cytotoxic to the neoplastic or preneoplastic cells, and the second, etc. drug is protective of healthy tissue.

In some embodiments, the first or second drug may comprise anti-inflammatories, antibacterial and antifungal agents, antiviral agents, anti-neoplastics, or other drugs as will be 25 appreciated by the skilled artisan.

In one embodiment, examples of the drugs conjugated to the polymers of this invention, comprise, inter-alia, anti-neoplastics such as chlorambucil, lomustine or echinomycin; anti-inflammatory agents such as betamethasone, prednisolone, piroxicam, aspirin, flurbiprofen and (+)-N-{4-[3-(4-fluorophenoxy)phenoxy]-2-cyclopenten-1-yl}-N-hyroxyurea; antivirals such as acyclovir, nelfinavir, or virazole; vitamins/nutritional agents such as retinol and vitamin E an antibiotic such as ampicillin and penicillin G; an anti-infective such as benzalkonium chloride or chlorhexidine; an antifungal such as econazole, terconazole, fluconazole, voriconazole or griseofulvin; an antiprotozoal such as metronidazole; an imidazole-type anti-neoplastic such as tubulazole; an anthelmintic agent such as thiabendazole or oxfendazole; an antihistamine such asastemizole, levocabastine, cetirizine, or cinnarizine; a tetracycline antibiotic such as oxytetracycline or minocycline; a macrolide antibiotic such as azithromycin, clarithromycin, erythromycin or spiramycin; or combinations thereof.

Further examples of drugs deliverable by the invention are the antiinflammatories 5 piroxicam and celicoxib and valdicoxib, and the antibiotics carbenicillin indanyl sodium, bacampicillin hydrochloride, troleandomycin, and doxycycline hyclate.

In another embodiment a drug of this invention may comprise other antineoplastic agents such as platinum compounds (e.g., spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, paclitaxel and other taxenes, rapamycin, manumycin A, TNP-470, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, interferon .alpha.-2a, interferon .alpha.-2b, teniposide (VM-26), vinblastine sulfate (VLB), vincristine sulfate, bleomycin sulfate, hydroxyurea,procarbazine, and dacarbazine; mitotic inhibitors such as etoposide, colchicine, and the vinca alkaloids, radiopharmaceuticals such as radioactive iodine and phosphorus products; hormones such as progestins, estrogens and antiestrogens; anti-helmintics, antimalarials, and antituberculosis drugs; biologicals such as immune serums, antitoxins and antivenoms; rabies prophylaxis products; bacterial vaccines; viral vaccines; biological response modifiers such as muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide N-acetylmuramyl-L-alanyl-Disoglutamine; anti-fungal agents such as ketoconazole, nystatin, griseofulvin, flucytosine (5-fc), miconazole, amphotericin B, ricin, cyclosporins, and B-lactam antibiotics (e.g., sulfazecin); hormones such as growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone acetate, oxytocin, vassopressin, and their derivatives; vitamins such as cyanocobalamin neinoic acid, retinoids and derivatives such as retinol palmitate, and .alpha.-tocopherol; peptides, such as manganese super oxide dismutase; enzymes such as alkaline phosphatase; anti-allergic agents such as amelexanox; antituberculars such as para-aminosalicylic acid, isoniazid, capreomycin sulfate cycloserine, ethambutol hydrochloride ethionamide, pyrazinamide, rifampin, and streptomycin sulfate; antivirals such as amantadine azidothymidine (AZT, DDI, Foscarnet, or Zidovudine), ribavirin and vidarabine monohydrate (adenine arabinoside, ara-A); antianginals such as diltiazem, nifedipine, verapamil, erythritol tetranitrate, isosorbide dinitrate, nitroglycerin (glyceryl trinitrate) and pentaerythritol tetranitrate; antiinflammatories such as diflunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; radioactive particles or ions such as strontium, iodide rhenium and yttrium, or any combination of drug or agent as herein described.

In one embodiment, the term "drug" refers to a therapeutic compound. In one embodiment, the therapeutic compound is a peptide, a protein, a glycoprotein, a nucleic acid, a small molecule, or any molecule which may effect the desired function. In another embodiment, the therapeutic compound is an antibacterial, antiviral, antifungal or anti-parasitic compound. In another embodiment, the therapeutic compound has cytotoxic or anti-cancer activity. In another embodiment, the therapeutic compound is an enzyme, a receptor, a channel protein, a hormone, a cytokine or a growth factor. In another embodiment, the therapeutic compound is immunostimulatory. In another embodiment, the therapeutic compound inhibits inflammatory or immune responses.

In one embodiment, the term "therapeutic", refers to a molecule, which when provided to a subject in need, provides a beneficial effect.

In one embodiment, the therapeutic protein may include cytokines, such as interferons or interleukins, or their receptors.

In another embodiment, the therapeutic protein may comprise an enzyme, which cleaves undesirable molecules, for example, those associated with angiogenesis. In another embodiment, the drug may comprise a molecule which inhibits an enzyme, such as a matrix degrading enzyme, for example, matrix metalloproteinases.

In another embodiment, the therapeutic protein comprises a tumor suppressor, or pro-apoptotic compound, which alters progression of cancer-related events.

In another embodiment, the therapeutic compound of the present invention may comprise an immunomodulating protein. In one embodiment, the immunomodulating protein comprises cytokines, chemokines, complement or components, such as interleukins 1 to 15, interferons alpha, beta or gamma, tumour necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MW-1a and MIP-1b, or complement components.

In another embodiment, a therapeutic compound of this invention may comprise a growth factor, or tissue-promoting factor.

In one embodiment, drug may also refer to a nucleic acid, or construct comprising a nucleic acid, whose expression ameliorates or abrogates symptoms of a disease or a disorder, or diminishes, suppresses or inhibits a disease, disorder or condition, which is desirable, for example, inhibiting angiogenesis or factors involved in angiogenesis.

In another embodiment, the therapeutic molecule may be natural or non-natural amylases, proteases, lipases, kinases, phosphatases, glycosyl transferases, trypsinogen, chymotrypsinogen, carboxypeptidases, hormones, ribonucleases, deoxyribonucleases, triacylglycerol lipase, phospholipase A2, elastases, blood clotting factors, UDP glucuronyl transferases, ornithine transcarbamoylases, cytochrome p450 enzymes, adenosine deaminases, serum thymic factors, thymic humoral factors, thymopoietins, growth hormones, costimulatory factors, antibodies, colony stimulating factors, erythropoietin, epidermal growth factors, hepatic erythropoietic factors (hepatopoietin), liver-cell growth factors, interleukins, interferons, negative growth factors, fibroblast growth factors, transforming growth factors of the a family, transforming growth factors of the β family, cholecystokinins, somatostatins, serotonins, substance P. transcription factors or combinations thereof.

In one embodiment the drug may be a toxin. In one embodiment, the term "toxin" refers to a molecule which results in toxic effects in cells and/or tissue exposed to the toxin. In one embodiment, the toxin results in cell death, or in another embodiment, cell damage. In one embodiment, the toxin is a natural product of cells, such as bacterial cells, wherein the toxin is used, in one embodiment, when specifically targeted to disease cells as a means of selective cell killing of diseased cells. In one embodiment, the toxin may comprise any known in the art, such as, for example that produced by cholera, tetanus, or any other appropriate species, as will be appreciated by one skilled in the art.

In another embodiment, this invention also comprises incorporation of any toxic substance for therapeutic purpose. In one embodiment, the polymers of this invention may incorporate an oligonucleotide encoding a suicide gene, which when in contact with diseased cells or tissue, is expressed within such cells. In one embodiment, the term "suicide gene" refers to a nucleic acid coding for a product, wherein the product causes cell death by itself or in the presence of other compounds. A representative example of a suicide gene is one, which codes for thymidine kinase of herpes simplex virus. Additional examples are thymidine kinase of varicella zoster virus and the bacterial gene cytosine deaminase, which can convert 5-fluorocytosine to the highly cytotoxic compound 5-fluorouracil.

Suicide genes may produce cytotoxicity by converting a prodrug to a product that is cytotoxic. In one embodiment, the term "prodrug" means any compound that can be converted to a toxic product for cells. Representative examples of such a prodrug is gancyclovir which is converted in vivo to a toxic compound by HSV-thymidine kinase. The gancyclovir derivative subsequently is toxic to cells. Other representative examples of prodrugs include acyclovir, FIAU [1-(2-deoxy-2-fluoro-β-D-arabinofuranosyl)-5-iodouracil], 6-methoxypurine arabinoside for VZV-TK, and 5-fluorocytosine for cytosine deaminase.

In one embodiment, the incorporated groups described herein, which are to comprise 20 polymers or compositions of this invention, may be conjugated to the polymer.

In one embodiment, the term "a tag" or "a labeling agent" refers to a molecule which renders readily detectable that which is contacted with a tag or a labeling agent. In one embodiment, the tag or the labeling agent is a marker polypeptide. The marker polypeptide may comprise, for example, green fluorescent protein (GFP), DS-Red (red fluorescent protein), secreted alkaline phosphatase (SEAP), beta-galactosidase, luciferase, or any number of other reporter proteins known to one skilled in the art. In another embodiment, the labeling agent may be conjugated to another molecule which provides greater specificity for the target to be labeled. For example, and in one embodiment, the labeling agent is a fluorochrome conjugated to an antibody which specifically binds to a given target molecule, or in another embodiment, which specifically binds another antibody bound to a target molecule, such as will be readily appreciated by one skilled in the art.

In one embodiment, the polymer may be conjugated to a quantum dot. In one embodiment, the term "quantum dot" refers to a semiconductor nanocrystal with size-dependent optical and electronic properties. In particular, the band gap energy of a semiconductor nanocrystal varies with the diameter of the crystal. "Semiconductor nanocrystal" includes, for example, inorganic crystallites between about 1 nm and about 1000 nm in diameter, or in one embodiment, between about 2 nm and about 50 nm, or in another embodiment, between about 5 nm to about 20 nm (such as about 5, 6, 7, 8, 9, 10, 11, 12, 13, 14, 15, 16, 17, 1 8, 19, or 20 nm) that includes a "core" of one or more first semiconductor materials, and which can be surrounded by a "shell" of a second semiconductor material. A semiconductor nanocrystal core surrounded by a semiconductor shell is referred to as a "core/shell" semiconductor nanocrystal. The surrounding "shell" material may, in another embodiment, have a bandgap greater than the bandgap of the core material and can be chosen so to have an atomic spacing close to that of the "core" substrate. The core and/or the shell can be a semiconductor material including, but not limited to, those of the group II-VI (e.g., ZnS, ZnSe, ZnTe, CdS, CdSe, CdTe, HgS, HgSe, HgTe, MgTe and the like) and III-v (e.g., GaN, GaP, GaAs, GaSb, InN, InP, InAs, InSb, AlAs, AlP, AlSb, AIS, and the like) and IV (e.g., Ge, Si, Pb and the like) materials, and an alloy thereof, or a mixture, including ternary and quaternary mixtures, thereof.

In one embodiment imaging or detection is referred to as radiological. In one embodiment imaging or detection is done by means of nuclear magnetic resonance (NMR). In one embodiment the NMR is done with a magnetic field gradient. In one embodiment the imaging method involves magnetic resonance imaging (MRI). In one embodiment compounds of the present invention comprise an NMR active atoms. In one embodiment, compounds of this invention comprise $^{19}$F.

In another embodiment, the methods of this invention are directed to the imaging of individual cells, a group of cells, a tissue, an organ or a combination thereof.

In one embodiment, imaging is accomplished with computed tomography, computed radiography, magnetic resonance imaging, fluorescence microscopy, angiography, arteriography, or a combination thereof. In one embodiment, a cell is contacted with a polymer of this invention, ex-vivo, and is subsequently implanted in a subject. In one embodiment, the cell is inter-alia, labeled with a labeling agent as described herein, and may further comprise a therapeutic compound, and/or in another embodiment, the theraepeutic compound is labeled with a labeling agent, and in one embodiment, the delivery of the cell and/or therapeutic compound may be verified by imaging the labeling agent.

In one embodiment, the imaging methods of this invention are conducted on a subject. In another embodiment, the imaging methods are conducted on a sample taken from a subject. In one embodiment, the subject has or is suspected of having cancer.

In one embodiment, the imaging methods as described herein may comprise near infrared fluorescence imaging. In one embodiment, an advantages of such optical imaging methods may include the use of non-ionizing low energy radiation, high sensitivity with the possibility of detecting micron-sized objects, continuous data acquisition, and the development of potentially cost-effective equipment. Optical imaging can be carried out at different resolutions and depth penetrations. Fluorescence-mediated tomography (FMT) can three-dimensionally localize and quantify fluorescent probes in deep tissues at high sensitivity. Several NIR fluorochromes have recently been coupled to affinity molecules (Becker, A., et al. Nature Biotechnology, 19: 327-331, 2001; Folli, S., et al Cancer Research, 54: 2643-2649, 1994, and can be adapted to comprise the polymers or micelles of this invention, as will be appreciated by one skilled in the art.

In one embodiment, the imaging methods as described herein may comprise nuclear imaging methods. Nuclear imaging is based on labeling molecules with a radioactive atom before their release in the system under study. Since photons of relatively high energy (>80 keV) can escape from the human body, it is possible to follow over time the 3D spatial distribution of the radioactive tracer through detection of the emitted radiation. A large variety of isotopes can be imaged. Their broadest classification is perhaps that in gamma and positron emitters: the former family is at the basis of single photon emission methods (such as planar scintigraphy and tomography, or SPECT), and the latter is used in Positron Emission Tomography (PET). Unlike in MRI or computed tomography (CT), the signal detected in nuclear imaging techniques is the radioactive emission of a single atom. Because these emissions are specific to the radioisotope used, and because it is possible with standard physics instrumentation to detect the emission of a single atom, nuclear imaging enjoys the advantages of both high specificity and sensitivity. Structural information, however, may be obtained only as far as the radiotracer redistributes following anatomical structures. Resolution of clinical scanners may be limited to about 5-6 mm for PET and ~1 cm for SPECT, thus, nuclear imaging methods are often used to complement the information provided by CT and/or MRI scans in the context of multimodality imaging, and may be applied in this manner herein, representing an embodiment of this invention. In one embodiment, nuclear imaging is used in particular because of its sensitivity to extremely small quantities of matter. For example, it has recently been estimated that PET can detect as few as a cluster of 250 cells each bearing 30 Bq of $^{18}$F, which corresponds to 2.1 fg.

In another embodiment, different iodine isotopes can be chosen for radioactive labeling of compounds. In one embodiment, $^{123}$I, $^{125}$I, and $^{131}$I can be used to obtain molecules with the same chemical and biological characteristics but different imaging and dosimetric properties.

In another embodiment, the polymers of this invention allow for the combination of different imaging modalities. In one embodiment imaging comprises X-ray, MRi, ultrasound or a combination thereof.

Compositions

In one embodiment this invention provides a pharmaceutical composition comprising the polymers of this invention.

In one embodiment the composition further comprising a carrier, diluent, lubricant, flow-aid, or a mixture thereof. In one embodiment the composition is in the form of a pellet, a tablet, a capsule, a solution, a suspension, a dispersion, an emulsion, an elixir, a gel, an ointment, a cream, an I.V. solution or a suppository. In one embodiment the composition is in the form of a capsule. In one embodiment the composition is in a form suitable for oral, intravenous, intraarterial, intramuscular, intracranial, intranasal, subcutaneous, parenteral, transmucosal, transdermal, intratumoral or topical administration. In one embodiment the composition is a controlled release composition. In one embodiment the composition is an immediate release composition. In one embodiment the composition is a liquid dosage form. In one embodiment the composition is a solid dosage form. In one embodiment the composition further comprises an antineoplastic compound, an immunotherapeutic agent or a drug.

In another embodiment, this invention provides a composition comprising a polymer of this invention. In one embodiment this invention provides a pharmaceutical composition comprising the polymers of the present invention.

In one embodiment the composition further comprising a carrier, diluent, lubricant, flow-aid, or a mixture thereof. In one embodiment the composition is in the form of a pellet, a tablet, a capsule, a solution, a suspension, a dispersion, an emulsion, an elixir, a gel, an ointment, a cream, an I.V. solution or a suppository. In one embodiment the composition is in the form of a capsule.

Pharmaceutical compositions of this invention for parenteral injection comprise pharmaceutically acceptable sterile aqueous or nonaqueous solutions, dispersions, suspensions, or emulsions as well as sterile powders for reconstitution into sterile injectable solutions or dispersions just prior to use. Examples of suitable aqueous and nonaqueous carriers, diluents, solvents, or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

In one embodiment the composition is in a form suitable for oral, intravenous, intraarterial, intramuscular, intracranial, intranasal, subcutaneous, parenteral, transmucosal, transdermal, rectally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrathecally, intrasternal, subcutaneous and intraarticular injection and infusion.

In one embodiment the composition can be administered to humans and other animals. In one embodiment the composition is a controlled release composition. In one embodiment the composition is an immediate release composition. In one embodiment the composition is a liquid dosage form. In one embodiment the composition is a solid dosage form. In one embodiment the composition further comprising an antineoplastic compound, an immunotherapeutic agent or a drug. In one embodiment, the compositions of this invention, which comprise a polymer of this invention is biocompatible, and in another embodiment, may comprise pharmaceutically acceptable carriers or excipients, such as disclosed in Remington's Pharmaceutical Sciences, Mack Publishing Company, Easton, Pa., USA, 1985. The polymers, of this invention may be used in the treatment or diagnosis of certain conditions such as in tagging, detecting or removing cancer cells for example from a sample or tissue. These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Compositions for rectal or vaginal administration are, in one embodiment, suppositories which can be prepared by mixing the compounds of this invention with suitable non-irritating excipients or carriers such as cocoa butter, polyethylene glycol, or a suppository wax which are solid at room temperature but liquid at body temperature and therefore melt in the rectum or vaginal cavity and release the active compound.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the polymer compound of the present invention, stabilizers, preservatives, excipients, and the like. In one embodiment, the lipids may be natural or synthetic phospholipids or a combination thereof.

Methods to form liposomes are known in the art. See, for example, Prescott, Ed., Methods in Cell Biology, Volume XIV, Academic Press, New York, N.Y. (1976), p. 33 et seq. Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend as upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved.

The pharmaceutical compositions of the present invention can be used in both veterinary medicine and human therapy. The magnitude of a prophylactic or therapeutic dose of the pharmaceutical composition of the invention will vary with the severity of the condition to be treated and the route of administration. The dose, and perhaps the dose frequency, will also vary according to the age, body weight, and response of the individual patient.

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

This invention provides a polymer, which in one embodiment, is water soluble. In one embodiment, water soluble polymers allow for the polymers to be delivered through the blood stream. The polymers of this invention, in some embodiments, offer a number of advantages as delivery systems, as compared to other such systems described in the art, as a result of the unique chemical structure of the polymers of this invention.

The polymers of this invention may assume any structural configuration, which will be a function of, in some embodiments, the chemical makeup of the polymers, and the environment to which the polymer is exposed. In some embodiments, the polymers of this invention may assume a particle configuration.

In other embodiments, the polymers of this invention may comprise a targeting agent.

In one embodiment, the polymers of this invention may contain a therapeutic agent as described, and additionally comprise a targeting agent, such that the targeting agent serves to deliver the therapeutic agent to a desired location, for therapeutic applications. In another embodiment, the targeting agent serves for diagnostic and/or imaging purposes, where an agent is delivered to a particular site, where verification of delivery is desired. In another embodiment, the targeting agent serves to provide a sensitive means of detection of a particular molecule at a particular site, for example, the targeting agent directs a polymer of this invention to a tissue which expresses a preneoplastic marker, or a cancer associated receptor or molecule, wherein the molecule which is being detected is available in low concentration, and in some embodiments, is not detectable by existing methods in the art.

In some embodiments, the targeting agent may be coupled to a free HPMA unit at an end of a base polymer chain.

In some embodiments, through the use of various chain lengths, linkers, side chains, and side chain terminal groups, great flexibility in polymer chemical composition, size, structure, and function can be obtained. In some embodiments, such polymers may be constructed via multiple-step reaction pathways that involve synthesis of a suitable monomer with a protected functional group prior to the polymerization step, followed by deprotection. In other embodiments, the synthesis may be carried out with a chemical/enzymatic/chemo-enzymatic approach as exemplified and described further herein.

Synthesis of the polymer precursors or of the polymers of this invention may be carried out in a number of representative suitable solvents including anhydrous polar aprotic solvents such as acetonitrile, tetrahydrofuran, dioxane, or the like, halogenated solvents such as chloroform, or the like. In some embodiments, synthesis is conducted as exemplified herein, or as a variation thereof, as will be appreciated by the skilled artisan. Synthesis of the monomeric units of the polymers and their linkage to other monomeric units are understood to reflect the choice of monomeric unit and can be accomplished by routine methodology known in the art.

In another embodiment, the polymers are synthesized enzymatically. In one embodiment, the enzymes used to synthesize the polymers of this invention comprise lipases, such as, for example Candida antarctica lipase, or in another embodiment, lipase A, or in another embodiment, lipase B. In another embodiment, the enzyme may comprise an esterase, or in another embodiment, a protease, such as, for example papain or chymotrypsin. In one embodiment, molecular weight of the hydrophilic units is chosen such that its ability to affect polymerization is considered. In one embodiment, the polymer is functionalized with for example, an alkyl group of varying chain length, comprising a polar functionality at the end of the chain.

Polymers obtained by methods as described herein can be characterized by methods well known in the art. For example, the molecular weight and molecular weight distributions can be determined by gel permeation chromatography (GPC), matrix assisted laser desorption ionization (MALDI), and static or dynamic light scattering. Physical and thermal properties of the polymer products can be evaluated by thermal gravemetric analysis (TGA), differential scanning calorimetry (DSC), or surface tensiometer; the chemical structures of the polymers can be determined by, e.g., NMR (1H, 13C NMR, 1H-1H correlation, or 1H-13C correlation), IR, UV, Gas Chromatography-Electron Impact Mass Spectroscopy (GC-EIMS), ELMS, or Liquid Chromatography Mass Spectroscopy (LCMS).

In some embodiments this invention is related to the treatment of cancer or other conditions in a subject by administering compounds and/or compositions of the present invention. In one embodiment this invention provides a method of treating an inflammatory condition in a subject, the method comprising administering a polymer of the present invention to a subject.

In one embodiment this invention provides a method of treating, reducing the incidence of, delaying progression of, reducing the pathogenesis of, prolonging remission of cancer or inhibiting metastasis of a cancer in a subject, the method comprising the step of contacting a neoplastic cell or vasculature associated with a neoplastic cell in a subject with a polymer of the present invention.

In one embodiment, the polymer binds to receptors on the neoplastic cells. In one embodiment, the receptors are selectins. In one embodiment, the selectins are E- and P-selectins.

In one embodiment, the polymer interferes with endothelial cell alignment proximal to the neoplastic cell. In one embodiment, the polymer abrogates or disrupts association of the neoplastic cell with the vasculature or components thereof. In one embodiment, the polymer prevents, abrogates or diminishes angiogenesis associated with the neoplastic cell. In one embodiment, the neoplastic cell is derived from the lung, breast, prostate, colon or pancreas. In one embodiment, the neoplastic cell is a carcinoma, sarcoma, lymphoma, or leukemia cell.

In one embodiment, the polymer is administered intratumorally.

In one embodiment the method of treating, reducing the incidence of, delaying progression of, reducing the pathogenesis of, prolonging remission of cancer or inhibiting metastasis of a cancer in a subject, further comprising the step of providing adjunct anti cancer therapy to said subject. In one embodiment the adjunct anti-cancer therapy comprises surgery, chemotherapy, radiation or a combination thereof.

In one embodiment the B and C monomer comprises a spacer comprising a cleavable moiety. In one embodiment the cleavable moiety is a tetra-peptide. In one embodiment the tetra-peptide is (Gly-Phe-Leu-Gly SEQ ID NO: 10). In one embodiment the cleavable moiety is cleaved to release the drug. In one embodiment the cleavage is induced chemically. In one embodiment the cleavage is induced after the polymer binds the neoplastic cell. In one embodiment the cleavage is induced by cysteine peptidases. In one embodiment the cysteine peptidase is cathepsin B. In one embodiment the source of said cathepsin B is the lysosomal compartments of tumor cells.

In one embodiment this invention provides a method of diagnosing cancer in a subject, wherein the method comprising contacting a polymer of the present invention to a neoplastic cell or vasculature associated with a neoplastic cell in the subject. In one embodiment the diagnosis comprises the detection of the tag moiety on the polymer. In one embodiment the tag moiety is FITC. In one embodiment the detection of the tag moiety is an optical detection.

In one embodiment, the term "treating" refers to curing a disease. In another embodiment, "treating" refers to preventing a disease. In another embodiment, "treating" refers to reducing the incidence of a disease. In another embodiment, "treating" refers to inducing remission. In another embodiment, "treating" refers to slowing the progression of a disease. The terms "reducing", "suppressing" and "inhibiting" refer in one embodiment, to lessening or decreasing. The term "progression" may refers to increasing in scope or severity, advancing, growing or becoming worse. The term "recurrence" refers, in one embodiment, to the return of a disease after a remission.

In one embodiment, the term "administering" refers to bringing a subject in contact with a nucleotide molecule of the present invention. In another embodiment, administration is accomplished in vitro, i.e. in a test tube. In another embodiment, administration is accomplished in vivo, i.e. in cells or tissues of a living organism. Each possibility represents a separate embodiment of the present invention.

In one embodiment cancers are classified by the type of cell that resembles the tumor and, therefore, the tissue presumed to be the origin of the tumor. In one embodiment the cancer type is carcinoma, in which Malignant tumors are derived from epithelial cells. In one embodiment carcinoma represents the most common cancers, including the common forms of breast, prostate, lung and colon cancer. In another embodiment the cancer type is sarcoma. In one embodiment this type of cancer comprises malignant tumors derived from connective tissue, or mesenchymal cells. In another embodiment the cancer type is lymphoma or leukemia. In one embodiment this cancer type comprises malignancies derived from hematopoietic (blood-forming) cells. In another embodiment the cancer type is in the form of a germ cell tumor. In one embodiment such tumor is derived from totipotent cells. In another embodiment, the tumor is a blastic tumor. In one embodiment this is a usually malignant tumor which resembles an immature or embryonic tissue.

In some embodiments, the compounds/compositions and methods of this invention are useful in treating any vascularized tumor, for example, a solid tumor, including but not limited to, carcinomas of the lung, breast, ovary, stomach, pancreas, larynx, esophagus, testes, liver, parotid, bilary tract, colon, rectum, cervix, uterus, endometrium, kidney, bladder, prostrate, thyroid, squamous cell carcinomas, adenocarcinomas, small cell carcinomas, melanomas, gliomas, neuroblastomas, sarcomas (e.g., angiosarcomas, chondrosarcomas).

In some embodiments, the compounds/compositions and/or methods of this invention comprise treating a cancer wherein the subject is provided other anti-cancer adjunct therapy, for example, including radiation, chemotherapy and surgical removal of neoplastic cells or tissue. In some embodiments, such adjunct therapy may comprise administration of other chemotherapeutic agents (e.g., alkylating agents (e.g., nitrogen mustards (e.g., cyclophosphamide, ifosfamide, mechlorethamine, melphalen, chlorambucil, hexamethylmelamine, thiotepa), alkyl sulfonates (e.g., busulfan), nitrosoureas, triazines) antimetabolites (e.g., folic acid analogs, pyrimidine analogs (e.g., fluorouracil, floxuridine, cytosine arabinoside, etc.), purine analogs (e.g., mercaptopurine, thiogunaine, pentostatin, etc.), natural products (e.g., vinblastine, vincristine, etoposide, tertiposide, dactinomycin, daunorubicin, doxurubicin, bleomycin, mithrmycin, mitomycin C, L-asparaginase, interferon alpha), platinum coordination complexes (e.g., cis-platinum, carboplatin, etc.), mitoxantrone, hydroxyurea, procarbazine, hormones and antagonists (e.g., prednisone, hydroxyprogesterone caproate, medroxyprogesterone acetate, megestrol acetate, diethylstilbestrol, ethinyl estradiol, tamoxifen, testosterone propionate, fluoxymesterone, flutamide, leuprolide, etc.), other anti-angiogenesis agents or inhibitors (e.g., angiostatin, retinoic acids and paclitaxel, estradiol derivatives, thiazolopyrimidine derivatives, etc.), apoptosis-inducing agents (e.g., antisense nucleotides that block oncogenes which inhibit apoptosis, tumor suppressors, TRAIL, TRAIL polypeptide, Fas-associated factor 1, interleukin-1(3-converting enzyme, phosphotyrosine inhibitors, RXR retinoid receptor agonists, carbostyril derivatives, etc.) or chelators (penicillamine, zinc, trientine, etc.). In some embodiments, such compounds may be conjugated to the quinnic acid derivatives as herein described, thereby comprising the polymers of the invention, and/or be supplied in trans, as part of a second composition.

In other embodiments, the compounds of this invention are useful in treating any disease associated with undesirable neovascularization, for example, corneal neovascularization, or retinal neovascularization or other diseases of the eye. In some embodiments, eye diseases associated with neovascularization that can be treated according to the present invention include but are not limited to, diabetic retinopathy, retinopathy of prematurity, corneal graft rejection, neovascular glaucoma and retrolental fibroplasia, epidemic keratoconjunctivitis, retinal detachment or others known to the skilled artisan.

Other examples of eye diseases, which can be treated with the compounds/compositions encompassed by the present invention include, but are not limited to, macular degeneration, including age-related macular degeneration, contact lens overwear, atopic keratitis, superior limbic keratitis, pterygium keratitis sicca, Terrien's marginal degeneration, marginal ketatolysis, radial keratotomy, presumed ocular histoplasmosis, chronic uveitis/vitritis, myopia, optic pits, pars planitis, chronic retinal detachment, hyperviscosity syndromes, scleritis, trauma, post-laser complications, rubeosis, infections causing retinitis or choroiditis, and diseases caused by abnormal proliferations of fibrovascular or fibrous tissue, including all forms of prolific vitreoretinopathy.

In some embodiments, the compounds/compositions and methods are useful in treating other diseases associated with neovascularization, such as, but not limited to inflammatory bowel diseases such as Crohn's disease and ulcerative colitis. Both Crohn's disease and ulcerative colitis are characterized by chronic inflammation and angiogenesis at various sites in the gastrointestinal tract. Crohn's disease is characterized by chronic granulomatous inflammation throughout the gastrointestinal tract consisting of new capillary sprouts surrounded by a cylinder of inflammatory cells. Prevention of angiogenesis by the compounds/compositions and methods of the present invention inhibits the formation of the sprouts and prevents the formation of granulomas.

In some embodiments, the compounds/compositions and methods are useful in treating other diseases associated with E-selectin overexpression. In some embodiments, such expression may be found in infection or inflammatory conditions. In some embodiments, targeting such affected tissue with the molecules of this invention are envisioned and are to be considered as part of this invention.

In some embodiments, the compounds/compositions and methods are useful in treating inflammation.

In some embodiments, the compounds/compositions and methods are useful in treating an inflammatory conditions involving the selectins. In another embodiment, such inflammatory conditions include rheumatoid arthritis, asthma, transplant rejection, psoriasis, inflammatory bowel disease, ischemia/reperfusion injury, diabetes, multiple sclerosis, or other autoimmune diseases or infections.

In some embodiments, diseases resulting in tissue degradation may be treated with the compounds/compositions or by the methods of this invention, for example, Bartonelosis, acne rosacea, syphilis, sarcoidosis, chemical burns, bacterial ulcers, fungal ulcers, Behcet's syndrome, Stevens-Johnson's disease, Mycobacteria infections, Herpes simplex infections, Herpes zoster infections, protozoan infections, Mooren's ulcer, leprosy, Wegener's sarcoidosis, and pemphigoid.

The compositions and methods of the present invention can also treat chronic inflammatory conditions, for example psoriasis or diseases associated with psoriasis. Psoriasis, a skin disease, is another chronic and recurrent disease that is characterized by papules and plaques of various sizes. Prevention of the formation of the new blood vessels necessary to maintain the characteristic lesions leads to relief from the symptoms.

Other angiogenesis-associated diseases or disorders which can be treated with the compounds/compositions or by the methods encompassed by the present invention include, but are not limited to, osteoarthritis, lupus, systemic lupus erythematosis, polyarteritis, artery occlusion, vein occlusion, carotid obstructive disease, sickle cell anemia, pseudoxanthoma elasticum, Paget's disease, lyme's disease, Best's disease, Eale's disease, Stargardt's disease, toxoplasmosis, phylectenulosis, lipid degeneration, chronic inflammation, atherosclerosis, hereditary diseases, such as Osler-Weber-Rendu disease. The present compound can also be used to control wound healing by inhibiting the formation of adhesions and scars.

Another disease which can be treated according to the present invention is rheumatoid arthritis. Rheumatoid arthritis is a chronic inflammatory disease characterized by nonspecific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Another disease that can be treated according to the present invention are hemangiomas, Osler-Weber-Rendu disease, or hereditary hemorrhagic telangiectasia, solid or blood borne tumors and acquired immune deficiency syndrome.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

EXAMPLES

The following examples are presented in order to more fully illustrate some embodiments of the invention. They should, in no way be construed, however, as limiting the scope of the invention.

Example 1

Synthesis of Targetable Polymer Conjugates

1. Synthesis and Characterization of Co-Monomers:

The monomer HPMA is prepared by the reaction of MA-Cl with aminopropanol at a low temperature in acetonitrile as previously described (Kopecek and Bazilova, 1973). Yield 60%, mp. 67-69° C. $^{1H}$NMR (DMSO-d6, 200 MHz): _ud, J=6.2 Hz, 3H, $CH_3$); 1.65 (s, 3H, $CH_3$_Ma); 3.04 (t, J=6. OHz, 2H,$CH_2$); 3.68 (m, 111, CH); 4.70 (d, J=4.7 Hz, 111, OH); 5.31 (s, 111, CH=); 5.65 (s, 111, CH=); 7.82 (bs, 111, COOH).

The monomer 5-[3-(methacryloylaminopropyl)thioureidyl]-fluorescein (MA-AP-FITC) is prepared as follows: 3-Aminopropyl-methacrylamide was reacted with FITC in DMF, in the presence of triethylamine as described elsewhere (Omelyanenko et al., 1998). Yield 56%, mp. 166.8° C. (decomp.). Extinction coefficient 82,000 $M^{-1}$ $cm^{-1}$ (495 nm, borate buffer pH 9.2, 10% DMF); TLC: R 0.58 (AcOEt/AcOH, 9:1).

The compound p-nitrophenyl-N-acetyllactosamine (LacNAc-pNP) is synthesized in the following way:_pNP-N-acetyl-glucosamine (pNP-GlcNAc) and lactose were incubated with partially purified (β-galactosidase from *Bacillus circulans* in sodium phosphate buffer containing 50% acetonitrile as previously described (Zeng and Uzawa, 2005). After 24 h of incubation, the reaction mixture is concentrated and loaded onto a Toyopearl HW-40S column equilibrated with 25% methanol in water. Eluted fractions containing LacNAc-pNP were collected, concentrated and dried to afford LacNAc-pNP in 18% yield, ESI-MS, 505 m/z for $[M+H]^+$.

The compound p-nitrophenyl-sialyl-N-acetyllactosamine (SLN-pNP) is synthesized. The Synthesis carried out as follows: LacNAc-pNP and CMP-sialic acid disodium salt were incubated with a-(2,3)-N-sialyltransferase in MES buffer containing BSA, $MnCl_2$ and alkaline phosphatase as previously described (Zeng and Uzawa, 2005). After 48 h of incubation, the reaction solution is passed through a Bio-Gel P-2 column, and fractions containing LacNAc-pNP were collected, concentrated and dried to afford SLN-pNP in 83% yield, ESI-MS, 794 m/z for EM–H].

Figure 2:
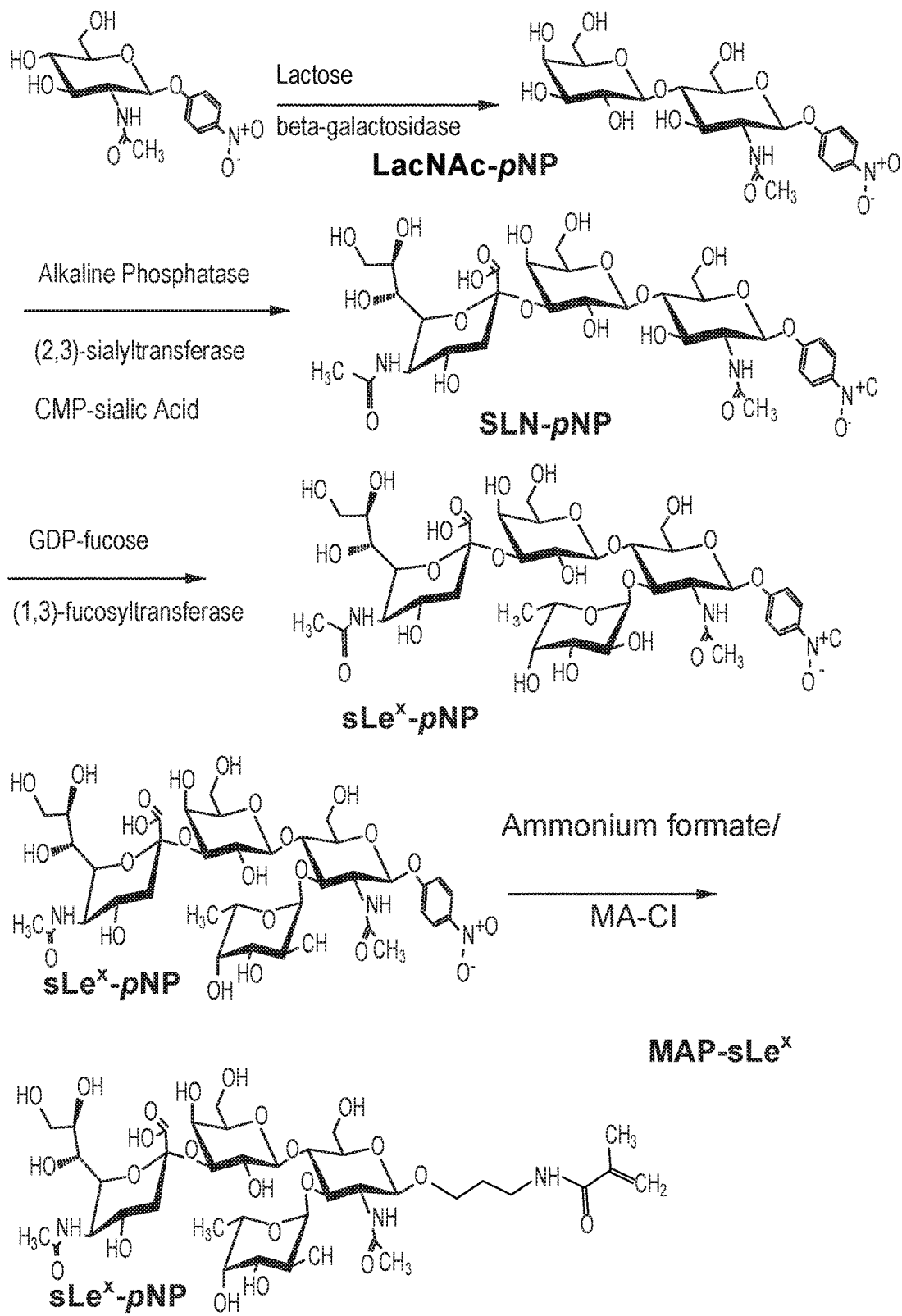
FIG. 2 depicts the synthesis of p-nitrophenyl-sialyl Lewis$^x$ (sLe$^x$-pNP). This conjugate is synthesized by incubating SLN-pNP as the starting sugar with the enzyme α-(1,3)-fucosyltransferase and alkaline phosphatase in HEPES buffer containing bovine serum albumin (BSA) and $MnCl_2$.

Synthesis of p-nitrophenyl-sialyl Lewis$^x$ (sLe$^x$ pNP):

This conjugate is synthesized by incubating SLN-pNP as the starting sugar with the enzyme a-(1,3)-fucosyltransferase and alkaline phosphatase in HEPES buffer containing bovine serum albumin (BSA) and MnCl$_2$, as previously described (Zeng and Uzawa, 2005) (FIG. 2). The reaction mixture is purified on a Bio-Gel P-2 column, and fractions containing the sLe$^x$ pNP are concentrated and dried.

Synthesis of p-(N-methacrylamido)phenyl-sialyl Lewis" MAP-sLe$^x$:

Conversion of the p-nitrophenyl group in sLe$^x$ pNP into the p-(N-methacrylamido)phenyl group is performed via catalytic hydrogenation with Pd/C, followed by treatment with methacryloyl chloride (MA-Cl) in triethylamine-methanol to give the corresponding p-(N-methacrylamido) phenyl glycoside.

Synthesis of N-methacryloyl-aminopropyl-Glutamyl-Glycyl-quinic acid monomer (MAP-Glu-Gly-QA) monomer.

Figure 1:
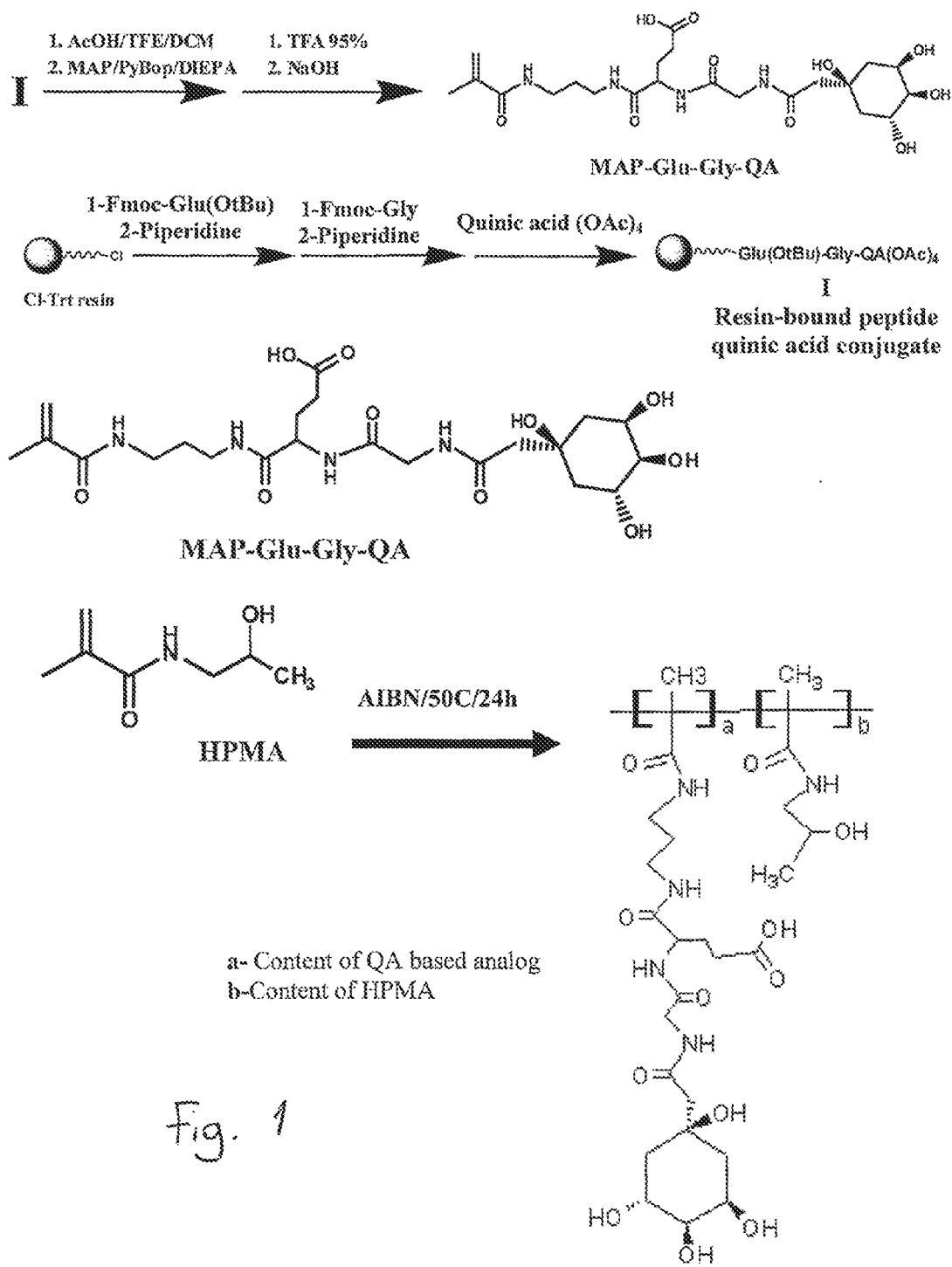
FIG. 1 depicts the synthesis of N-methacryloyl-aminopropyl-Glutamyl-Glycyl-quinic acid (MAP-Glu-Gly-QA) monomer and the corresponding P-Glu-Gly-QA polymer.

The N-methacryloyl-aminopropyl-Glutamyl-Glycyl-quinic acid (MAP-Glu-Gly-QA(OAc)$_4$) acetylated monomer is prepared by Solid Phase Peptide Synthesis (SPPS) using the Fmoc method (FIG. 1). Glutamate (Glu) is coupled with glycine (Gly) in DMF for 2 h at room temperature. The product is then reacted with acetylated quinic acid (QA (OAc)$_4$) under the same conditions. The obtained product is coupled with methacryloyl-aminopropyl (MAP) in DMF for 3 h room temperature to yield the partly protected analog monomer. The reaction product is purified using a preparative HPLC, and characterized with MALDI-TOF. M+Na+ (693) M+K+ (709) for MAP-Glu-Gly-QA(OAc)$_4$.

The de-acetylated monomer is copolymerized with HPMA by radical precipitation polymerization at 50° C. for 24 h using AIBN as the initiator to yield the corresponding the P-Glu-Gly-QA polymer conjugate.

Synthesis of MA-Gly-Phe-Leu-Gly-DOX:

The drug-containing monomer is prepared as described (Rihova and Ulbrich 1990). A lysosomally degradable glycylphenylalanyllleucylglycine (Gly-Phe-Leu-Gly SEQ ID NO: 10) spacer is used as the oligopeptide side chain (for structure see FIG. 4). The conjugate is purified on a Sephadex LH 20 column, with methanol containing 10% dimethyl sulfoxide (DMSO) and 1% CH3COOH as the eluent.

Synthesis of P-Gly-Gly-(Glu)-Gly-Fuc

The t-butyl protected peptide monomer methacryloyl-glycyl-glycyl-(O-t-butyl-glutamyl)-glycine, MA-Gly-Gly-(Glu(OtBu))-Gly-OH is synthesized on solid phase using the standard Fmoc procedure. Gly-Fmoc is loaded to a chlorotrytyl chloride resin overnight and then conjugated with MA-Gly-Gly-OH, followed by coupled to Glu(OtBu) in the same manner as described. The protected peptide is cleaved gently with AcOH:TFE:DCM mixture and purified. The MA-Gly-Gly-(Glu(OtBu))-Gly-OH peptide is copolymerized with HPMA in acetone/DMSO mixture as described previously to yield the polymer precoursor, P-Gly-Gly-(Glu (OtBu))-Gly-OH.

1-aminofucose is prepared by amination of 1-fucose in aqueous solution with large excess of ammonium bicarbonate. This product is then conjugated to P-Gly-Gly-(Glu (OtBu))-Gly-OH in DMSO using BOP and HOBT as coupling reagents. The product is precipitated in ether:acetone mixture, purified by SEC and characterized on LC-MS and H-NMR.

2. Synthesis and Characterization of HPMA Polymer Conjugates:

The HPMA polymers bearing FITC only without sugar (P-MA-FITC) were synthesized as follows: 98 mol % of HPMA and 2 mol % of MA-AP-FITC were dissolved in an acetone/DMSO mixture. Radical precipitation polymerization is carried out at 50° C. over 24 h, with AIBN as the initiator as previously described (David et al., 2001). The labeled conjugates were purified over a Sephadex G-25 column (PD-10 desalting column). Yield: 84%. The content of FITC in polymer is 1.7 mol % as determined spectrophotometrically. Mw of the polymers—as estimated by SEC using a Superose 12 column, FPLC system, calibrated with poly(BPMA) fractions—is 24,000.

The fluorescently labeled polymer (P-sLe$^x$-FITC, without drug) is synthesized by polymerizing the sLe$^x$ monomer (MAP-sLe$^x$) and the FITC-labeled monomer (MA-AP-FITC) with HPMA in acetone/DMSO, with 2,2'-azobis (isobutyronitrile) (AIBN) as the initiator (FIG. 5). HPMA is used as a co-monomer to increase the molecular weight of polymers as well as to improve the molecular flexibility—both properties required for the multivalence binding interactions. The weight ratio of monomer:initiator:solvent is 12.5:0.86:86.7. Similarly, the monomers MA-AP-QA and MA-AP-FITC will be polymerized with HPMA to give the desired P-QA-FITC.

The targeted polymer drug conjugate (P-sLe$^x$-DOX) (FIG. 4) is prepared by polymerizing MAP-sLe$^x$ and the doxorubicin-containing monomer (MA-Gly-Phe-Leu-Gly-DOX) with HPMA under the same conditions as mentioned above. Likewise, the monomers MA-AP-QA and MA-Gly-Phe-Leu-Gly-DOX is employed as monomers to prepare P-QA-DOX (FIG. 4).

Similarly, HPMA polymers bearing DOX only (P-DOX) is synthesized as control. In addition, the control HPMA polymers bearing only the carbohydrate group (P-sLe$^x$) or the non-10 carbohydrate group (P-QA) are prepared.

The concentrations of the sugar residue (sLe$^x$) and QA is determined by LCMS. The concentrations of FITC and DOX are determined spectrophotometrically. The weight average molecular weights (Mw) of the polymers will be estimated by SEC using a Superose 12 column, FPLC system, calibrated with poly(HPMA) fractions.

Example 2

Inhibition Assay for E-Selectin-sLe$^x$ Chimeras

The percentage of inhibition of HL-60 adhesion to recombinant soluble E-selectin coated plates is studied using ELISA plate reader, as described previously (Ramphal J Y, Hiroshige M, Lou B, Gaudino J J, Hayashi M, Chen S M, et al. Ligand interactions with E-selectin. Identification of a new binding site for recognition of N-acyl aromatic glucosamine substituents of sialyl Lewis X. J Med Chem 1996; 39(7):1357-60.). A plate with immobilized E-selectin is exposed to HL-60 cells (which express the natural sLe$^x$ ligand on the cell membrane) in the presence and absence of P-sLe$^x$, P-QA and pHPMA for 15 min at different concentrations. The percentage of bound HL-60 cells is determined with o-phenylenediamine as a substrate for myeloperoxidases released from lysed cells. All assays is performed in duplicates.

Figure 3A:
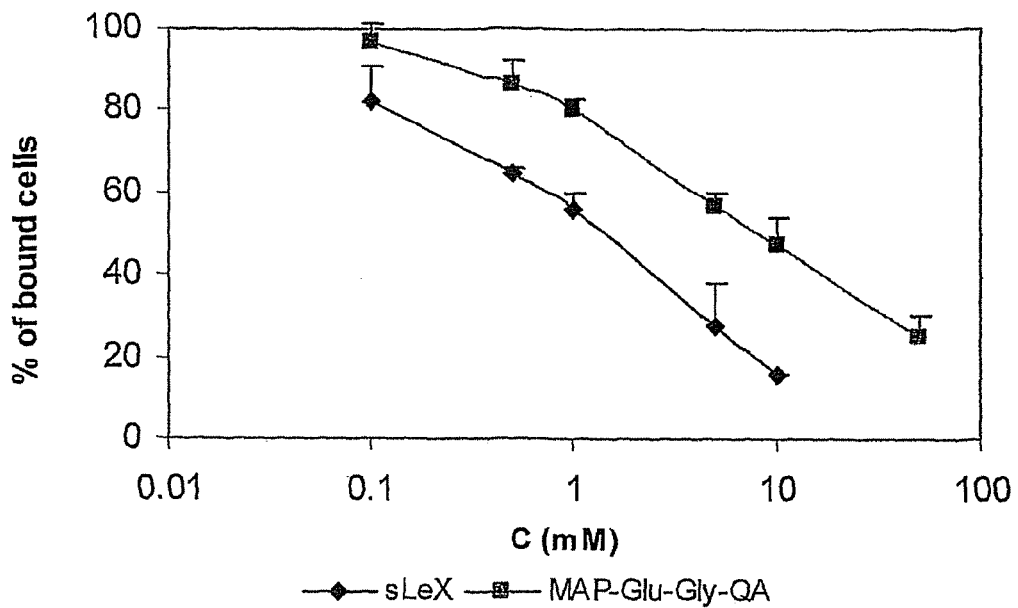
FIG. 3A-C depicts percentage of inhibition of HL-60 adhesion to recombinant soluble E-selectin coated plates is determined using ELISA plate reader, as described previously (Ramphal J Y, Hiroshige M, Lou B, Gaudino J J, Hayashi M, Chen S M, et al. Ligand interactions with Eselectin. Identification of a new binding site for recognition of N-acyl aromatic glucosamine substituents of sialyl Lewis X. J Med Chem 1996; 39(7):1357-60.). A plate with immobilized Eselectin is exposed to HL-60 cells (which express the natural $sLe^x$ ligand on the cell membrane) in the presence and absence of $P-sLe^x$, P-QA and pHPMA for 15 min at different concentrations.
Figure 3B:
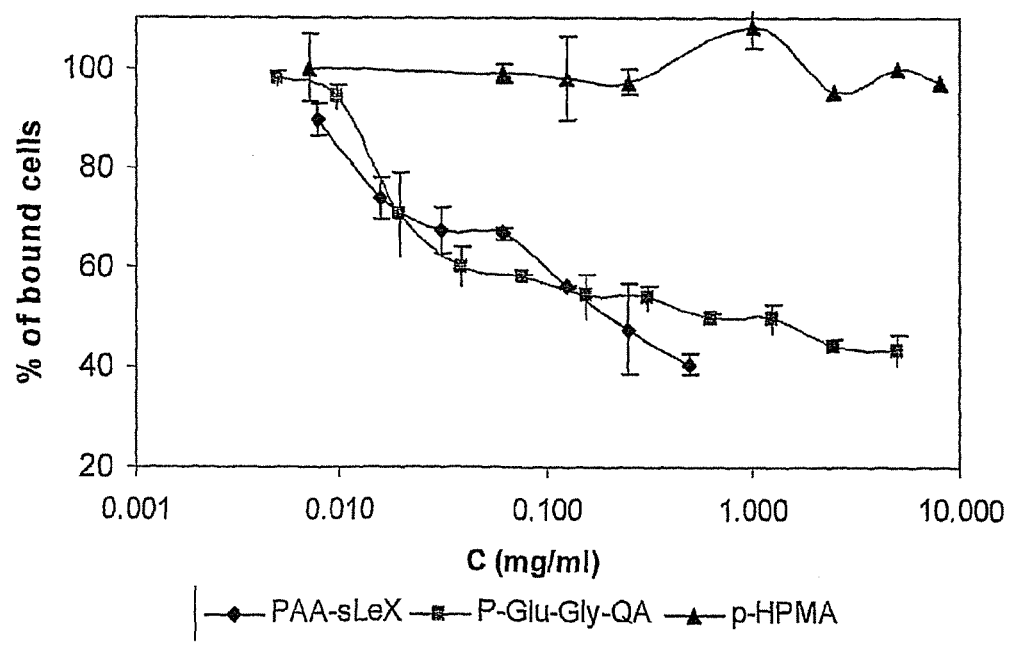
Figure 3C:
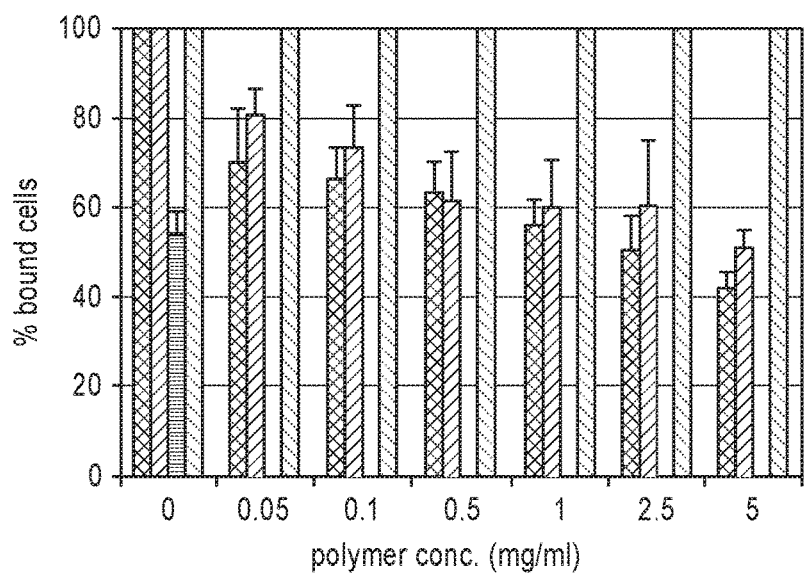

The QA based analog monomer has shown moderate affinity towards E-selectin when compared to sLe$^x$ (FIG. 3A). Inhibition of 50% binding (IC$_{50}$) value is 1.5 mM and 10 mM for sLe$^x$ and MAP-Glu-Gly-QA monomers, respectively. However, polymer conjugates bearing multivalent display of either sLe$^x$ or QA derivative have shown similar binding affinity towards E-selectin, with IC$_{50}$ value of 0.5 mg/ml (FIG. 3B). The binding results also demonstrate that the QA based analog terminated with the dicarboxyl side chain P-Gly-Gly-Lys(Glu)-QA has binding potency equal to that described for P-Glu-Gly-QA (FIG. 3C). This indicates that our proposed drug delivery systems carrying multiple sLe$^x$ and QA derivatives may have the potential to promote the binding of the copolymer drug conjugate to E-selectin expressing vascular endothelium. Of course, the hydrolytic stability of the QA based derivative presents an additional advantage for drug targeting to E-selectin expressing cells.

Table 1 below shows the

The lysosomotropism of the compounds of the invention may be applied, in some embodiments, to the selective release of drugs and/or imaging agents attached to the polymers, via the incorporation of lysosomal degradable spacers.

Example 5

Endothelial Cell Adhesion Under Flow

Adhesion experiments under shear are performed as previously described (Koike et al., 2004). HUVECs cells are

| Copolymer | Mw approx (kDa) [a] | sLe$^x$ mimetic content (mol %) [b] | Distance between QA and CO$_2$H groups (atoms) | IC$_{50}$ (mg/ml) [c] | Equivalent IC$_{50}$ (1 × 10$^6$ mol/L) μM [d] |
|---|---|---|---|---|---|
| PAA-(CH$_2$)$_3$-sLex [e] | 30 | 20 | — | 0.3-0.5 | 50 |
| P-AP-Glu-Gly-QA [f] | 48 | 15 | 9 | 0.5 | 58 |
| P-Gly-Gly-Lys(GluCONH2)-QA | 23 | 15 | 9 | 0.1 | 20 |
| P-Gly-Gly-Lys(Glu)-QA | 40 | 25 | 7, 9 | 1.5-2 | 273 |
| P-Gly-Gly-Lys(Glu-O-tBu)-QA | 22 | 20 | 7 | 3.5-5 | 1600 |
| P-Gly-Gly-(Glu)-Gly-Fuc | 25 | 28 | 9 (from Fuc) | 1 (57%) | 280 |
| P-Gly-Gly-OH | 28 | 22 | — | >5 | >2000 |

[a] Determined by SEC (using Sephacryl S-100 column, FPLC system, calibrated with poly(HPMA) fractions)
[b] Determined by H1-NMR in D20, 500 MHz
[c] Results are mean of 3 experiment performed (in duplicates).
[d] (mol % mimetic content) × (IC50)/(Mw)
[e] PAA-sLeX = polyacrylamide based copolymer (20 mol % sLex, 30 kDa, purchased from Lectinity)
[f] P designates the HPMA copolymer backbone Example 3

Endothelial Cell Adhesion Assay

HUVECs is cultured on a 10-cm gelatin-coated dish or cover glass and stimulated with recombinant human tumor necrosis factor-alpha (TNF-α) for 4 h before treatment to induce surface expression of E-selectin. Control cells is left untreated. Subsequently, P-sLe$^x$-FITC and P-QA-FITC is added to control and TNF-α-treated cells. After 1 h of incubation with the polymer, the cultures are washed, and the cells on the cover glass are fixed with 4% paraformaldehyde (PFA) and mounted in antibleach reagent on slides. The association of the glypolymers is assessed using fluorescence microscopy. The cells grown on 10-cm dishes are harvested, and the obtained pellets is fixed with 4% PFA and analyzed by fluorescence activated cell sorter (FACS).

Example 4

Internalization Studies

Internalization of P-sLe$^x$-FITC and P-QA-FITC conjugates by endothelial cells was studied using confocal laser scanning microscopy (CLSM). Human IVECs grown on cover glass, and treated with the polymer conjugate, and probed for localization of the polymer within lysosomal vessicles. After 24 hours incubation, cells are washed with cold phosphate-buffered saline (PBS) and fixed with 4% PFA. The cells on the cover glass are mounted in antibleach reagent on slides, examined using a CLSM, and analyzed. FIG. 6 demonstrates co-localization of the P-Qa conjugates and of the lysosomal marker indicating the lysosomotropism in E-selectin expressing cells (human IVECs).

grown on gelatin-coated 24-well plates. Cells are stimulated with TNF-α for 4 h. Then, P-sLe$^x$-FITC and P-QA-FITC is added to the medium to a final concentration of 10 μg/ml in the presence or the absence of anti-E-selectin or free sLe$^x$. The cells are incubated on a rotating platform under shear (90 rpm with a rotary shaker) for 1 h at 37° C. Control cells are incubated as above without rotation. After incubation, nonadherent polymer conjugates is washed out 3 times with cold PBS, and the cells are lysed with 0.5% Nonidet P-40. Cells are counted by measuring fluorescence intensity.

Example 6

Endothelial Cell Cytotoxicity Assay

The cytotoxicity of free DOX, non-glycosylated DOX polymer conjugate (P-DOX), and the targeted DOX-polymer conjugates [P-sLex-DOX and P-QA-DOX] towards activated HUVECs is assessed by means of the 3-(4,5-dimethylthiazol-2-yl)-2,5-diphenyltetrazolium bromide (MTT) assay. The results of this cytotoxicity assay are used to calculate the IC50 dose (drug concentration causing 50% growth inhibition) relative to a control of non-treated cells (David et al., 2004). Cells are seeded into gelatin-coated 96-well microtiter plates at a density of 10,000 cells per well. Twenty-four hours after plating, the medium is removed, and the cells are stimulated with TNF-α for 4 h. Subsequently, 12 different concentrations of sterile products [P-sLex-DOX, P-QA-DOX, P-DOX or free DOX] in fresh media are added, followed by 72 h of incubation at 37° C., under 5% CO2 (v/v) in air. Cell survival is determined by MTT viability assay.

Example 7

Mouse Xenograft Model of Human Prostate Cancer

Thirty-five 8-week-old BALB/c nude mice (25-30 g) are injected s.c. in the flank with 3 million LNCaP human prostate adenocarcinoma cells suspended in 1:1 medium: Matrigel™ as described (Farokhzad et al., 2006). All experiments are initiated when tumor volumes have reached approximately 0.3-0.4 cm$^3$. During experiments, the animals are sedated with an intraperitoneal injection of 2.5% avertin (0.02 mug body weight) and are studied under approved protocol of Animal Care.

Example 8

In Vivo Antitumor Activity

Therapy experiments are initiated when tumors reaches approximately 0.3 cm$^3$. The mice are divided into five groups of seven mice such that weight and tumor size differences are minimized. The tumor-bearing mice are each given three i.v. injections, at 3-day intervals, of P-sLe$^x$-DOX (2.5 or 10 μg), P-QA-DOX, p-HPMA, free DOX (the equivalent concentration), or saline. The mice are weighed and implanted tumor size is monitored daily for two weeks and every three days thereafter. The animals are sacrificed on day 21. The length and width of the tumors is measured by calipers in three dimensions, and the tumor volume is calculated by the following formula: (width$^2$×length)/2. Tissue samples are obtained from liver, spleen, kidney, and tumors. In parallel to the above, organ tissue samples of tumors before drug treatment are obtained. For histopathological examination, tissue samples are fixed in 10% buffered-formalin, embedded in paraffin, cut into 5-□m sections and stained with hematoxylin and eosin (H&E).

Example 9

Histological Analyses

Formalin-fixed, paraffin-embedded tissue slides from median tumors derived from the LNCaP prostate adenocarcinoma tumors (not treated with drug conjugates) are deparaffinized and incubated with either 100 gl P-sLe$^x$-FITC, P-QA-FITC or free p-HPMA (0.025 mg/mL; diluted with PBS buffer, pH 7.3) for 1 h at room temperature. Control specimens are incubated under the same conditions with PBS buffer alone. Specificity of P-sLe$^x$-FITC, P-QA-FITC and P-MA-FITC binding is verified by competitive inhibition with the appropriate free saccharides (L$^x$) prior to incubation. For this purpose, 100 μl of a 0.4 M sugar solution is mixed with 100 μl P-sLe$^x$-FITC, P-QA-FITC or P-MA-FITC solutions, and added to the cells or slides. After incubation, slides are washed three times with PBS and analyzed by light microscopy. Histological analyses is performed. P-sLe$^x$-FITC localization near and in the vascular endothelium is visualized by fluorescence microscopy at 510 nm. Background auto-fluorescence is assessed using PBS-treated control specimens. The distribution of tissue and cellular fluorescence is evaluated, as will the intensity of the fluorescence.

Example 10

In Vivo Adhesion to Tumor Cells vs. Tumor Endothelial Cells

Single-cell suspensions of fresh tumor tissues derived from the LNCaP prostate tumors (see section 2.7) are prepared according to a previously described method (Zitzmann et al., 2002). To determine the target cells of P-sLe$^x$-FITC binding within the xenograft, the cells suspension are incubated for 1 h with the labeled polymer conjugate, stained with 4'-6-diamidino-2-phenylindole (DAPI), and analyzed by FACS to detect differences in cell populations, cell size and granularity. To further characterize the mouse cells in the tumor-derived single-cell suspension, the endothelial-specific antibody PECAM-1 (CD31) is used. The binding of P-sLe$^x$-FITC and PECAM-1 to the cells is compared.

Example 11

Drug Distribution in the Tumor

To analyze the distribution of P-sLe$^x$-DOX, P-QA-DOX, p-HPMA, and free DOX, frozen 5-μm tissue sections from tumors and organs of treated mice (section 2.7) are prepared (section 2.8). The fluorescent substances are visualized by fluorescence microscopy on using the following filters for DOX: excitation: 527-552 nm, emission: 577-632 nm. The microphotographs are processed as previously described (Minko et al., 2000).

Example 12

Pharmacoldnetics in Rats

To test the physiological stability of P-QA-FITC compared to P-sLe$^x$-FITC and P-AP-FITC, jugular vein cannulated Sprague Dawley male rats (~200 g) are used. Animals are divided into 5 groups of three rats with minimal weight variation. Rats are administered with a single 20 mg/kg i.v. injection of P-sLe$^x$-FITC, P-QA-FITC, P-AP-FITC, p-HPMA or saline. Blood is collected from each rat at 5 min, 0.5, 0.75, 1, 2, 4, 8, and 24 h after dosing. Equal volume of saline is given to replace the lost blood. Plasma levels of test compounds are assayed by HPLC using fluorescent detector.

Example 13

Synthesis of Additional Embodied Polymer Conjugates

Synthesis and Characterization of Monomers: N-(2-hydroxypropyl)methacrylamide monomer (HPMA)

HPMA was previously synthesized according to previous protocol (Ruttekolk I R, Duchardt F, Fischer R, WiesmUller K H, Rademann J, Brock R., HPMA as a scaffold for the modular assembly of functional peptide polymers by native chemical ligation, Bioconjug Chem. 2008, 19(10):2081-7). Dichloromethane (DCM, 20 ml), sodium carbonate (24 g, 0.231 mol) and lamino-2-propanol (17.8 ml, 0.231 mol) were mixed. Methacryloyl chloride (22.5 ml, 0.231 mol) was diluted with DCM (22.5 ml) and was added drop-wise under vigorous stirring and cooling to 0° C. The reaction mixture was stirred at room temperature for 1 hour and then dried with magnesium sulfate and filtered to remove the inorganic solids. The filtrate was concentrated using rotoevaporator under vacuum and was then left to crystallize overnight in the freezer. The product was characterized by TLC (Rf in acetone=0.63).

5-[3-(methacryloylaminopropyl)thioureidyl]fuorescein monomer (MA-FITC)

This monomer is used in order to view and confirm internalization into the cells. FITC monomer was prepared according to published protocoh[7]. FITC (Flourescein Isothiocyanate, 0.5 mmol) and 3-Aminopropylmethacrylamide (APMA, 0.6 mmol) were mixed and dissolved in dimethylformamide (DMF, 1 ml). Triethylamine (TEA, 1.1 mmol) was added drop-wise to the solution, mole ratio of reagents is FITC: APMA: TEA=1:1.2:2.2 and the mixture was stirred in the dark for 48 hours in the presence of inhibitor (tert-oxtylpyrocatechine) to prevent polymerization. After evaporating the solvent using rotoevaporator under vacuum, the solution was precipitated into acidified water (10% in glacial acetic acid). The mixture was centrifuged and dried. The product was characterized by TLC (R$_f$ in EtOAc/CH$_3$COOH 9:1=0.6), extinction coefficient 78,000 M$^{-1}$ cm$^1$ (0.1M sodium tetraborate *10H$_2$0 in 1% EtOH, pH~9).

Synthesis of N-Methacryloylglycylglycine p-nitrophenyl ester (MA-GG-Np)

MA-GG-ONp was synthesized by reacting methacryloyl chloride (MA-Cl) with glycylglycine (Gly-Gly-OH) in a basic solution to give the methacryloylglycylclycine (MA-Gly-Gly-OH), which was then coupled with p-nitrophenol (PN-p) to give MA-GG-ONp, as described previously.

Synthesis of E-selectin binding peptide monomer with Cysteine in the N terminal (Cys-Esbp-):

The peptide CDITWDQLWDLMK (SEQ ID NO: 11) was synthesized on an automated synthesizer using Rink Amide MBHA as a solid phase resin. The peptide was cleaved from the resin with TFA:TIS:H$_2$O (95:2.5:2.5) mixture for 2 hr at r.t. TFA was evaporated and the peptide was precipitated in ether and purified in preparative HPLC and characterized with MALDI-TOF (unprotected peptide M$^+$ 1699) and H-NMR.

Synthesis and Characterization of Poymer: Synthesis of HPMA-GG-ONP-FITC polymer (P-GG-ONP)

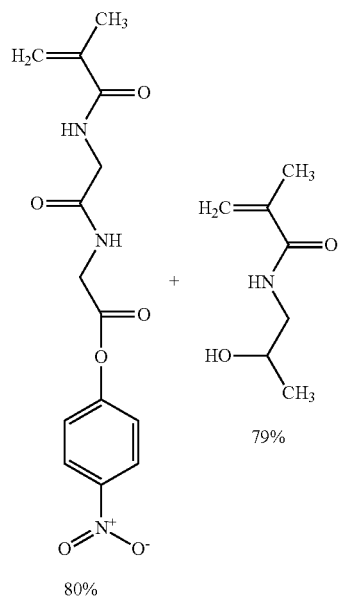

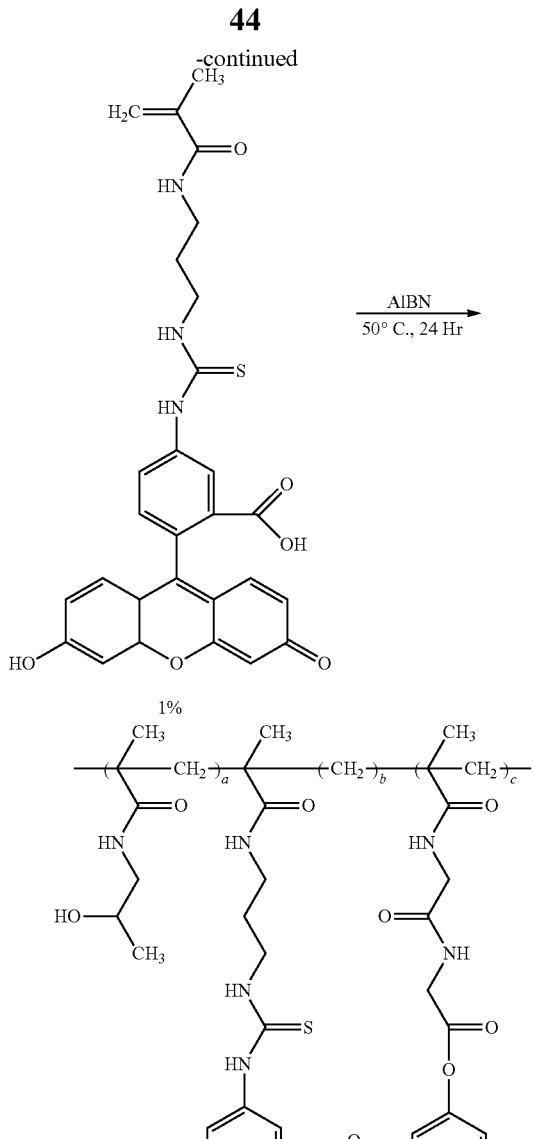

| Labled Polymer | | | | |
|---|---|---|---|---|
| monomer | Mw | % mol | mmol | mg |
| HPMA | 143 | 79 | 2.5 | 357.5 |
| FITC | 533 | 1 | 0.03125 | 16.7 |
| Analog | 321 | 20 | 0.625 | 200.6 |
| Total mg | | | | 574.8 |

Reaction Mixture:
HPMA—0.0357 gr
MA-GG-ONP—0.200 gr
MA-FITC—0.016 gr
AIBN 0.0273 g
Acetone 5 ml (take off DMSO or MeOH)

Procedure:

MA-FITC and MA-GG-ONP were dissolved in 0.3 ml DMSO, HPMA and AIBN were dissolved in 4.7 ml Acetone. The mixture was bubbled in nitrogen for 5 min and sealed in a vial+parafihn. The vile was stirred for 48 hr in 55-60° C. Copolymer was precipitated in ether: acetone 3:1 and purified in LH20 in methanol and dried in a desiccator.

The content of FITC and MA-GG-ONp in the copolymer was determined spectrophotometrically to be 1.6 mol % and 15 mol %, respectively.

Synthesis of HPMA-Peptide Conjugates via Native Chemical Ligation (NCL)*:

P-GG-ONP (4 mg) was dissolved in anhydrous DMSO (200 μL), and benzylmercaptan (50 μL) was added. After 15 min, Cys-Esbp peptide was dissolved in this solution (4.4 to 11.2 mM corresponding to an 8- to 20-fold excess over polymer and 0.64 to 1.60 excess over reactive groups, respectively) and incubated for 30 min at 20° C. After addition of thiophenol (50 μL) and incubation for 16 h at 20° C., phosphate buffer (100 mM) and guanidinium chloride (6 M), pH 7.5 (200 μL), were added and the mixture incubated for 72 h at 20° C. Finally, the reaction mixture was diluted with PBS (700, uL) and purified twice with a PD-10 column followed by lyophilization. The formation of a conjugate was validated using analytical gel filtration chromatography (A" KTA-explorer fast protein liquid chromatography (FPLC) station; flow, 0.25 ml/min; 4° C.; Sephacryl S-200 HR-column, 150'10 mm). Absorption was detected at 215 nm (peptide bonds), 280 nm (aromatics), and 492 nm (fluorescein).

Peptides having a sequence of DITWDQLWDLMK (SEQ ID NO: 3) have been shown to inhibit leukocyte adhesion at IC50 of 4 nM, and is referred to as E-selectin Binding Peptide (Esbp). Thus it was of interest whether conjugation of such peptides to polymers as described herein would be useful for the therapeutic and diagnostic applications described.

Synthesis of Labeled Polymer Peptide Conjugate: P-Esbp

The overall synthesis was conducted according to the scheme:

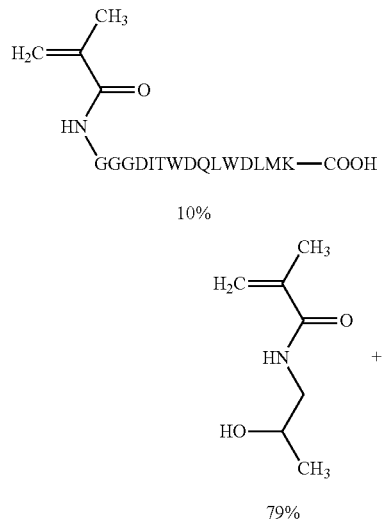

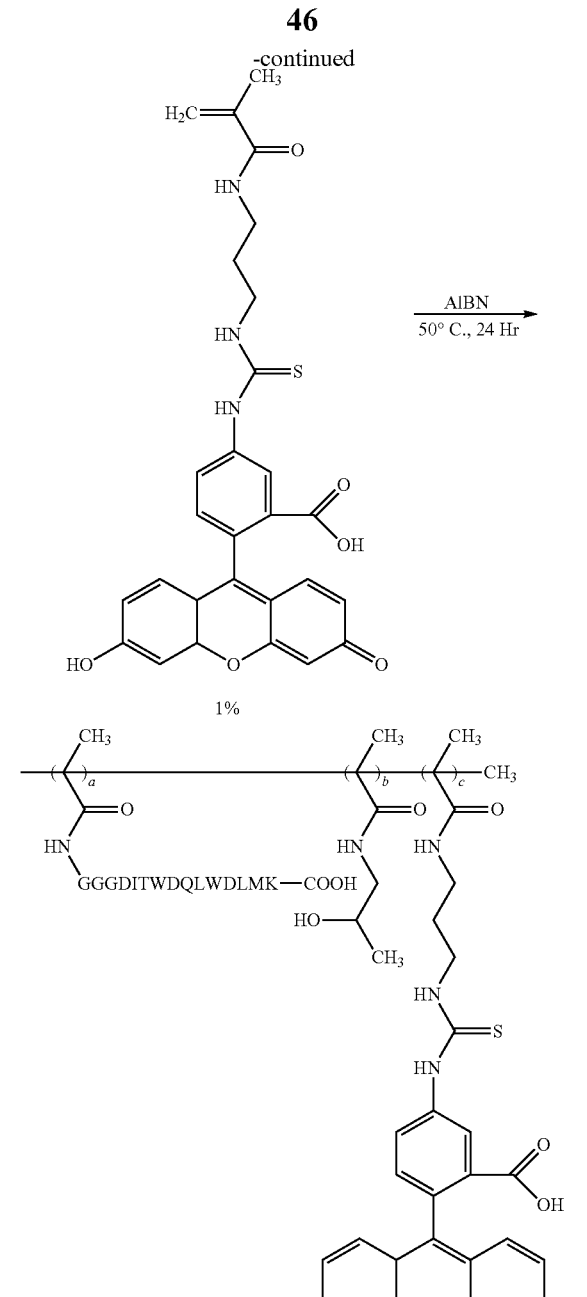

| Polymer Feeding Ratio | | | | |
|---|---|---|---|---|
| monomer | Mw | % mol | mmol | mg |
| HPMA | 143 | 89 | 0.12 | 17.2 |
| FITC | 533 | 1 | 0.0013333 | 0.7 |
| Peptide monomer | 2500 | 10 | 0.0133333 | 33.3 |
| Total mg | | | | 51.2 |

5 mg AIBN and 17.2 mg HPMA were dissolved in 200 μL acetone. 1 mg of MA-FITC and 33 mg of protected peptide monomer MA-GGGDITWDQLWDLMK were dissolved in 200 μL DMF. The solvents were combined in a 2 ml vial. A magnetic stirrer was added and nitrogen was bubbled for 5 min. The reaction mixture was stirred for 48 hrs. The mixture was precipitated into cold diethyl ether. The ether was discarded after centrifugation (15 min). The yellow solid was dried in desiccator for 30 min. Protecting groups were removed with: TFA:H2O:EDT:TIS (5.4:0.15:0.15: 0.06) shaken for 2 hours. TFA was removed with air streaming through a pipette. Cold ether was added and the precipitate was centrifuged and dried in a desiccator. The dried copolymer was dissolved in DDW and purified with PD-10 Column. Product was lyophilized in the dark overnight. 25 mg of polymer were obtained, analyzed in H-NMR, FPLC and amino acid analysis.

Synthesis of MA-GGG-DITWDQLWDLMK. E-selectin binding peptide monomer (MA-GGG-Esbp).

The peptide monomer MA-GGG-DITWDQLWDLMK was synthesized on automated synthesizer using chlorotrytil chloride as a solid phase resin. The resin was swelled and loaded with first amino acid in dry dichloromethane over night. MA-GG-OH was added as the last amino acid in the sequence GDITWDQLWDLMK (SEQ ID NO: 9). The peptide monomer was cleaved from the resin with AcOH: TFE:DCM (2:2:6) mixture for 2 hr at r.t. The mixture was evaporated with hexane twice and methanol twice until white powder appeared and no AcOH was left. The peptide was purified in preparative HPLC and characterized with MALDI-TOF (unprotected peptide M$^+$ 1799) and H-NMR.

Synthesis of Scrambled monomer: MA-GGG-KMID-WTWLQLDD.

The peptide monomer MA-GGG-KMIDWTWLQLDD was synthesized on automated synthesizer using chlorotrytil chloride as a solid phase resin. The resin was swelled and loaded with first amino acid in dry dichloromethane over night. MA-GG-OH was added as the last amino acid in the sequence G KMIDWTWLQLDD (SEQ ID NO: 8). The peptide monomer was cleaved from the resin with AcOH: TFE:DCM (2:2:6) mixture for 2 hr at r.t. The mixture was evaporated with hexane twice and methanol twice until white powder appeared and no AcOH was left. The peptide was purified in preparative HPLC and characterized with MALDI-TOF (unprotected peptide M$^+$ 1799) and H-NMR.

Confocal Microscopy

Confocal microscopy was used to evaluate the subcellular fate of the FITC labeled copolymer conjugates by human immortalized vascular endothelial cells, IVECs. Lysotracker Red DND-99 (Molecular Probes, Leiden, The Netherlands) was selected to visualize lysosomes. Cells (3×104) were seeded onto gelatin coated cover slips in 24 wells plate with 500 µL endothelial cells culture medium (Promocell) and incubated for 24 hr. The cells were then activated with 10 ng/ml TNFα in medium for 4 hrs to induce surface expression of E-selectin. Control cells were left untreated. Subsequently, 50 µg/ml of the FITC-labeled copolymer conjugates was added to control and TNF-α-treated cells and incubated for 8 hrs. Cells were subsequently rinsed three times with media and were exposed to Lysotracker (50 nM, 60 min, 37° C.), after which they were rinsed three times with cold PBS, fixed in 3% paraformaldehyde, and mounted in Mowiol-DABCO (Aldrich Chemical Co., Milwaukee, Wis.; Sigma, St. Louis, Mo., respectively) mounting medium. Images were acquired with a Fluor filter block (excitation at 488 nm, emission collected with a 515-nm barrier filter), followed by a red filter analysis (excitation at 543 nm, emission collected with a 570-nm barrier filter). Autofluorescence background was ascertained using control (untreated) cells. Quantitative analysis was performed using Image-Pro Plus 4.0 (Media Cybernetics, Silver Spring, Md.). Fluorescence intensities were expressed in arbitrary units per square micron. Data were normalized to the number of cells per unit field.

Evaluation of Binding Affinity for Esbp and P-Esbp

Inhibition assays confirmed the high binding affinity of Esbp monomer with similar values as published in the litrature (1-10 µM). HPMA-Esbp copolymer, P-Esbp showed an increase of 3 orders of magnitude in binding affinity with IC50 value of 20 nM (FIGS. 7A and 7B).

Example 14

Uptake of P-Esbp by Activated and Non Activated IVECs

Confocal microscopy was used to evaluate the uptake of P-Esbp. Immortalized vascular endothelial cells (IVEC) were untreated or treated with TNFα in medium for 4 hr. After removal of medium cells were incubated with 0.5 ml medium with 50 µg/ml of FITC labeled P-Esbp solution for 6 or 24 hours and subjected to fluorescence microscopy. A significant increase in uptake of P-Esbp was seen in activated IVECs (FIG. 8C and FIG. 8D) relative to non activated cells (FIGS. 8A and FIG. 8B), which can be related to E-selectin expression. P-Esbp internalization to lysosomal compartment is shown in FIG. 9.

The average fluoresence intensity was calculated using ImageJ v1.40G software and is shown in FIG. 10. The intensity was divided by the area of the cells. The data represents an average of 30 different images of confocal microscopy. An 8-9 fold increase in intensity was seen for P-Esbp in activated cells wherease P-2 showed no significant increase.

Example 15

Uptake of P-Esbp by IVECs was Examined by Flow Cytometry Experiments

Flow cytometry assays were conducted on IVECs incubated with P-Esbp and revealed enhanced P-Esbp binding and internalization in activated cells. Experiments conducted at 4° C. where no endocytosis occurs demonstrated binding to E-selectin on the membrane in activated IVECs (FIGS. 11A & 11B) relative to non activated cells (FIGS. 11C & 11D). At 37° C. P-Esbp uptake again was increased 4-fold upon activation (FIGS. 11E & 11F).

Example 16

Binding of P-Esbp and Scrambled Esbp Polymer Conjugates to E-Selectin

Figure 13A:
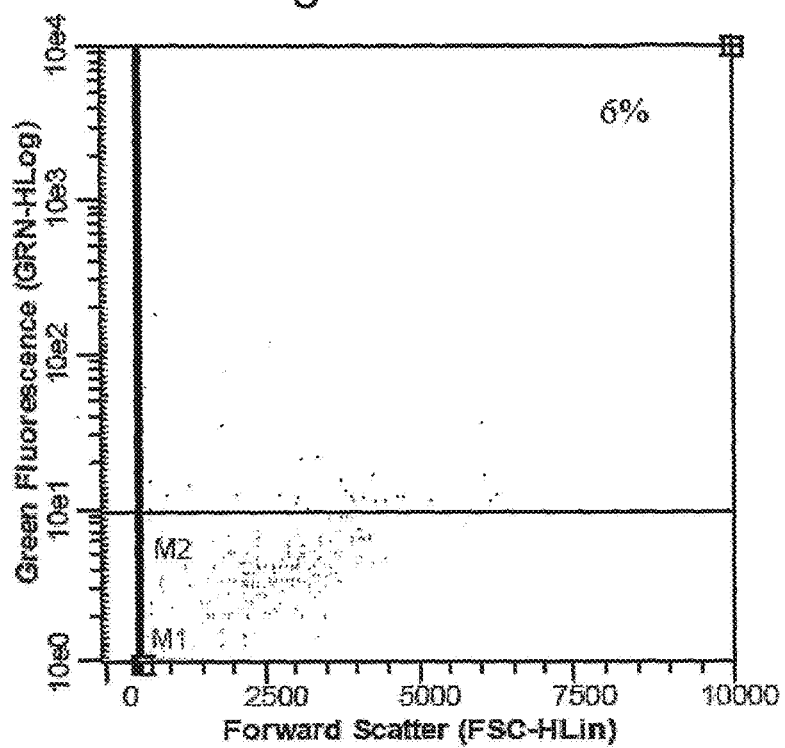
Figure 13B:
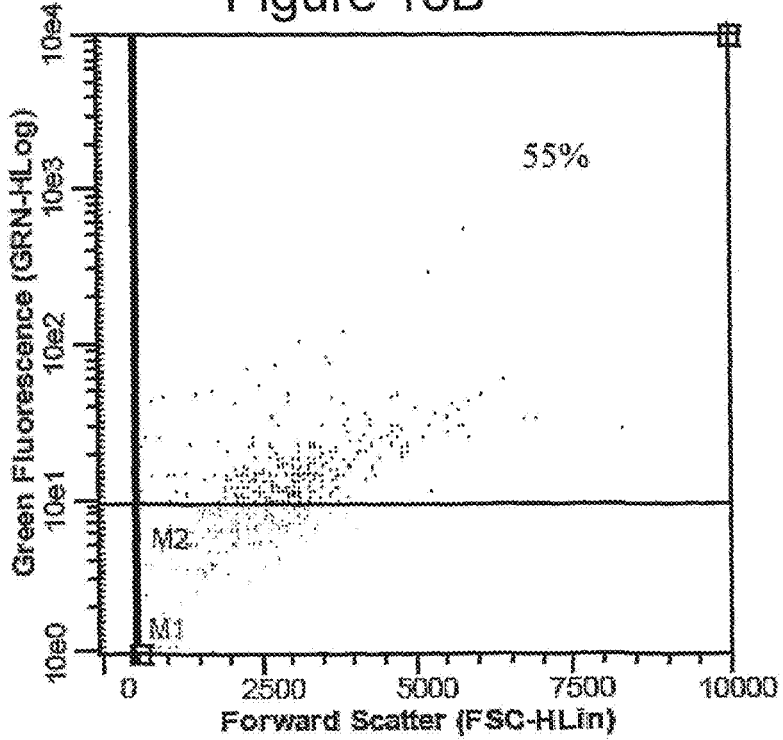
Figure 13C:
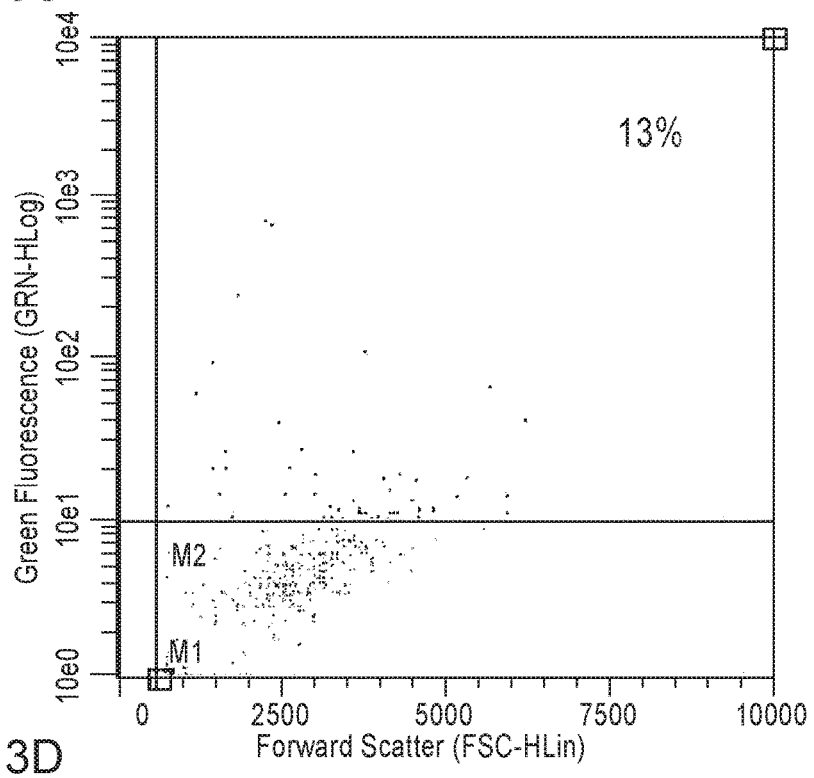
Figure 13D:
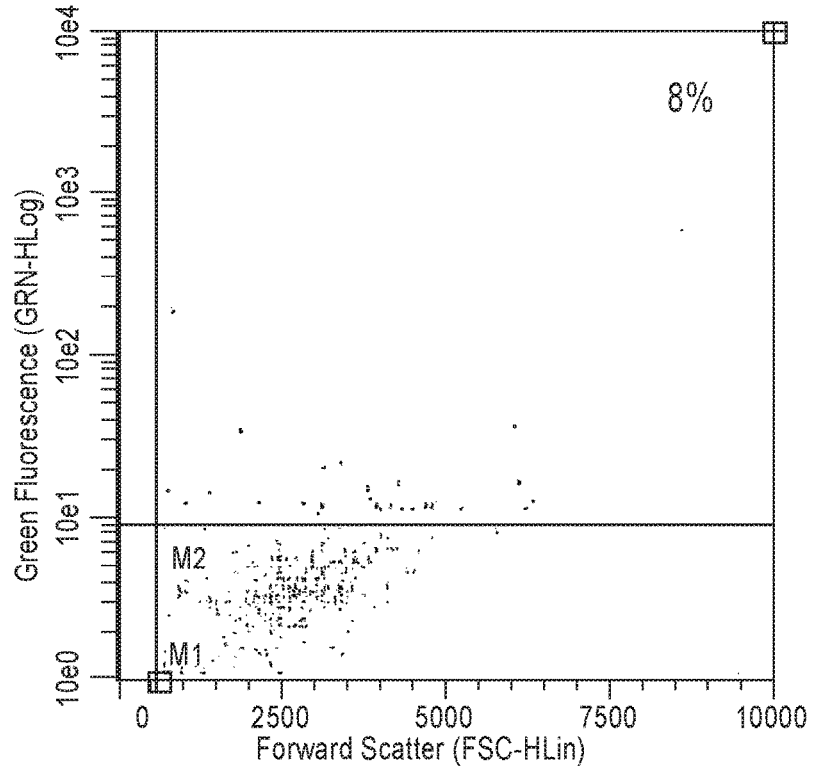

E-selectin expressing cells were treated with P-Esbp and P-Scrmb as described in previous examples, to determine binding, in activated and non-activated cells (FIG. 12). Cells were treated with P-Esbp and P-Scrmb conjugates for 1 h at 4° C. and evaluated for binding. The percentage of labeled cells treated with P-Esbp and P-Scrmb conjugates was 85% and 6%, respectively. Unactivated Cells (FIGS. 12A and C) were treated with P-Esbp and P-Scrmb, respectively and compared to that of activated cells (FIGS. 12B and D, respectively). Binding of P-Esbp and scrambled Esbp peptide sequence polymer conjugates (P-Scrmb) to E-selectin expressing cells was similarly evaluated, when cells were also contacted with or without free peptides (FIG. 13). Unactivated Cells (FIG. 13A and data not shown) were treated with P-Esbp and P-Scrmb, respectively (at a concentration of 50 µg/ml) and compared to that of activated cells (FIG. 13B and data not shown, respectively). Activated cells were in addition contacted with 25 and 50 μg/ml of P-Esbp (FIGS. 13C & D), and unactivated cells were also contacted with 50 μg/ml of P-Esbp (data not shown). Activated cells were in addition contacted with 25 and 50 μg/ml of PScrmb (data not shown). The scrambled peptide had a sequence corresponding to GKMIDWTWLQLDD (SEQ ID NO: 8), while the Esbp had a sequence corresponding to GDITWDQLWDLMK (SEQ ID NO: 9).

Example 17

Internalization Studies

Internalization of P-Esbp-FITC conjugates was compared to that of P-Scrmb-FITC conjugates by endothelial cells was assessed as in Example 4. FIG. 14 demonstrates co-localization of the P-Qa conjugates and of the lysosomal marker indicating the lysosomotropism in E-selectin expressing cells (human IVECs). Non-activated (FIGS. 14A-C) and Activated cells (FIGS. 14D-F) were visualized to determine localization of the conjugates (14A and 14D) relative to that of the lysosomal compartments (14B and 14E), and colocalization of the signals was assessed (14C and 14F). Colocalization was only seen in activated cells (arrows). Similar evaluation of P-Scrmb-FITC did not show reasonable internalization or colocalization (data not shown).

The lysosomotropism of the compounds of the invention may be applied, in some embodiments, to the selective release of drugs and/or imaging agents attached to the polymers, via the incorporation of lysosomal degradable spacers.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

What is claimed is:

1. A polymer comprising repeating units

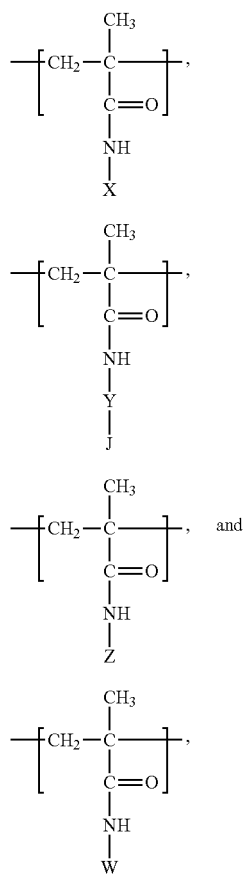

wherein

X is 2-hydroxypropyl;

Y is a tripeptide selected from the group consisting of GGG and GGC, wherein the amide nitrogen shown in (b) is part of the initial G residue;

J is a peptide targeting moiety having the sequence of SEQ ID NO: 2, wherein J is bonded to Y at the terminal G or C residue;

Z is a drug optionally comprising a spacer; and

W is an imaging agent optionally comprising a spacer; and wherein between about 50% and 99.95% of the total repeating units in the polymer are (a) or derivatives of (a); between 0.05% and 50% of the total repeating units in the polymer are (b), between about 0 to 50% of the total repeating units in the polymer are (c), and between 0 to 15% of the total repeating units in the polymer are (d).

2. The polymer of claim 1, wherein the optional spacer attached to Z comprises an acid cleavable spacer.

3. The polymer of claim 1, wherein said spacer attached to Z is a peptide, an alkane or an alkene.

4. The polymer of claim 1, wherein said polymer is represented by the following structure:

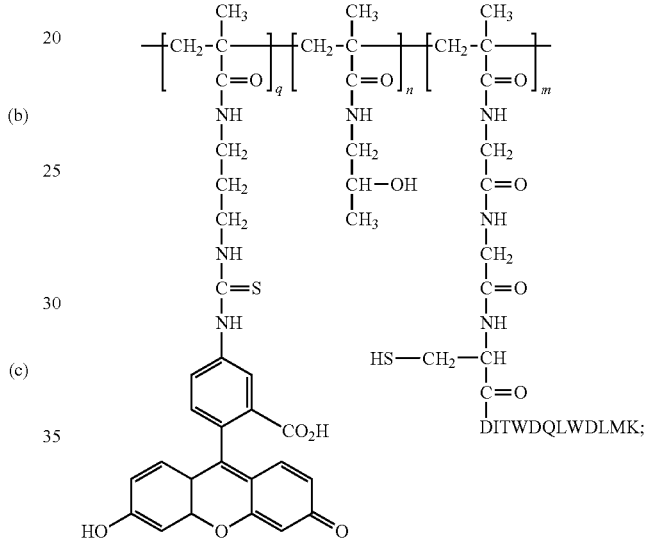

with q, n, and m as percentages of the monomers, wherein m is 0.05%-50%, n is between about 50% and about 99.95%, and q is between about 0% and about 25%.

5. A pharmaceutical composition comprising the polymer of claim 1.

6. The pharmaceutical composition of claim 5, wherein the drug is an antineoplastic compound, a therapeutic compound, a toxin, an anti-inflammatory compound, or an immunotherapeutic agent.

7. A method of treating an inflammatory condition comprising administering a pharmaceutical composition comprising the polymer of claim 1 to a subject.

8. A method of diagnosing cancer in a subject, the method comprising contacting a polymer of claim 1 with a neoplastic cell or with vasculature associated with a neoplastic cell in a subject.

9. The method of claim 7, wherein the inflammatory condition is selected from the group consisting of rheumatoid arthritis, asthma, transplant rejection, psoriasis, inflammatory bowel disease, ischemia injury, diabetes, and multiple sclerosis.

10. A method of treating a disease associated with neovascularization in a subject comprising administering a polymer of claim 1 to the subject.

11. The method of claim 9, wherein said polymer binds active endothelial cells on cancer or inflamed tissue.

12. The method of claim 11, wherein said spacer in Z cleaves after said polymer binds activated endothelial cells, cancer or inflamed tissue.

13. A method of treating a disease associated with neovascularization in a subject comprising administering a pharmaceutical composition comprising the polymer of claim 1 to the subject.

14. A method of, reducing the incidence of, delaying progression of, reducing the pathogenesis of, or prolonging remission of cancer in a subject comprising administering a pharmaceutical composition comprising the polymer of claim 1 to the subject.

15. The method of claim 14, wherein said polymer binds to receptors on the angiogenic blood vessels of the cancer.

16. The method of claim 14, wherein said spacer in Z cleaves after said polymer binds the endothelial cells associated with the cancer.

17. A method for inhibiting metastasis of a cancer in a subject comprising administering a pharmaceutical composition comprising the polymer of claim 1 to the subject.

18. The method of claim 17, wherein said polymer binds to receptors on activated endothelial cells.

19. The method of claim 18, wherein said spacer in Z cleaves after said polymer binds said activated endothelial cells.

20. The method of claim 7, wherein the inflammatory condition is atherosclerosis.

* * * * *